(12) United States Patent
Zhang et al.

(10) Patent No.: US 9,594,086 B2
(45) Date of Patent: Mar. 14, 2017

(54) BIOMARKERS FOR AGGRESSIVE PROSTATE CANCER

(75) Inventors: Hui Zhang, Ellicott City, MD (US); Yuan Tian, Baltimore, MD (US); Daniel W. Chan, Clarksville, MD (US); Jing Chen, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 14/006,503

(22) PCT Filed: Mar. 22, 2012

(86) PCT No.: PCT/US2012/030129
§ 371 (c)(1),
(2), (4) Date: Oct. 9, 2013

(87) PCT Pub. No.: WO2012/129408
PCT Pub. Date: Sep. 27, 2012

(65) Prior Publication Data
US 2014/0106369 A1   Apr. 17, 2014

Related U.S. Application Data

(60) Provisional application No. 61/466,173, filed on Mar. 22, 2011, provisional application No. 61/523,548, filed on Aug. 15, 2011, provisional application No. 61/598,582, filed on Feb. 14, 2012.

(51) Int. Cl.
*G01N 33/53* (2006.01)
*G01N 33/68* (2006.01)
*G01N 33/574* (2006.01)

(52) U.S. Cl.
CPC ... *G01N 33/6893* (2013.01); *G01N 33/57434* (2013.01)

(58) Field of Classification Search
None
See application file for complete search history.

(56) References Cited

U.S. PATENT DOCUMENTS

2010/0216654 A1   8/2010   Stedronsky et al.

FOREIGN PATENT DOCUMENTS

WO   WO 2009/138392 A1 * 11/2009
WO        2010081240 A1    7/2010

OTHER PUBLICATIONS

Wright et al (Urol Oncol, 1995, 1(1): 18-28).*
Shousha et al (British Medical Journal, 1979, 1(6166): 777-779).*
Halvorsen et al (Clin Cancer Res, 2007, 13(3): 892-897).*
Domingo-Domenech et al (Annals of Oncology, 2008, 19: 269-275).*
Shahrokh et al (Urology, 2001, 58(6): 1008-1015).*
Nishiyama et al (The Journal of Urology, 2006, 176: 1387-1391).*
Nishimura et al (Jouranl of Proteomics, 2010, 73: 1100-1110).*
Nomura, T., et al., "Involvement of cathepsins in the invasion, metastasis and proliferation of cancer cells", J Med Invest, Feb. 2005, vol. 52, pp. 1-9.
Gopal, P., et al., "Matrigel influences morphology and cathepsin B distribution of prostate cancer PC3 cells", Oncology Reports, (2006), vol. 16, pp. 313-320.
Colella, R., et al., "Increased cell density decreases cysteine proteinase inhibitor activity and increases invasive ability of two prostate tumor cell lines", Cancer Letters (2002) vol. 185, pp. 163-172.

* cited by examiner

*Primary Examiner* — Sean Aeder
(74) *Attorney, Agent, or Firm* — Johns Hopkins Technology Transfer

(57) ABSTRACT

The present invention relates to the field of biomarkers and, more specifically, to biomarkers useful in diagnosing aggressive prostate cancer. In specific embodiments, a method for diagnosing aggressive prostate cancer in a patient comprises (a) measuring the levels of one or more biomarkers in a sample collected from the patient; and (b) comparing the levels of the one or more biomarkers with predefined levels of the same biomarkers that correlate to a patient having aggressive prostate cancer and predefined levels of the same biomarkers that correlate to a patient not having aggressive prostate cancer, wherein a correlation to one of the predefined levels provides the diagnosis. In a specific embodiment, the one or more biomarkers may comprise cathepsin-L (CTSL), periostin, microfibrillar-associated protein 4 (MFAP4), collagen XII, neprilysin, clusterin, neutrophil gelatinase associated lipocalin (NGAL), epithelial cell activating molecule (EpCAM), prostate specific antigen (PSA), membrane metallo-endopeptidase (MME) and asporin (ASPN).

7 Claims, 66 Drawing Sheets

Table 1. Glycoproteins Overexpressed in Aggressive (AG) Prostate Tumors

| proteins | peptides[a] | AG-tumor[b] | | | | NAG-tumor[b] | | | | ratio of AG/NAG[c] |
|---|---|---|---|---|---|---|---|---|---|---|
| | | 113 | 114 | 115 | 121 | 116 | 117 | 118 | 119 | |
| microfibrillar-associated protein 4 | vDLEDFEnNTAYAk | 1.00 | 0.95 | 1.50 | 1.30 | 0.31 | 0.20 | 0.41 | 0.53 | 3.28 |
| microfibrillar-associated protein 4 | fnGSVSFFR | 1.00 | 1.56 | 1.29 | 1.70 | 0.14 | 0.34 | 0.38 | 0.87 | 3.22 |
| periostin | eVnDTLLVNELk | 1.00 | 0.57 | 1.24 | 0.54 | 0.26 | 0.17 | 0.34 | 0.52 | 2.62 |
| cathepsin L | ySVAnDTGFVDIPk | 1.00 | 0.32 | 0.96 | 1.33 | 0.38 | 0.44 | 0.78 | 0.62 | 1.85 |

[a] Lower case v, e, y, f, and k represent the iTRAQ labeled N-termini and Lys, lower case n in the nXT/S motif represents the formerly glycosylated Asp and deiminated after SPEG isolation. [b] The number showed the ratio of different channel vs 113. [c] The ratio of AG/NAG uses the average of each group.

FIG. 5

| Protein Name | Swiss-Prot | Peptide Sequence |
|---|---|---|
| Seven transmembrane helix receptor | Q8NGK5 | M.YLVAVVGN#VTILAVVK.I |
| Kallikrein 5 precursor | Q9Y337 | R.DSCQGDSGGPVVCN#GSLQ.G |
| Glandular kallikrein 1 precursor | P06870 | E.PEN#FSFPDDLQCVDLK.I |
| Procollagen C-proteinase enhancer protein precursor | Q15113 | G.QTPN#YTRPVFLCGGDVK.G |
| Glutamate decarboxylase 1 | Q9BU91 | -.MASSTPSSSATSSNAGADPN#TT.N |
| Thyroxine-binding globulin precursor | P05543 | K.TTTVQVPMMHQMEQYYHLVDMELN#CTVLQMDYSK.N |
| Alpha-1-acid glycoprotein 2 precursor | P19652 | P.ITN#ATLDR.I |
| scavenger receptor class B, member 2 | Q14108 | F.N#VTNPEEILR.G |
| Alpha-2-macroglobulin precursor | P01023 | R.GNEANYYSN#ATTDEHGLVQFSIN#TTNVMGTSLTVR.V |
| Membrane copper amine oxidase | Q16853 | K.EEEPSSSSVFNQNDPWAPTVDFSDFINN#ETIAGK.D |
| Splice isoform 1 of P24821 Tenascin precursor | P24821 | K.GFEESEPVSGSFTTALDGPSGLVTAN#ITDSEALAR.W |
| Kallikrein 13 precursor | Q9UKR3 | K.VLNTN#GTSGFLPGGYTCFPH.S |
| Presenilin-like protein 2 | Q8TCT8 | A.QEAILHASGN#GTTK.D |
| Beta-hexosaminidase beta chain precursor | P07686 | R.GLETFSQLVYQDSYGTFTIN#ESTIIDSPR.F |
| Alpha-1-antitrypsin precursor | P01009 | R.QLAHQSN#STNIFFSPVSIATAFAMLSLGTK.A |
| Splice isoform Beta-1A of P05556 Integrin beta-1 precursor | P05556 | K.SCGECIQAGPNCGWCTN#STFLQEGMPTSAR.C |
| Prolargin precursor | P51888 | R.IHYLYLQNNFITELPVESFQN#ATGLR.W |
| Alpha-galactosidase A precursor | P06280 | F.QKPN#YTEIR.Q |
| Acid phosphatase, prostate | Q96QM0 | K.VYDPLYCESVHN#FTLPSWATEDTMTK.L |
| CD44 isoform RC | O95370 | D.LN#ITCR.F |
| Splice isoform 1 of Q9NZ08 Adipocyte-derived leucine aminopeptidase precursor | Q9NZ08 | K.CFDAMEVDALN#SSHPVSTPVENPAQIR.E |
| Integrin alpha-1 | P56199 | K.EN#MTFGSTLVTNPNGGFLACGPLYAYR.C |
| Splice isoform TGN51 of O43493 Trans-Golgi network integral membrane protein 2 precursor | O43493 | K.QEEAGVRPSAGN#VSTHPSLSQRPGGSTK.S |
| Prostate stem cell antigen precursor | O43653 | K.AQVSNEDCLQVEN#CTQLGEQCWTAR.I |

FIG. 6

| Protein Name | Swiss-Prot | Peptide Sequence |
|---|---|---|
| Splice isoform A of P07585 Decorin precursor | P07585 | R.IADTN#ITSIPQGLPPSLTELHLDGNK.I |
| Splice isoform 1 of P24821 Tenascin precursor | P24821 | R.QSGVN#ATLPEENQPVVFNHVYNIK.L |
| Acid phosphatase, prostate | Q96QM0 | R.N#ETQHEPYPLMLPGCSPSCPLER.F |
| Splice isoform PSMA-1 of Q04609 Glutamate carboxypeptidase II | Q04609 | K.FLYN#FTQIPHLAGTEQNFQLAK.Q |
| Carboxypeptidase H precursor | P16870 | R.DLQGNPIAN#ATISVEGIDHDVTSAK.D |
| Kallikrein 10 precursor | O43240 | K.LLPLLMAQLWAAEAALLPQN#DTR.L |
| Polymeric-immunoglobulin receptor precursor (Poly-Ig receptor) (PIGR) [Contains: Secretory component] | P01833 | K.QIGLYPVLVIDSSGYVNPN#YTGR.I |
| Clusterin precursor | P10909 | R.QLEEFLN#QSSPFYFWMNGDR.I |
| membrane alanine aminopeptidase precursor | P15144 | K.GPSTPLPEDPNWN#VTEFHTTPK.M |
| Nidogen-2 precursor | Q14112 | K.TNIQGQVPYVPAN#FTAHISPYK.E |
| RPE-spondin | Q96J64 | R.CSGDGLDSDGN#QTLHWQAIGNPR.C |
| Integrin alpha-1 | P56199 | K.QTQVGIVQYGEN#VTHEFNLNK.Y |
| Polymeric-immunoglobulin receptor precursor (Poly-Ig receptor) (PIGR) [Contains: Secretory component] | P01833 | R.LSLLEEPGN#GTFTVILNQLTSR.D |
| Serotransferrin precursor | P02787 | R.QQQHLFGSN#VTDCSGNFCLFR.S |
| BA209J19.1.1 | Q9H1L6 | R.VN#LTTNTIAVTQTLPNAAYNNR.F |
| Splice isoform 1 of Q9UBX7 Kallikrein 11 precursor | Q9UBX7 | K.CENAYPGN#ITDTMVCASVQEGGK.D |
| Splice isoform 1 of P12111 Collagen alpha 3(VI) chain precursor | P12111 | R.QLINALQIN#NTAVGHALVLPAGR.D |
| Splice isoform A of P07585 Decorin precursor | P07585 | K.LGLSFNSISAVDN#GSLANTPHLR.E |
| CD166 antigen precursor | Q13740 | K.IIISPEEN#VTLTCTAENQLER.T |
| Laminin alpha-5 chain precursor | O15230 | R.AQQLLAN#STALEEAMLQEQQR.L |
| Alpha-2-HS-glycoprotein precursor | P02765 | K.AALAAFNAQNN#GSNFQLEEISR.A |
| Membrane copper amine oxidase | Q16853 | R.QPQPN#VSELVVGPLPHPSYMR.D |
| Putative transmembrane protein NMB precursor | Q14956 | R.VSVNTAN#VTLGPQLMEVTVYR.R |
| Acid ceramidase precursor | Q13510 | K.ILAPAYFILGGN#QSGEGCVITR.D |
| Chymase precursor | P23946 | R.SITVTLGAHN#ITEEEDTWQK.L |

FIG. 6 cont'd.

| Protein Name | Swiss-Prot | Peptide Sequence |
|---|---|---|
| Complement C3 precursor [Contains: C3a anaphylatoxin] | P01024 | K.TVLTPATNHMGN#VTFTIPANR.E |
| Apolipoprotein D precursor | P05090 | R.ADGTVNQIEGEATPVN#LTEPAK.L |
| Fibrillin 1 precursor | P35555 | R.NYYADN#QTCDGELLFN#MTK.K |
| Hypothetical protein FLJ20421 | Q9NX62 | K.QVALQTFGN#QTTIIPAGGAGYK.V |
| Splice isoform 1 of P02751 Fibronectin precursor | P02751 | K.LDAPTNLQFVN#ETDSTVLVR.W |
| Cell surface glycoprotein MUC18 precursor | P43121 | K.CGLSQSQGN#LSHVDWFSVHK.E |
| Hypothetical protein FLJ90478 | Q8NC56 | K.CIPVMEAQEYIAN#VTSSSSAK.F |
| BA209J19.1.1 | Q9H1L6 | R.SLGSGGSVSQLFSN#FTGSVDDR.G |
| Unknown |  | R.TLN#QSSDELQLSMGNAMFVK.E |
| glycoprotein 2 (zymogen granule membrane) | P55259 | R.QDLN#SSDVHSLQPQLDCGPR.E |
| CD166 antigen precursor | Q13740 | K.LGDCISEDSYPDGN#ITWYR.N |
| Dipeptidyl-peptidase II precursor | Q9UHL4 | R.ALAGLVYN#ASGSEHCYDIYR.L |
| similar to embryonic blastocoelar extracellular matrix protein precursor | Q7Z341 | K.GSSSSEPMVPPQSHHN#DSSEV.- |
| Plasma protease C1 inhibitor precursor | P05155 | R.ASSNPN#ATSSSSQDPESLQDR.G |
| Splice isoform 1 of P12111 Collagen alpha 3(VI) chain precursor | P12111 | R.VAVVQHAPSESVDN#ASMPPVK.V |
| EWI2 | Q96EW3 | R.IGPGEPLELLCN#VSGALPPAGR.H |
| Basement membrane-specific heparan sulfate proteoglycan core protein precursor | P98160 | R.SLTQGSLIVGDLAPVN#GTSQGK.F |
| Splice isoform A of Q9UL36 Zinc finger protein 236 | Q9UL36 | R.CDQCPQTFNVEFN#LTLHK.C |
| Ceruloplasmin precursor | P00450 | K.EN#LTAPGSDSAVFFEQGTTR.I |
| Integrin alpha-5 precursor | P08648 | K.EPLSDPVGTCYLSTDN#FTR.I |
| Plasma protease C1 inhibitor precursor | P05155 | R.VLSN#NSDANLELINTWVAK.N |
| Dipeptidyl peptidase IV | P27487 | R.IQN#YSVMDICDYDESSGR.W |
| biotinidase precursor | P43251 | K.NPVGLIGAEN#ATGETDPSHSK.F |
| Splice isoform OA3-323 of Q08722 Leukocyte surface antigen CD47 precursor | Q08722 | K.SDAVSHTGN#YTCEVTELTR.E |

FIG. 6 cont'd.

| Protein Name | Swiss-Prot | Peptide Sequence |
|---|---|---|
| guanine nucleotide binding protein (G protein), alpha inhibiting activity polypeptide 3 | P08754 | R.EYQLN#DSASYYLNDLDR.I |
| Costimulatory molecule | Q9BXR1 | K.QLVHSFAEGQDQGSAYAN#R.T |
| Membrane copper amine oxidase | Q16853 | R.IQMLSFAGEPLPQN#SSMAR.G |
| Vacuolar ATP synthase subunit S1 precursor | Q15904 | K.QPVSPVIHPPVSYN#DTAPR.I |
| HLA class II histocompatibility antigen, DR-1 beta chain precursor | P01912 | R.FLEYSTSECHFFN#GTER.V |
| Splice isoform 1 of P20151 Glandular kallikrein 2 precursor | P20151 | R.VPVSHSFPHPLYN#MSLLK.H |
| Alpha-2-glycoprotein 1, zinc | P25311 | K.DIVEYYN#DSN#GSHVLQGR.F |
| Hypothetical protein | Q9H670 | R.TYLVN#SSDSGSSQTESPSSK.Y |
| Dihydropyridine-sensitive L-type, calcium channel alpha-2/delta subunits precursor | P54289 | K.QSCITEQTQYFFDN#DSK.S |
| Tripeptidyl-peptidase I precursor | O14773 | K.FLSSSPHLPPSSYFN#ASGR.A |
| Tetraspanin 1 | O60635 | K.DYGSQEDFTQVWN#TTMK.G |
| Myosin heavy chain, smooth muscle isoform | P35749 | K.NMDPLNDN#VTSLLN#ASSDK.F |
| Lactotransferrin precursor (Lactoferrin) [Contains: Lactoferroxin A; Lactoferroxin B; Lactoferroxin C] | P02788 | R.TAGWNIPMGLLFN#QTGSCK.F |
| Tetraspanin 1 | O60635 | K.CCGFTN#YTDFEDSPYFK.E |
| 150 kDa oxygen-regulated protein precursor | Q9Y4L1 | K.EN#GTDTVQEEEESPAEGSK.D |
| Laminin beta-1 chain precursor | P07942 | R.VN#ASTTEPN#STVEQSALMR.D |
| Splice isoform 1 of O00584 Ribonuclease 6 precursor | O00584 | K.QDQQLQN#CTEPGEQPSPK.Q |
| scavenger receptor class B, member 2 | Q14108 | R.TMVFPVMYLN#ESVHIDK.E |
| MAC-2 binding protein precursor | Q08380 | K.EPGSN#VTMSVDAECVPMVR.D |
| Podocalyxin-like protein 1 precursor | O00592 | K.QLVLN#LTGNTLCAGGASDEK.L |
| Fibrillin 1 precursor | P35555 | K.AWGTPCEMCPAVN#TSEYK.I |
| Plasma kallikrein precursor | P03952 | K.IYPGVDFGGEELN#VTFVK.G |

FIG. 6 cont'd.

| Protein Name | Swiss-Prot | Peptide Sequence |
|---|---|---|
| monogenic, audiogenic seizure susceptibility 1 homolog | Q8TF58 | R.DSGTGLMMSVN#FSTQELR.S |
| Probable serine carboxypeptidase CPVL precursor | Q9H3G5 | R.QAIHVGN#QTFNDGTIVEK.Y |
| Splice isoform LAMP-2A of P13473 Lysosome-associated membrane glycoprotein 2 precursor | P13473 | K.VASVININPN#TTHSTGSCR.S |
| scavenger receptor class B, member 2 | Q14108 | K.CNMIN#GTDGDSFHPLITK.D |
| Histidine-rich glycoprotein precursor | P04196 | R.VIDFN#CTTSSVSSALANTK.D |
| Splice isoform 1 of Q9UBX7 Kallikrein 11 precursor | Q9UBX7 | R.TATESFPHPGFN#NSLPNK.D |
| Splice isoform PSMA-1 of Q04609 Glutamate carboxypeptidase II | Q04609 | R.GVAYINADSSIEGN#YTLR.V |
| Laminin gamma-1 chain precursor | P11047 | R.TLAGEN#QTAFEIEELNR.K |
| Polymeric-immunoglobulin receptor precursor (Poly-Ig receptor) (PIGR) [Contains: Secretory component] | P01833 | K.WN#NTGCQALPSQDEGPSK.A |
| Splice isoform 1 of P24821 Tenascin precursor | P24821 | R.LN#YSLPTGQWVGVQLPR.N |
| Prostaglandin-H2 D-isomerase precursor | P41222 | K.SVVAPATDGGLN#LTSTFLR.K |
| Dihydropyridine-sensitive L-type, calcium channel alpha-2/delta subunits precursor | P54289 | R.SLDNDNYVFTAPYFN#K.S |
| Hypothetical protein | Q86V91 | K.QDILN#NSLTTLSQDITK.V |
| Splice isoform 1 of Q92859 Neogenin precursor | Q92859 | R.TLSDVPSAAPQN#LSLEVR.N |
| Fibrinogen beta chain precursor [Contains: Fibrinopeptide B] | P02675 | R.GTAGNALMDGASQLMGEN#R.T |
| Ceruloplasmin precursor | P00450 | K.EHEGAIYPDN#TTDFQR.A |
| Laminin beta-2 chain precursor | P55268 | R.N#TSAASTAQLVEATEELR.R |
| Lysosomal alpha-glucosidase precursor | P10253 | K.LEN#LSSSEMGYTATLTR.T |
| Alpha-1-acid glycoprotein 2 precursor | P19652 | R.QNQCFYN#SSYLNVQR.E |
| Tumor endothelial marker 7-related precursor | Q96PD9 | R.VN#LSFDFPFYGHFLR.E |

FIG. 6 cont'd.

| Protein Name | Swiss-Prot | Peptide Sequence |
|---|---|---|
| Alpha-1-acid glycoprotein 1 precursor | P02763 | R.QDQCIYN#TTYLNVQR.E |
| scavenger receptor class B, member 2 | Q14108 | K.ANIQFGDN#GTTISAVSNK.A |
| Cartilage oligomeric matrix protein precursor | P49747 | R.CN#DTIPEDYETHQLR.Q |
| Splice isoform 1 of Q16563 Pantophysin | Q16563 | K.GQTEIQVNCPPAVTEN#K.T |
| O-acetyltransferase | Q96PB1 | K.IDAYNEAAVSILN#SSTR.N |
| Intercellular adhesion molecule-2 precursor | P13598 | K.AAPAPQEATATFN#STADR.E |
| Splice isoform PSMA-1 of Q04609 Glutamate carboxypeptidase II | Q04609 | K.VPYNVGPGFTGN#FSTQK.V |
| BA209J19.1.1 | Q9H1L6 | K.LN#DTTLQVLNTWYTK.Q |
| Antithrombin-III precursor | P01008 | K.LGACN#DTLQQLMEVFK.F |
| Hypothetical protein | Q8WUM6 | R.NPCTSEQN#CTSPFSYK.N |
| Prostate-specific membrane antigen-like protein | Q9HBA9 | K.VSYNVGPGFTGN#FSTQK.V |
| Laminin beta-2 chain precursor | P55268 | R.AN#TSALAVPSPVSNSASAR.H |
| Tumor-associated calcium signal transducer 1 | Q96C47 | K.QCN#GTSTCWCVNTAGVR.R |
| Carboxypeptidase D precursor | O75976 | K.DLDTDFTNN#ASQPETK.A |
| Haptoglobin precursor | P00738 | K.VVLHPN#YSQVDIGLIK.L |
| Lysosome-associated membrane glycoprotein 1 precursor | P11279 | K.N#MTFDLPSDATVVLN#R.S |
| Cadherin-13 precursor | P55290 | K.IN#NTHALVSLLQNLNK.A |
| Endoplasmin precursor | P14625 | R.EEEAIQLDGLN#ASQIR.E |
| EMILIN 1 precursor | Q9Y6C2 | R.LEQLGGLLAN#VSGELGGR.L |
| Hypothetical protein | Q96C67 | K.AMN#ASAN#ITSDGVEVLGK.M |
| Complement C4 precursor [Contains: C4a anaphylatoxin] | P01028 | R.FSDGLESN#SSTQFEVK.K |
| Splice isoform 2C2A' of P12110 Collagen alpha 2(VI) chain precursor | P12110 | R.GTFTDCALAN#MTEQIR.Q |
| Kallikrein 5 precursor | Q9Y337 | K.DVRPIN#VSSHCPSAGTK.C |
| FLJ00343 protein | Q96C61 | R.VAN#PSGN#LTETYVQDR.G |
| Splice isoform B of P23142 Fibulin-1 precursor | P23142 | R.CATPHGDN#ASLEATFVK.R |
| Alpha-1-antitrypsin precursor | P01009 | K.YLGN#ATAIFFLPDEGK.L |

FIG. 6 cont'd.

| Protein Name | Swiss-Prot | Peptide Sequence |
|---|---|---|
| Metalloproteinase inhibitor 1 precursor | P01033 | K.FVGTPEVN#QTTLYQR.Y |
| Cleft lip and palate associated transmembrane protein 1 | Q9BSS5 | K.DYYPIN#ESLASLPLR.V |
| Laminin alpha-5 chain precursor | O15230 | R.LN#TTGVSAGCTADLLVGR.A |
| Integrin alpha-1 | P56199 | K.LDLPVN#TSIPN#VTEVK.E |
| Protein FAM3D precursor | Q96BQ1 | R.GLNIALVN#GTTGAVLGQK.A |
| Carboxypeptidase B-like protein | Q9P2Y6 | K.QVHFFVN#ASDVDNVK.A |
| similar to collagen type XIV | Q05707 | R.SFMVN#WTHAPGNVEK.Y |
| Integral membrane protein 2B (Transmembrane protein BRI) [Contains: ABri/ADan amyloid peptide] | Q9Y287 | K.CYVIPLN#TSIVMPPR.N |
| Kallikrein 6 precursor | Q92876 | R.DCSAN#TTSCHILGWGK.T |
| laminin alpha 2 subunit precursor | P24043 | R.YMQN#LTVEQPIEVK.K |
| CD59 glycoprotein precursor | P13987 | K.TAVN#CSSDFDACLITK.A |
| Hypothetical protein FLJ90516 | Q8NC34 | R.TALFPDLLAQGN#ASLR.L |
| Apolipoprotein B-100 precursor (Apo B-100) [Contains: Apolipoprotein B-48 (Apo B-48)] | P04114 | R.FN#SSYLQGTNQITGR.Y |
| Clusterin precursor | P10909 | R.LAN#LTQGEDQYYLR.V |
| Laminin gamma-1 chain precursor | P11047 | K.TAN#DTSTEAYNLLLR.T |
| Hemopexin precursor | P02790 | K.ALPQPQN#VTSLLGCTH.- |
| Splice isoform 2A of Q02487 Desmocollin 2A/2B precursor | Q02487 | K.NGIYN#ITVLASDQGGR.T |
| Protein-lysine 6-oxidase precursor | P28300 | R.DPGAAVPGAAN#ASAQQPR.T |
| hypothetical protein DKFZp313G1735 | Q8N3Q8 | K.QSIGQN#YSNVIANLR.W |
| Lutheran blood group glycoprotein precursor | P50895 | R.TQN#FTLLVQGSPELK.T |
| Dopamine beta-monooxygenase precursor | P09172 | R.SLEAIN#GSGLQMGLQR.V |
| MAC-2 binding protein precursor | Q08380 | R.TVIRPFYLTN#SSGVD.- |
| EMILIN 1 precursor | Q9Y6C2 | R.ETN#TTSQMQAALLEK.L |
| Alpha-2-HS-glycoprotein precursor | P02765 | K.VCQDCPLLAPLN#DTR.V |
| FLJ00343 protein | Q96C61 | K.VTAQGPGLEPSGNIAN#K.T |

FIG. 6 cont'd.

| Protein Name | Swiss-Prot | Peptide Sequence |
|---|---|---|
| Splice isoform Short of Q99715 Collagen alpha 1(XII) chain precursor | Q99715 | R.NLQVYN#ATSNSLTVK.W |
| Biglycan precursor | P21810 | K.LLQVVYLHSNN#ITK.V |
| apolipoprotein F | Q13790 | R.QGGVN#ATQVLIQHLR.G |
| Splice isoform 1 of Q92932 Receptor-type protein-tyrosine phosphatase N2 precursor | Q92932 | K.VSANVQN#VTTEDVEK.A |
| Blood plasma glutamate carboxypeptidase precursor | Q9UNM8 | K.IVVYNQPYIN#YSR.T |
| Angiotensin-converting enzyme, somatic isoform precursor | P12821 | R.VTN#DTESDINYLLK.M |
| similar to hypothetical protein 6720478C22 | | R.TLLN#ASCDNMLMGIK.S |
| similar to Peroxidasin CG12002-PA | Q92626 | R.QGEHLSN#STSAFSTR.S |
| Fibrillin 1 precursor | P35555 | R.VLPVN#VTDYCQLVR.Y |
| Integrin alpha-V precursor | P06756 | K.AN#TTQPGIVEGGQVLK.C |
| Integrin alpha-5 precursor | P08648 | R.VTGLN#CTTNHPINPK.G |
| Desmoglein 2 precursor | Q14126 | K.IN#ATDADEPNTLNSK.I |
| Cation-dependent mannose-6-phosphate receptor precursor | P20645 | R.EAGN#HTSGAGLVQIN#K.S |
| solute carrier family 39 (zinc transporter), member 6 | Q8IXR3 | R.NTNENPQECFN#ASK.L |
| Transcobalamin I precursor | P20061 | K.MN#DTIFGFTMEER.S |
| Beta-1,3-N-acetylgalactosaminyltransferase | Q8TDY1 | R.QDFLDTYNN#LTLK.T |
| Glutaminyl-peptide cyclotransferase precursor | Q16769 | K.NYHQPAILN#SSALR.Q |
| Laminin gamma-1 chain precursor | P11047 | R.CDQCEENYFYN#R.S |
| Splice isoform Short of Q99715 Collagen alpha 1(XII) chain precursor | Q99715 | K.EAGN#ITTDGYEILGK.L |
| Integrin-like protein | Q8WWJ8 | K.LTN#NSNQFQTEVGK.Q |
| Hypothetical protein KIAA0315 | O15031 | K.SCVAVTSAQPQN#MSR.R |
| Biglycan precursor | P21810 | R.MIEN#GSLSFLPTLR.E |
| Low density lipoprotein receptor related protein-deleted in tumor | Q8WY28 | R.VGMDGTN#QSVVIETK.I |
| Lysosomal alpha-glucosidase precursor | P10253 | R.GVFITN#ETGQPLIGK.V |

FIG. 6 cont'd.

| Protein Name | Swiss-Prot | Peptide Sequence |
|---|---|---|
| Splice isoform Sap-mu-0 of P07602 Proactivator polypeptide precursor [Contains: Saposin A (Protein A); Saposin B (Sphingolipid activator protein 1) (SAP-1) (Cerebroside sulfate activator) (CSAct) (Dispersin) (Sulfatide/GM1 activator); Saposin C (Co-beta-glucosidase) (A1 activator) (Glucosylceramidase activator) (Sphingolipid activator protein 2) (SAP-2); Saposin D (Protein C) (Component C)] | P07602 | R.TN#STFVQALVEHVK.E |
| DJ68D18.2.5 (CD44 antigen | Q9H5A6 | K.AFN#STLPTMAQMEK.A |
| CTL2 gene | Q8IWA5 | K.TCNPETFPSSN#ESR.Q |
| Fibroleukin precursor | Q14314 | R.LHVGNYN#GTAGDALR.F |
| Laminin gamma-1 chain precursor | P11047 | K.IPAIN#QTITEANEK.T |
| EMILIN 3 precursor | Q9H8L6 | R.QVEELQVN#HTALR.E |
| Splice isoform Long of P36980 Complement factor H-related protein 2 precursor | P36980 | R.LQNNENN#ISCVER.G |
| EMILIN 1 precursor | Q9Y6C2 | R.LGALN#SSLQLLEDR.L |
| Apolipoprotein B-100 precursor (Apo B-100) [Contains: Apolipoprotein B-48 (Apo B-48)] | P04114 | K.YDFN#SSMLYSTAK.G |
| Cathepsin L precursor | P07711 | K.YSVAN#DTGFVDIPK.Q |
| Stromal cell-derived receptor-1 alpha | Q9Y639 | K.ENGMPMDIVN#TSGR.F |
| 150 kDa oxygen-regulated protein precursor | Q9Y4L1 | R.AEPPLN#ASASDQGEK.V |
| Asporin precursor | Q9BXN1 | K.ITDIEN#GSLANIPR.V |
| Splice isoform 1 of P08603 Complement factor H precursor | P08603 | R.ISEEN#ETTCYMGK.W |
| M130 antigen cytoplasmic variant 2 precursor | Q07900 | K.EDAAVN#CTDISVQK.T |
| Splice isoform Lamin A of P02545 Lamin A/C | P02545 | R.TALIN#STGEEVAMR.K |
| Splice isoform V0 of P13611 Versican core protein precursor | P13611 | R.FEN#QTGFPPPDSR.F |
| glycoprotein 2 (zymogen granule membrane) | P55259 | R.DPN#CSSILQTEER.N |

FIG. 6 cont'd.

| Protein Name | Swiss-Prot | Peptide Sequence |
|---|---|---|
| Melanoma-associated chondroitin sulfate proteoglycan | Q92675 | R.LDPTVLDAGELAN#R.T |
| Splice isoform Beta-1A of P05556 Integrin beta-1 precursor | P05556 | K.CHEGN#GTFECGACR.C |
| Integrin alpha-5 precursor | P08648 | K.NLN#NSQSDVVSFR.L |
| Inter-alpha-trypsin inhibitor heavy chain H2 precursor | P19823 | K.GAFISN#FSMTVDGK.T |
| Biliary glycoprotein | Q13857 | K.LSQGN#TTLSINPVK.R |
| solute carrier family 39 (zinc transporter), member 6 | Q8IXR3 | R.YGEN#NSLSVEGFR.K |
| Acid ceramidase precursor | Q13510 | R.TVLEN#STSYEEAK.N |
| Apolipoprotein D precursor | P05090 | R.CIQAN#YSLMENGK.I |
| Splice isoform 1 of P24821 Tenascin precursor | P24821 | K.VEAAQN#LTLPGSLR.A |
| Beta-2-glycoprotein I precursor | P02749 | R.VYKPSAGN#NSLYR.D |
| Sel-1 homolog precursor | Q9UBV2 | R.EASIVGEN#ETYPR.A |
| Integrin alpha-1 | P56199 | R.SEN#ASLVLSSSNQK.R |
| Di-N-acetylchitobiase precursor | Q01459 | K.QIN#SSISGNLWDK.D |
| Haptoglobin precursor | P00738 | K.NLFLN#HSEN#ATAK.D |
| Splice isoform 1 of Q8NBK3 Sulfatase modifying factor 1 precursor | Q8NBK3 | K.FVN#STGYLTEAEK.F |
| Complement C2 precursor | P06681 | K.QSVPAHFVALN#GSK.L |
| Carboxypeptidase H precursor | P16870 | K.GN#ETIVNLIHSTR.I |
| Hypothetical protein | Q8N382 | R.LAVTN#TTMTGTVLK.M |
| Splice isoform 1 of Q12860 Contactin precursor | Q12860 | K.AN#STGTLVITDPTR.I |
| Kallikrein 5 precursor | Q9Y337 | K.VLQCLN#ISVLSQK.R |
| Skeletal muscle LIM-protein 1 | Q13642 | K.CLHPLAN#ETFVAK.D |
| Hypothetical protein FLJ11273 | Q8N4L0 | R.LNN#ITIIGPLDMK.Q |
| Plasma kallikrein precursor | P03952 | R.IYSGILN#LSDITK.D |
| Splice isoform A of O60245 Protocadherin 7 precursor | O60245 | K.IDN#LTGELSTSER.R |
| Desmoglein 2 precursor | Q14126 | K.DTGELN#VTSILDR.E |
| Splice isoform HMW of P01042 Kininogen precursor (Alpha-2-thiol proteinase inhibitor) [Contains: Bradykinin] | P01042 | K.LNAENN#ATFYFK.I |
| Laminin alpha-5 chain precursor | O15230 | R.LN#ASIADLQSQLR.S |

FIG. 6 cont'd.

| Protein Name | Swiss-Prot | Peptide Sequence |
|---|---|---|
| Leucine-rich alpha-2-glycoprotein precursor | P02750 | K.LPPGLLAN#FTLLR.T |
| Angiotensin-converting enzyme, somatic isoform precursor | P12821 | R.QQYNALLSN#MSR.I |
| Adipocyte plasma membrane-associated protein | Q9HDC9 | R.AGPN#GTLFVADAYK.G |
| laminin alpha 2 subunit precursor | P24043 | K.QEGILYVDGASN#R.T |
| Serotransferrin precursor | P02787 | K.CGLVPVLAENYN#K.S |
| Splice isoform Short of Q13459 Myosin IXb | Q13459 | K.LGFSSPYEGVLN#K.S |
| Transferrin receptor protein 1 | P02786 | K.QNNGAFN#ETLFR.N |
| Similar to RIKEN cDNA 1300012G16 | Q8NHP8 | R.SDLNPAN#GSYPFK.A |
| Human full-length cDNA 5-PRIME end of clone CS0DM009YC13 of fetal liver of Homo sapiens | P29622 | K.FLN#DTMAVYEAK.L |
| Splice isoform A of P12314 High affinity immunoglobulin gamma Fc receptor I precursor | P12314 | R.ITSASVN#DSGEYR.C |
| Polymeric-immunoglobulin receptor precursor (Poly-Ig receptor) (PIGR) [Contains: Secretory component] | P01833 | K.VPGN#VTAVLGETLK.V |
| Splice isoform OSF-2OS of Q15063 Osteoblast specific factor 2 precursor | Q8IZF9 | K.EVN#DTLLVNELK.S |
| Laminin alpha-5 chain precursor | O15230 | R.DN#ATLQATLHAAR.D |
| Splice isoform 1 of Q12884 Seprase | Q12884 | K.SVN#ASNYGLSPDR.Q |
| HLA class II histocompatibility antigen, DRB1-4 beta chain precursor | P13760 | K.HECHFFN#GTER.V |
| Splice isoform 1 of Q02083 N-acylsphingosine amidohydrolase-like precursor | Q02083 | R.FN#VSLDSVPELR.W |
| Bactericidal/permeability-increasing protein-like 1 precursor | Q8N4F0 | R.SDDNLLN#TSALGR.L |
| Nidogen-2 precursor | Q14112 | R.IHQN#ITYQVCR.H |
| Splice isoform 2C2A' of P12110 Collagen alpha 2(VI) chain precursor | P12110 | R.N#MTLFSDLVAEK.F |

FIG. 6 cont'd.

| Protein Name | Swiss-Prot | Peptide Sequence |
|---|---|---|
| Splice isoform 1 of P08603 Complement factor H precursor | P08603 | K.MDGASN#VTCINSR.W |
| Integrin alpha-1 | P56199 | R.YN#HTGQVIIYR.M |
| CD63 antigen | P08962 | K.CCGAAN#YTDWEK.I |
| Urokinase receptor-associated protein UPARAP | Q9UBG0 | R.VTPACN#TSLPAQR.W |
| Splice isoform HMW of P01042 Kininogen precursor (Alpha-2-thiol proteinase inhibitor) [Contains: Bradykinin] | P01042 | R.ITYSIVQTN#CSK.E |
| Myosin light chain 1, slow-twitch muscle A isoform | P14649 | R.ALGQN#PTNAEVLK.V |
| maba1 | Q8N1G3 | K.MSVCTDN#VTDLR.I |
| MAC-2 binding protein precursor | Q08380 | R.ALGFEN#ATQALGR.A |
| Hemopexin precursor | P02790 | R.SWPAVGN#CSSALR.W |
| Low-density lipoprotein receptor-related protein 1 precursor | Q07954 | R.FN#STEYQVVTR.V |
| Procollagen-lysine,2-oxoglutarate 5-dioxygenase 3 precursor | O60568 | K.EQYIHEN#YSR.A |
| Lysosomal acid phosphatase precursor | P11117 | R.QTPEYQN#ESSR.N |
| Complement component C8 alpha chain precursor | P07357 | R.GGSSGWSGGLAQN#R.S |
| O-acetyltransferase | Q96PB1 | K.MN#ITSIAPLLEK.L |
| Unknown | | K.SECHFFN#GTER.V |
| Transmembrane 4 superfamily, member 3 | P19075 | R.IVN#ETLYENTK.L |
| Splice isoform 1 of O75882 Attractin precursor | O75882 | K.IDSTGN#VTNELR.V |
| Splice isoform H17 of P05164 Myeloperoxidase precursor | P05164 | R.SCPACPGSN#ITIR.N |
| Lymphocyte antigen | Q30161 | R.QECYAFN#GTQR.F |
| membrane metallo-endopeptidase | P08473 | K.EIAN#ATAKPEDR.N |
| Membrane copper amine oxidase | Q16853 | R.YLYLASN#HSNK.W |
| similar to agrin precursor | Q96IC1 | K.NELMLN#SSLMR.I |
| Dipeptidyl-peptidase I precursor | P53634 | R.DVN#CSVMGPQEK.K |

FIG. 6 cont'd.

| Protein Name | Swiss-Prot | Peptide Sequence |
|---|---|---|
| Low-density lipoprotein receptor-related protein 1 precursor | Q07954 | R.LN#GTDPIVAADSK.R |
| Hypothetical protein NT2RP3000266 | Q8NBJ4 | K.AVLVNN#ITTGER.L |
| FLJ00343 protein | Q96C61 | K.LPQLPITN#FSR.D |
| membrane alanine aminopeptidase precursor | P15144 | K.AEFN#ITLIHPK.D |
| Beta-sarcoglycan | Q16585 | R.ITSN#ATSDLNIK.V |
| MAC-2 binding protein precursor | Q08380 | K.AAIPSALDTN#SSK.S |
| Splice isoform Long of P08236 Beta-glucuronidase precursor | P08236 | K.VVAN#GTGTQGQLK.V |
| Sad1/unc-84-like protein 2 | Q9UH99 | K.ALSPN#STISSAPK.D |
| Splice isoform 1 of P18206 Vinculin | P18206 | K.AVAGN#ISDPGLQK.S |
| Splice isoform 1 of Q9UBX7 Kallikrein 11 precursor | Q9UBX7 | R.CAN#ITIIEHQK.C |
| 5'-nucleotidase precursor | P21589 | K.LDN#YSTQELGK.T |
| Lymphatic endothelium-specific hyaluronan receptor LYVE-1 | Q9Y5Y7 | K.ANQQLN#FTEAK.E |
| Fibromodulin precursor | Q06828 | R.LYLDHNN#LTR.M |
| Splice isoform OA3-323 of Q08722 Leukocyte surface antigen CD47 precursor | Q08722 | R.DIYTFDGALN#K.S |
| Similar to I factor | Q8WW88 | K.FLNN#GTCTAEGK.F |
| Collagen alpha 1(VI) chain precursor | P12109 | R.N#FTAADWGQSR.D |
| Low-density lipoprotein receptor-related protein 1 precursor | Q07954 | R.IETILLN#GTDR.K |
| similar to RIKEN cDNA 2010200I23 | | R.VN#ITYNYPVR.A |
| Transmembrane protease, serine 2 precursor | O15393 | R.CIACGVNLN#SSR.Q |
| immunoglobulin J chain | P01591 | R.EN#ISDPTSPLR.T |
| Myosin regulatory light chain | O14950 | K.LN#GTDPEDVIR.N |
| Integrin alpha-1 | P56199 | K.VYVYALN#QTR.F |
| Carboxypeptidase D precursor | O75976 | R.FANEYPN#ITR.L |
| Laminin gamma-1 chain precursor | P11047 | R.VN#NTLSSQISR.L |
| Splice isoform Short of Q99715 Collagen alpha 1(XII) chain precursor | Q99715 | K.MLEAYN#LTEK.N |

FIG. 6 cont'd.

| Protein Name | Swiss-Prot | Peptide Sequence |
|---|---|---|
| Dipeptidyl peptidase IV | P27487 | K.LDFIILN#ETK.F |
| Hypothetical protein KIAA0960 | O43376 | R.CPN#SSALQEVR.S |
| Afamin precursor | P43652 | R.DIENFN#STQK.F |
| membrane metallo-endopeptidase | P08473 | R.SCIN#ESAIDSR.G |
| 150 kDa oxygen-regulated protein precursor | Q9Y4L1 | R.VFGSQN#LTTVK.L |
| Complement C2 precursor | P06681 | K.TMFPN#LTDVR.E |
| Beta-2-glycoprotein I precursor | P02749 | K.LGN#WSAMPSCK.A |
| ASH1 | Q9NR48 | R.EGATAN#VSEGEK.K |
| Factor VII active site mutant immunoconjugate | Q96PQ8 | R.EEQYN#STYR.V |
| membrane alanine aminopeptidase precursor | P15144 | K.LN#YTLSQGHR.V |
| Beta-galactosidase precursor | P16278 | R.NNVITLN#ITGK.A |
| Neutrophil gelatinase-associated lipocalin precursor | P80188 | K.SYN#VTSVLFR.K |
| Lysosomal acid phosphatase precursor | P11117 | R.YEQLQN#ETR.Q |
| Transmembrane 9 superfamily protein member 3 precursor | Q9HD45 | R.IVDVN#LTSEGK.V |
| Ig gamma-4 chain C region | P01861 | R.EEQFN#STYR.V |
| Human full-length cDNA clone CS0DI019YF20 of placenta of Homo sapiens | Q86TT2 | R.EEQYN#STFR.V |
| Lysosomal alpha-glucosidase precursor | P10253 | R.N#NTIVNELVR.V |
| FLJ00385 protein | Q8NF17 | R.EEQFN#STFR.V |
| Neuroserpin precursor | Q99574 | K.DAN#LTGLSDNK.E |
| CD63 antigen | P08962 | K.NN#HTASILDR.M |
| Integrin alpha-1 | P56199 | R.N#TTFNVESTK.K |
| Follistatin-related protein 1 precursor | Q12841 | K.GSN#YSEILDK.Y |
| biotinidase precursor | P43251 | R.FN#DTEVLQR.L |
| Splice isoform LAMP-2A of P13473 Lysosome-associated membrane glycoprotein 2 precursor | P13473 | R.VQPFN#VTQGK.Y |
| Beta-hexosaminidase alpha chain precursor | P06865 | K.SAEGTFFIN#K.T |
| Cathepsin D precursor | P07339 | K.GSLSYLN#VTR.K |

FIG. 6 cont'd.

| Protein Name | Swiss-Prot | Peptide Sequence |
|---|---|---|
| Complement C4 precursor [Contains: C4a anaphylatoxin] | P01028 | R.GLN#VTLSSTGR.N |
| Transmembrane 4 superfamily, member 6 | O43657 | K.QYN#STGDYR.S |
| laminin alpha 2 subunit precursor | P24043 | K.LSAIPN#DTAAK.L |
| similar to Prostaglandin F2 receptor negative regulator precursor (Prostaglandin F2-alpha receptor regulatory protein) (Prostaglandin F2-alpha receptor associated protein) (CD9 partner 1) (CD9P-1) | Q9P2B2 | K.LEN#WTDASR.V |
| vimentin | P08670 | R.QDVDN#ASLAR.L |
| AD-017 protein | Q9P0I5 | R.QN#ITNQLEK.W |
| Low-density lipoprotein receptor-related protein 1 precursor | Q07954 | K.DN#ATDSVPLR.T |
| TSLC1-like 2 | Q8NFZ8 | R.QTLFFN#GTR.A |
| Splice isoform LAMP-2A of P13473 Lysosome-associated membrane glycoprotein 2 precursor | P13473 | K.WQMN#FTVR.Y |
| Alpha-2-glycoprotein 1, zinc | P25311 | R.FGCEIENN#R.S |
| Mucin 2 precursor | Q02817 | K.YN#NTVEIVK.V |
| membrane alanine aminopeptidase precursor | P15144 | R.N#ATLVNEADK.L |
| Splice isoform Beta-1A of P05556 Integrin beta-1 precursor | P05556 | K.NGVN#GTGENGR.K |
| Procollagen-lysine,2-oxoglutarate 5-dioxygenase 2 precursor | O00469 | R.YN#CSIESPR.K |
| Fibrillin 2 precursor | P35556 | R.N#CTDIDECR.I |
| Hypothetical protein FLJ21551 | Q9H717 | K.QVIQN#VTHK.D |
| similar to RIKEN cDNA 2010200I23 | | R.QGN#YSAGLPR.G |
| Tissue factor precursor | P13726 | K.VN#VTVEDER.T |
| Microfibril-associated glycoprotein 4 precursor | P55083 | R.FN#GSVSFFR.G |
| CTL2 gene | Q8IWA5 | K.N#ITDLVEGAK.K |
| Hypothetical protein | Q8N348 | R.GFLN#FTLAR.A |

FIG. 6 cont'd.

| Protein Name | Swiss-Prot | Peptide Sequence |
|---|---|---|
| Splice isoform Vascular of P49961 Ectonucleoside triphosphate diphosphohydrolase 1 | P49961 | K.VVN#VSDLYK.T |
| Laminin gamma-1 chain precursor | P11047 | K.LLNN#LTSIK.I |
| Fibroleukin precursor | Q14314 | R.LDGSTN#FTR.T |
| Ceroid-lipofuscinosis neuronal protein 5 | O75503 | K.NIETN#YTR.I |
| Hypothetical protein DKFZp686C02218 | Q7Z374 | K.TPLTAN#ITK.S |
| Splice isoform 1 of P24821 Tenascin precursor | P24821 | R.N#TTSYVLR.G |
| Hypothetical protein | Q9Y4J9 | K.LN#VSDLYK.L |
| Clusterin precursor | P10909 | K.EDALN#ETR.E |
| Splice isoform 1 of P12111 Collagen alpha 3(VI) chain precursor | P12111 | K.QN#LTVTDR.V |
| Mimecan precursor | P20774 | K.AN#DTSYIR.D |
| similar to hypothetical protein | Q9UF56 | R.N#LSSLDLR.H |
| Vitronectin precursor (Serum spreading factor) (S-protein) (V75) [Contains: Vitronectin V65 subunit; Vitronectin V10 subunit; Somatomedin B] | P04004 | K.N#GSLFAFR.G |
| Splice isoform PSMA-1 of Q04609 Glutamate carboxypeptidase II | Q04609 | K.N#FTEIASK.F |
| Plasma protease C1 inhibitor precursor | P05155 | R.DTFVN#ASR.T |
| Golgi apparatus protein 1 precursor | Q92896 | K.LN#LTTDPK.F |
| Acid phosphatase, prostate | Q96QM0 | K.FLN#ESYK.H |
| ADAM 10 precursor | O14672 | R.IN#TTADEK.D |
| Prostate-specific membrane antigen-like protein | Q9HBA9 | K.IYN#ISMK.H |
| Afamin precursor | P43652 | K.FN#ETTEK.S |
| 47 kDa heat shock protein precursor | P29043 | R.SLSN#STAR.N |
| BA209J19.1.1 | Q9H1L6 | K.LLN#LTVR.I |
| Splice isoform 2A of Q02487 Desmocollin 2A/2B precursor | Q02487 | R.AN#YTILK.G |

FIG. 6 cont'd.

| Protein Name | Swiss-Prot | Peptide Sequence |
|---|---|---|
| Basement membrane-specific heparan sulfate proteoglycan core protein precursor | P98160 | R.ALVN#FTR.S |
| Alpha-1-acid glycoprotein 1 precursor | P02763 | R.EN#GTISR.Y |
| Splice isoform LAMP-2A of P13473 Lysosome-associated membrane glycoprotein 2 precursor | P13473 | R.LN#SSTIK.Y |
| EMILIN 1 precursor | Q9Y6C2 | R.LN#LTAAR.L |
| alpha-1-antichymotrypsin, precursor | P01011 | K.LINDYVKN#GTR.G |
| Prostate specific antigen precursor | P07288 | R.N#KSVILLGR.H |

FIG. 6 cont'd.

| Protein Name | Protein Accessions | Peptides | Modifications | Charge | m/z [Da] | MH+ [Da] | ΔM [ppm] | RT [min] | 114/113 | 115/113 | 116/113 | 117/113 | 118/113 | 119/113 | 121/113 |
|---|---|---|---|---|---|---|---|---|---|---|---|---|---|---|---|
| cathepsin L [Homo sapiens] | gi3929737 | ySVAnDTGFVDIPk | N-Term(iTRAQ8plex), N5(Deamidated); K14(iTRAQ8plex) | 3 | 712.38525 | 2135.14121 | -3.23 | 94.18 | 0.824 | 0.956 | 0.377 | 0.443 | 0.784 | 0.618 | 1.332 |
| Chain A, Crystal Structure Of The C2 Fragment Of Streptococcal Protein G In Complex With The Fc Domain Of Human Igg | gi1065199 | eqQYnSTYR | N-Term(iTRAQ8plex), Q2(Deamidated); N5(Deamidated) | 3 | 498.90378 | 1494.69678 | -3.09 | 47.82 | 1.360 | 1.209 | 0.758 | 0.814 | 1.413 | 1.579 | 1.141 |
| PREDICTED: CD63 molecule isoform 1 [Macaca mulatta] | gi109097131 | nnHTASILDR | N-Term(iTRAQ8plex), N1(Deamidated); N2(Deamidated) | 2 | 723.87830 | 1446.74932 | 0.19 | 61.29 | 0.981 | 0.931 | 1.461 | 2.661 | 3.034 | 0.650 | 1.282 |
| lysosome-associated membrane protein 2 | gi1094569 | lnSSTTk | N-Term(iTRAQ8plex), N2(Deamidated); K7(iTRAQ8plex) | 2 | 686.41791 | 1371.82854 | -1.33 | 62.51 | 0.806 | 0.337 | 2.319 | 0.800 | 1.360 | 0.360 | 0.477 |

FIG. 7

| Protein Name | Protein Accessions | Peptides | Modifications | Charge | m/z [Da] | MH+ [Da] | ΔM [ppm] | RT [min] | 114/113 | 115/113 | 116/113 | 117/113 | 118/113 | 119/113 | 121/113 |
|---|---|---|---|---|---|---|---|---|---|---|---|---|---|---|---|
| lysosome-associated membrane protein 2 | gi|1094569 | vQPFnVTQGk | N-Term(iTRAQ8plex), N5(Deamidated), K10(iTRAQ8plex) | 2 | 863.99768 | 1726.98808 | -3.90 | 84.75 | 1.323 | 0.624 | 3.095 | 1.661 | 2.668 | 0.653 | 1.194 |
| Biotinidase precursor (Biotinase) | gi|168695 | fnDTEVLQR | N-Term(iTRAQ8plex), N2(Deamidated) | 2 | 713.87793 | 1426.74858 | 0.42 | 85.39 | 1.120 | 0.800 | 0.748 | 0.860 | 0.965 | 1.266 | 0.807 |
| acid alpha-glucosidase preproprotein [Homo sapiens] | gi|119393891 | gVFITnETGQPLIGk | N-Term(iTRAQ8plex), N6(Deamidated), K15(iTRAQ8plex) | 3 | 728.42102 | 2183.24851 | -2.17 | 94.09 | 0.895 | 0.625 | 0.698 | 0.762 | 0.846 | 0.727 | 0.847 |
| acid alpha-glucosidase preproprotein [Homo sapiens] | gi|119393891 | IEnLSSSEmGYTATLTR | N-Term(iTRAQ8plex), N3(Deamidated), M9(Oxidation) | 3 | 732.03253 | 2194.08304 | -0.95 | 95.21 | 0.841 | 0.477 | 0.457 | 0.552 | 1.492 | 2.490 | 1.029 |
| acid alpha-glucosidase preproprotein [Homo sapiens] | gi|119393891 | nNTIVNELVR | N-Term(iTRAQ8plex), N1(Deamidated) | 2 | 738.91858 | 1476.82988 | -1.70 | 90.69 | 0.474 | 0.239 | 0.255 | 0.116 | 0.311 | 0.311 | 0.314 |

FIG. 7 cont'd.

| Protein Name | Protein Accessions | Peptides | Modifications | Charge | m/z [Da] | MH+ [Da] | ΔM [ppm] | RT [min] | 114/113 | 115/113 | 116/113 | 117/113 | 118/113 | 119/113 | 121/113 |
|---|---|---|---|---|---|---|---|---|---|---|---|---|---|---|---|
| Chain A, Structure Of Human Neutral Endopeptidase Complexed With Phosphoramidon | gi12084341 | scInESAIDSR | N-Term(iTRAQ8plex), C2(Carbamidomethyl), N4(Deamidated) | 2 | 778.87817 | 1556.74907 | -2.41 | 63.31 | 0.580 | 0.169 | 0.690 | 3.057 | 2.068 | 0.480 | 0.273 |
| Laminin subunit gamma-1 precursor (Laminin B2 chain) | gi126369 | iPAInQTITEANEk | N-Term(iTRAQ8plex), N5(Deamidated), K14(iTRAQ8plex) | 3 | 717.73785 | 2151.19901 | -5.93 | 94.14 | 0.671 | 0.520 | 0.363 | 0.569 | 0.599 | 0.588 | 0.658 |
| Laminin subunit gamma-1 precursor (Laminin B2 chain) | gi126369 | ILNnLTSIk | N-Term(iTRAQ8plex), N4(Deamidated), K9(iTRAQ8plex) | 3 | 542.33923 | 1625.00315 | -3.85 | 97.17 | 0.569 | 0.424 | 0.191 | 0.664 | 0.461 | 0.512 | 0.461 |
| Laminin subunit gamma-1 precursor (Laminin B2 chain) | gi126369 | tAnDTSTEAYNLLLR | N-Term(iTRAQ8plex), N3(Deamidated) | 2 | 994.01373 | 1987.02019 | -4.23 | 95.33 | 1.021 | 1.092 | 0.440 | 0.600 | 0.458 | 3.968 | 0.463 |
| Laminin subunit gamma-1 precursor (Laminin B2 chain) | gi126369 | vnNTLSSQISR | N-Term(iTRAQ8plex), N2(Deamidated) | 2 | 762.41846 | 1523.82964 | -2.28 | 77.07 | 1.016 | 0.933 | 0.687 | 0.522 | 0.844 | 2.666 | 0.681 |

FIG. 7 cont'd.

| Protein Name | Protein Accessions | Peptides | Modifications | Charge | m/z [Da] | MH+ [Da] | ΔM [ppm] | RT [min] | 114/113 | 115/113 | 116/113 | 117/113 | 118/113 | 119/113 | 121/113 |
|---|---|---|---|---|---|---|---|---|---|---|---|---|---|---|---|
| Acid phosphatase 2, lysosomal [Homo sapiens] | gi|13111975 | yEQLQnETR | N-Term(iTRAQ8plex), N6(Deamidated) | 2 | 743.37640 | 1485.74553 | -2.13 | 69.85 | 0.846 | 0.624 | 1.416 | 0.562 | 1.642 | 1.289 | 1.996 |
| Tetraspanin 8 [Homo sapiens] | gi|13528897 | iVnETLYENTk | N-Term(iTRAQ8plex), N3(Deamidated), K11(iTRAQ8plex) | 3 | 645.02661 | 1933.06528 | -4.43 | 89.95 | 0.630 | 0.531 | 0.518 | 0.583 | 0.650 | 0.474 | 0.373 |
| HPX protein [Homo sapiens] | gi|13529281 | sWPAVGncSSALR | N-Term(iTRAQ8plex), N7(Deamidated), C8(Carbamidomethyl) | 2 | 855.43036 | 1709.85344 | -2.84 | 86.88 | 1.132 | 0.827 | 1.042 | 1.114 | 2.231 | 5.946 | 1.299 |
| type VI collagen alpha 2 chain precursor [Homo sapiens] | gi|13603394 | nmTLFSDLVAEk | N-Term(iTRAQ8plex), N1(Deamidated), M2(Oxidation), K12(iTRAQ8plex) | 3 | 665.02771 | 1993.06858 | -4.35 | 96.99 | 0.651 | 0.423 | | 0.739 | 0.554 | 1.983 | 0.361 |

FIG. 7 cont'd.

| Protein Name | Protein Accessions | Peptides | Modifications | Charge | m/z [Da] | MH+ [Da] | ΔM [ppm] | RT [min] | 114/113 | 115/113 | 116/113 | 117/113 | 118/113 | 119/113 | 121/113 |
|---|---|---|---|---|---|---|---|---|---|---|---|---|---|---|---|
| cysteine-rich fibroblast growth factor receptor | gi\|373019 | lnLTTDPk | N-Term(iTRAQ8plex), N2(Deamidated), K8(iTRAQ8plex) | 2 | 755.94385 | 1510.88042 | -8.79 | 82.68 | 1.173 | 0.971 | 1.224 | 1.015 | 1.088 | 1.168 | 1.273 |
| EMILIN1 protein [Homo sapiens] | gi\|4043093 | cTnTTSQmQAALLEk | N-Term(iTRAQ8plex), N3(Deamidated), M8(Oxidation), K15(iTRAQ8plex) | 3 | 764.07062 | 2290.19730 | -3.67 | 82.36 | 1.276 | 1.444 | 0.765 | | 0.776 | 0.334 | 1.128 |
| HSP90B1 protein [Homo sapiens] | gi\|4327942 | eEEAIQLDGLnASQIR | N-Term(iTRAQ8plex), N11(Deamidated) | 3 | 697.69934 | 2091.08347 | -1.78 | 93.40 | 0.817 | 0.551 | 0.418 | 0.760 | 0.611 | 0.645 | 0.730 |
| alpha-N-acetylglucosaminidase | gi\|479983 | vFPQVnVTk | N-Term(iTRAQ8plex), N6(Deamidated), K9(iTRAQ8plex) | 3 | 547.66205 | 1640.97159 | -7.07 | 89.01 | 0.412 | 0.352 | 0.275 | 0.424 | 0.401 | 0.358 | 0.421 |
| ceruloplasmin [Homo sapiens] | gi\|1620909 | eHFGAIYPDnTTDFQR | N-Term(iTRAQ8plex), N10(Deamidated) | 3 | 733.34686 | 2198.02604 | -1.98 | 81.13 | 1.105 | 0.655 | 0.518 | 1.160 | 1.378 | 0.664 | 1.314 |

FIG. 7 cont'd.

| Protein Name | Protein Accessions | Peptides | Modifications | Charge | m/z [Da] | MH+ [Da] | ΔM [ppm] | RT [min] | 114/113 | 115/113 | 116/113 | 117/113 | 118/113 | 119/113 | 121/113 |
|---|---|---|---|---|---|---|---|---|---|---|---|---|---|---|---|
| ceruloplasmin [Homo sapiens] | gi\|620909 | enLTAPGSDSAVFFEQGTTR | N-Term(iTRAQ8plex), N2(Deamidated) | 3 | 811.40076 | 2432.18772 | -0.27 | 94.45 | 0.692 | 0.469 | 0.421 | 0.868 | 0.430 | 0.414 | 0.631 |
| ASAH1 protein [Homo sapiens] | gi\|16877108 | tVLEnSTSYEEAk | N-Term(iTRAQ8plex), N5(Deamidated), K13(iTRAQ8plex) | 2 | ######## | 2080.08403 | -3.17 | 84.46 | 0.863 | 0.964 | 1.476 | 0.633 | 2.183 | 2.681 | 1.612 |
| C1-inhibitor | gi\|79617 | dlFVnASR | N-Term(iTRAQ8plex), N5(Deamidated) | 2 | 607.81750 | 1214.62773 | -3.42 | 53.93 | 0.679 | 0.994 | 0.687 | 1.434 | 0.646 | 0.363 | 0.642 |
| complement H factor | gi\|80498 | iSEEnETTcYmGk | N-Term(iTRAQ8plex), N5(Deamidated), C9(Carbamidomethyl), M11(Oxidation), K13(iTRAQ8plex) | 3 | 729.68347 | 2187.03586 | -2.16 | 78.48 | 1.005 | 0.285 | 0.808 | 0.709 | 0.966 | 0.532 | 0.503 |
| fibronectin receptor alpha-subunit precursor [Homo sapiens] | gi\|182710 | nLnNSQSDVVSFR | N-Term(iTRAQ8plex), N3(Deamidated) | 2 | 892.95593 | 1784.90459 | -1.95 | 83.95 | 3.362 | 1.367 | 2.164 | 2.433 | 3.213 | 15.073 | 1.254 |

FIG. 7 cont'd.

| Protein Name | Protein Accessions | Peptides | Modifications | Charge | m/z [Da] | MH+ [Da] | ΔM [ppm] | RT [min] | 114/113 | 115/113 | 116/113 | 117/113 | 118/113 | 119/113 | 121/113 |
|---|---|---|---|---|---|---|---|---|---|---|---|---|---|---|---|
| collagen VI-alpha-1 chain [Homo sapiens] | gi\|1915900 | nFTAADWGQSR | N-Term(iTRAQ8plex), N1(Deamidated) | 2 | 779.38062 | 1557.75395 | -3.85 | 86.43 | 1.170 | 1.370 | 1.058 | 0.246 | 1.125 | 0.494 | 0.511 |
| collagen VI-alpha-1 chain [Homo sapiens] | gi\|1915900 | mFTAADWGQSR | N-Term(iTRAQ8plex), N2(Deamidated) | 3 | 571.95801 | 1713.85947 | -0.94 | 81.15 | 0.783 | 0.466 | 0.478 | 0.489 | 0.686 | 0.498 | 0.576 |
| integrin beta 1 isoform 1B precursor [Homo sapiens] | gi\|9743815 | nPcTSEQncTSPFSYk | N-Term(iTRAQ8plex), C3(Carbamidomethyl), N8(Deamidated), C9(Carbamidomethyl), K16(iTRAQ8plex) | 3 | 843.72949 | 2529.17392 | -4.23 | 84.21 | 1.153 | 1.170 | 2.067 | 1.980 | 1.189 | 7.544 | 1.202 |
| Chain A, Fc Fragment Of Rituximab Bound To A Minimized Version Of The B-Domain From Protein A Called Z34c | gi\|20664303 | eEQYnSTYR | N-Term(iTRAQ8plex), N5(Deamidated) | 3 | 498.90378 | 1494.69678 | -3.09 | 47.82 | 1.360 | 1.209 | 0.758 | 0.814 | 1.413 | 1.579 | 1.141 |

FIG. 7 cont'd.

| carboxypeptidase D [Homo sapiens] | gi21903712 | fANEYPnITR | N-Term(iTRAQ8plex), N7(Deamidated) | 2 | 765.39386 | 1529.78044 | -6.36 | 87.02 | 1.023 | 0.760 | 0.960 | 0.942 | 1.421 | 1.059 | 1.403 |
|---|---|---|---|---|---|---|---|---|---|---|---|---|---|---|---|
| aminopeptidase N | gi228379 | lnYTLSQGHR | N-Term(iTRAQ8plex), N2(Deamidated) | 3 | 498.60516 | 1493.80094 | -0.31 | 77.54 | 1.197 | 0.573 | 0.768 | 1.217 | 1.030 | 0.660 | 0.647 |
| microfibrillar-associated protein 4 [Homo sapiens] | gi23111005 | fnGSVSFF R | N-Term(iTRAQ8plex), N2(Deamidated) | 3 | 455.90692 | 1365.70621 | -3.12 | 96.00 | 1.560 | 1.290 | 0.140 | 0.340 | 0.381 | 0.870 | 1.698 |
| microfibrillar-associated protein 4 [Homo sapiens] | gi23111005 | vDLEDFEnNTAYAk | N-Term(iTRAQ8plex), N8(Deamidated), K14(iTRAQ8plex) | 2 | ######## | 2238.13164 | -3.14 | 94.09 | 0.948 | 1.502 | 0.314 | 0.198 | 0.410 | 0.525 | 1.297 |
| immunoglobulin heavy chain, constant region [Homo sapiens] | gi2414494 | eEQFnSTYR | N-Term(iTRAQ8plex), N5(Deamidated) | 2 | 739.85406 | 1478.70085 | -3.82 | 61.70 | 2.046 | 1.742 | 1.079 | 1.186 | 1.929 | 0.666 | 8.762 |

FIG. 7 cont'd.

| Protein Name | Protein Accessions | Peptides | Modifications | Charge | m/z [Da] | MH+ [Da] | ΔM [ppm] | RT [min] | 114/113 | 115/113 | 116/113 | 117/113 | 118/113 | 119/113 | 121/113 |
|---|---|---|---|---|---|---|---|---|---|---|---|---|---|---|---|
| alpha2-HS glycoprotein [Homo sapiens] | gi2521981 | vcQDcPLL APLnDTR | N-Term(iTRAQ8plex), C2(Carbamidomethyl), C5(Carbamidomethyl), N12(Deamidated) | 2 | ######## | 2077.02764 | -4.04 | 96.14 | 1.751 | 1.157 | 1.248 | 0.861 | 3.085 | 10.023 | 1.656 |
| Chain A, Human Beta-Glucuronidase At 2.6 A Resolution | gi2554776 | vVAnGTG TQGQLk | N-Term(iTRAQ8plex), N4(Deamidated), K13(iTRAQ8plex) | 3 | 628.03027 | 1882.07627 | -4.87 | 67.90 | 0.785 | 0.601 | 0.997 | 0.311 | 0.729 | 0.447 | 1.271 |
| Chain U, Complex Of Active Site Inhibited Human Blood Coagulation Factor Viia With Human Recombinant Soluble Tissue Factor | gi2554907 | vnVTVED FR | N-Term(iTRAQ8plex), N2(Deamidated) | 2 | 683.36029 | 1365.71330 | -2.24 | 64.96 | 0.663 | 0.534 | 0.481 | 9.714 | 0.663 | 0.509 | 0.647 |
| immunoglobulin gamma 2 heavy chain constant region [Homo sapiens] | gi25987831 | eFQFnSTF R | N-Term(iTRAQ8plex), N5(Deamidated) | 2 | 731.85754 | 1462.70781 | -2.59 | 81.09 | 2.254 | 1.475 | 0.368 | 0.727 | 0.823 | 0.416 | 3.565 |

FIG. 7 cont'd.

| Protein Name | Protein Accessions | Peptides | Modifications | Charge | m/z [Da] | MH+ [Da] | ΔM [ppm] | RT [min] | 114/113 | 115/113 | 116/113 | 117/113 | 118/113 | 119/113 | 121/113 |
|---|---|---|---|---|---|---|---|---|---|---|---|---|---|---|---|
| KIAA0533 protein [Homo sapiens] | gi3043590 | dnATLQATLHAAR | N-Term(iTRAQ8plex), N2(Deamidated) | 3 | 562.97168 | 1686.90049 | -4.27 | 82.38 | 0.657 | 0.416 | 0.293 | 0.536 | 0.473 | 0.709 | 0.556 |
| KIAA0533 protein [Homo sapiens] | gi3043590 | lnTTGVSAGcTADLLVGR | N-Term(iTRAQ8plex), N2(Deamidated), C10(Carbamidomethyl) | 3 | 704.04431 | 2110.11838 | 3.19 | 95.02 | 0.677 | 0.432 | 0.343 | 0.488 | 0.525 | 0.536 | 0.648 |
| lysosomal membrane glycoprotein-2 | gi307110 | vQPFnVTQGk | N-Term(iTRAQ8plex), N5(Deamidated), K10(iTRAQ8plex) | 2 | 863.99762 | 1726.98796 | -3.97 | 84.09 | 1.002 | 0.916 | 2.291 | 0.616 | 1.637 | 1.825 | 1.470 |
| lysosomal membrane glycoprotein-2 | gi307110 | wQmnFTVR | N-Term(iTRAQ8plex), M3(Oxidation), N4(Deamidated) | 2 | 701.85553 | 1402.70378 | -3.79 | 88.66 | 0.697 | 0.434 | 0.622 | 0.474 | 1.051 | 1.425 | 1.367 |

FIG. 7 cont'd.

| Protein Name | Protein Accessions | Peptides | Modifications | Charge | m/z [Da] | MH+ [Da] | ΔM [ppm] | RT [min] | 114/113 | 115/113 | 116/113 | 117/113 | 118/113 | 119/113 | 121/113 |
|---|---|---|---|---|---|---|---|---|---|---|---|---|---|---|---|
| integrin, alpha 1 precursor [Homo sapiens] | gi31657142 | nTTFNVES1k | N-Term(iTRAQ8plex), N1(Deamidated), K10(iTRAQ8plex) | 3 | 583.98602 | 1749.94352 | -2.52 | 76.28 | 1.046 | 1.569 | 0.506 | 0.820 | 0.492 | 0.678 | 0.492 |
| integrin, alpha 1 precursor [Homo sapiens] | gi31657142 | sEnASLVLSSSNQk | N-Term(iTRAQ8plex), N3(Deamidated), K14(iTRAQ8plex) | 3 | 691.71124 | 2073.11917 | -4.46 | 83.53 | 1.406 | 0.929 | 0.699 | 1.137 | 1.287 | 2.055 | 0.832 |
| integrin, alpha 1 precursor [Homo sapiens] | gi31657142 | vYVYALnQTR | N-Term(iTRAQ8plex), N7(Deamidated) | 2 | 766.42200 | 1531.83672 | -3.58 | 91.43 | 1.125 | 1.033 | 0.817 | 0.889 | 0.985 | 1.860 | 1.256 |
| hypothetical protein [Homo sapiens] | gi31873561 | tmFPnLTDVR | N-Term(iTRAQ8plex), M2(Oxidation), N5(Deamidated) | 2 | 757.89307 | 1514.77886 | -2.52 | 89.88 | 1.021 | 0.562 | 0.482 | 0.582 | 0.787 | 1.264 | 1.159 |
| sulfated glycoprotein-2 | gi338057 | eDALnETR | N-Term(iTRAQ8plex), N5(Deamidated) | 2 | 626.81970 | 1252.63213 | -0.13 | 52.81 | 1.080 | 1.046 | 0.794 | 0.927 | 0.770 | 0.210 | 2.112 |

FIG. 7 cont'd.

| Protein Name | Protein Accessions | Peptides | Modifications | Charge | m/z [Da] | MH+ [Da] | ΔM [ppm] | RT [min] | 114/113 | 115/113 | 116/113 | 117/113 | 118/113 | 119/113 | 121/113 |
|---|---|---|---|---|---|---|---|---|---|---|---|---|---|---|---|
| sulfated glycoprotein-2 | gi338057 | lAnLTQGEDQYYLR | N-Term(iTRAQ8plex), N3(Deamidated) | 2 | 995.01166 | 1989.01604 | -3.55 | 96.65 | 1.288 | 1.308 | 0.433 | 1.265 | 0.639 | 0.349 | 1.944 |
| transferrin | gi339469 | gLVPVLAENYnk | N-Term(iTRAQ8plex), N11(Deamidated), K12(iTRAQ8plex) | 2 | 963.55560 | 1926.10393 | -6.09 | 93.21 | 1.543 | 0.901 | 1.791 | 0.961 | 1.590 | 2.292 | 1.311 |
| inter-alpha-trypsin inhibitor heavy chain [ITIH1 [Homo sapiens] | gi33989 | anLSSQALR | N-Term(iTRAQ8plex), N2(Deamidated) | 2 | 632.85986 | 1264.71245 | -3.03 | 58.64 | 0.701 | 1.299 | 0.511 | 0.227 | 0.494 | 0.167 | 0.930 |
| HP protein [Homo sapiens] | gi34785974 | nLFLnHSEnATAk | N-Term(iTRAQ8plex), N5(Deamidated), N9(Deamidated), K13(iTRAQ8plex) | 2 | ######## | 2069.10307 | -4.49 | 81.01 | 4.767 | 0.999 | 0.337 | 6.168 | 1.962 | 2.450 | 10.207 |

FIG. 7 cont'd.

| Protein Name | Protein Accessions | Peptides | Modifications | Charge | m/z [Da] | MH+ [Da] | ΔM [ppm] | RT [min] | 114/113 | 115/113 | 116/113 | 117/113 | 118/113 | 119/113 | 121/113 |
|---|---|---|---|---|---|---|---|---|---|---|---|---|---|---|---|
| HP protein [Homo sapiens] | gi34785974 | vVLHPnYSQVDIGLIk | N-Term(iTRAQ8plex), N6(Deamidated); K16(iTRAQ8plex) | 3 | 802.13641 | 2404.39469 | -4.72 | 95.49 | 0.936 | 0.290 | | 0.685 | 0.381 | 0.264 | 1.232 |
| Chain A, Crystal Structure Of A Human Igm Rheumatoid Factor Fab In Complex With Its Autoantigen Igg Fc | gi3659940 | eqQFnSIYR | N-Term(iTRAQ8plex), Q2(Deamidated); N5(Deamidated) | 2 | 739.85406 | 1478.70085 | -3.81 | 61.70 | 2.046 | 1.742 | 1.079 | 1.186 | 1.929 | 0.666 | 8.762 |
| Chain A, Structural Origins Of L(+)-Tartrate Inhibition Of Human Prostatic Acid Phosphatase | gi3660342 | fLnESYk | N-Term(iTRAQ8plex), N3(Deamidated); K7(iTRAQ8plex) | 2 | 755.41895 | 1509.83061 | -6.82 | 87.63 | 5.341 | 4.310 | 9.322 | 5.055 | 25.338 | 14.592 | 7.422 |

FIG. 7 cont'd.

| Protein Name | Protein Accessions | Peptides | Modifications | Charge | m/z [Da] | MH+ [Da] | ΔM [ppm] | RT [min] | 114/113 | 115/113 | 116/113 | 117/113 | 118/113 | 119/113 | 121/113 |
|---|---|---|---|---|---|---|---|---|---|---|---|---|---|---|---|
| Chain A, Structural Origins Of L(+)-1artrate Inhibition Of Human Prostatic Acid Phosphatase | gi3660342 | kFLnESYk | N-Term(iTRAQ8plex), K1(iTRAQ8plex), N4(Deamidated), K8(iTRAQ8plex) | 4 | 486.28677 | 1942.12526 | -8.23 | 82.97 | 0.550 | 0.418 | 0.576 | 0.453 | 1.088 | 0.909 | 0.677 |
| beta-2-glycoprotein I [Homo sapiens] | gi3688372 | vYkPSAGn NSLYR | N-Term(iTRAQ8plex), K3(iTRAQ8plex), N8(Deamidated) | 4 | 520.29242 | 2078.14785 | -0.59 | 80.54 | 0.724 | 0.711 | 0.543 | 0.622 | 0.916 | 0.501 | 0.863 |
| CD47 antigen isoform 2 precursor [Homo sapiens] | gi38683836 | dIYTFDG ALnk | N-Term(iTRAQ8plex), N10(Deamidated), K11(iTRAQ8plex) | 2 | 933.50287 | 1865.99846 | -6.47 | 93.48 | 1.467 | 1.214 | 1.553 | 0.987 | 2.002 | 2.630 | 1.994 |
| Immunoglobulin J chain | gi400044 | enISDPTS PLR | N-Term(iTRAQ8plex), N2(Deamidated) | 2 | 767.40289 | 1533.79851 | -5.04 | 80.69 | 1.002 | 2.457 | 0.451 | 2.781 | 1.629 | 0.401 | 0.753 |

FIG. 7 cont'd.

| Protein Name | Protein Accessions | Peptides | Modifications | Charge | m/z [Da] | MH+ [Da] | ΔM [ppm] | RT [min] | 114/113 | 115/113 | 116/113 | 117/113 | 118/113 | 119/113 | 121/113 |
|---|---|---|---|---|---|---|---|---|---|---|---|---|---|---|---|
| desmoglein 2 [Homo sapiens] | gi\|4416178 | inATDADEPNTLNSk | N-Term(iTRAQ8plex), N2(Deamidated), K15(iTRAQ8plex) | 3 | 738.05304 | 2212.14457 | -4.89 | 81.10 | 1.311 | 1.657 | 2.464 | 1.224 | 1.582 | 1.389 | 0.811 |
| desmoglein 2 [Homo sapiens] | gi\|4416178 | yVQnGTYTVk | N-Term(iTRAQ8plex), N4(Deamidated), K10(iTRAQ8plex) | 3 | 594.66321 | 1781.97507 | -8.02 | 79.76 | 0.939 | 0.521 | 0.450 | 0.449 | 1.508 | 0.399 | 0.441 |
| amine oxidase, copper containing 3 precursor [Homo sapiens] | gi\|4502119 | iQmLSFAGEPLPQnSSmAR | N-Term(iTRAQ8plex), M3(Oxidation), N14(Deamidated), M17(Oxidation) | 2 | ######## | 2414.19438 | -2.25 | 93.59 | 1.870 | 0.424 | 2.283 | 1.264 | 2.892 | 8.984 | 1.530 |
| carboxypeptidase E preproprotein [Homo sapiens] | gi\|4503009 | gnETTVNLIHSTR | N-Term(iTRAQ8plex), N2(Deamidated) | 3 | 586.99048 | 1758.95688 | -4.73 | 91.80 | 0.850 | 0.498 | 0.421 | 0.535 | 0.919 | 0.924 | 0.932 |
| cathepsin D preproprotein [Homo sapiens] | gi\|4503143 | gSLSYLnVTR | N-Term(iTRAQ8plex), N7(Deamidated) | 2 | 707.89374 | 1414.78020 | -2.94 | 87.17 | 0.679 | 0.849 | 0.843 | 0.467 | 0.979 | 0.792 | 1.296 |

FIG. 7 cont'd.

| Protein Name | Protein Accessions | Peptides | Modifications | Charge | m/z [Da] | MH+ [Da] | ΔM [ppm] | RT [min] | 114/113 | 115/113 | 116/113 | 117/113 | 118/113 | 119/113 | 121/113 |
|---|---|---|---|---|---|---|---|---|---|---|---|---|---|---|---|
| fibromodulin [Homo sapiens] | gi 4531157 | IYLDHNn LTR | N-Term(iTRAQ8plex), N7(Deamidated) | 3 | 521.94971 | 1563.83457 | -5.56 | 83.79 | 0.475 | 0.542 | 0.281 | 0.249 | 0.538 | 0.658 | 0.480 |
| fibrillin 1 [Homo sapiens] | gi 46559356 | vLPVnVT DYcQLVR | N-Term(iTRAQ8plex), N5(Deamidated), C10(Carbamidomethyl) | 2 | 991.03967 | 1981.07207 | -0.49 | 97.34 | 1.480 | 1.603 | 0.497 | 0.370 | 0.955 | 1.986 | 1.707 |
| Chain B, Human Zinc-Alpha-2-Glycoprotein | gi 4699583 | dIVEYYn DSnGSHV LQGR | N-Term(iTRAQ8plex), N7(Deamidated), N10(Deamidated) | 3 | 791.37982 | 2372.12491 | -2.49 | 91.75 | 1.518 | 0.696 | 1.309 | 1.131 | 2.278 | 2.654 | 2.008 |
| Chain B, Human Zinc-Alpha-2-Glycoprotein | gi 4699583 | fGcElENn R | N-Term(iTRAQ8plex), C3(Carbamidomethyl), N8(Deamidated) | 2 | 722.34436 | 1443.68144 | -1.78 | 75.82 | 2.501 | 1.115 | 7.889 | 1.718 | 8.566 | 15.306 | 6.280 |

FIG. 7 cont'd.

| Protein Name | Protein Accessions | Peptides | Modifications | Charge | m/z [Da] | MH+ [Da] | ΔM [ppm] | RT [min] | 114/113 | 115/113 | 116/113 | 117/113 | 118/113 | 119/113 | 121/113 |
|---|---|---|---|---|---|---|---|---|---|---|---|---|---|---|---|
| HYOU1 protein [Homo sapiens] | gi47938913 | vFGSQnLTTVk | N-Term(iTRAQ8plex), N6(Deamidated), K11(iTRAQ8plex) | 2 | 902.02911 | 1803.05095 | 2.05 | 88.05 | 0.701 | 0.863 | 1.989 | 3.174 | 1.510 | 0.956 | 1.214 |
| GOLPH2 [Homo sapiens] | gi48146519 | aVLVnnITTGER | N-Term(iTRAQ8plex), N5(Deamidated), N6(Deamidated) | 2 | 796.93860 | 1592.86992 | -6.17 | 83.92 | 0.804 | 0.971 | 2.525 | 1.236 | 1.900 | 1.321 | 1.950 |
| galectin 3 binding protein [Homo sapiens] | gi5031863 | aAIPSALDTnSSk | N-Term(iTRAQ8plex), N10(Deamidated), K13(iTRAQ8plex) | 3 | 628.68817 | 1884.04996 | -1.86 | 83.88 | 1.055 | 1.094 | 1.557 | 3.905 | 1.464 | | 1.177 |
| galectin 3 binding protein [Homo sapiens] | gi5031863 | aLGFEnATQALGR | N-Term(iTRAQ8plex), N6(Deamidated) | 2 | 826.94916 | 1652.89104 | 0.03 | 94.18 | 0.604 | 0.642 | 2.405 | 4.645 | 1.847 | 0.520 | 0.575 |
| myelin protein zero-like 2 precursor [Homo sapiens] | gi5032247 | vLEAVnGTDAR | N-Term(iTRAQ8plex), N6(Deamidated) | 2 | 725.39380 | 1449.78032 | -3.31 | 86.48 | 0.717 | 0.747 | 0.958 | 0.743 | 1.058 | 0.995 | 0.950 |

FIG. 7 cont'd.

| Protein Name | Protein Accessions | Peptides | Modifications | Charge | m/z [Da] | MH+ [Da] | ΔM [ppm] | RT [min] | 114/113 | 115/113 | 116/113 | 117/113 | 118/113 | 119/113 | 121/113 |
|---|---|---|---|---|---|---|---|---|---|---|---|---|---|---|---|
| hypothetical protein [Homo sapiens] | gi51476184 | anYTILk | N-Term(iTRAQ8plex), N2(Deamidated); K7(iTRAQ8plex) | 2 | 716.43402 | 1431.86077 | -4.17 | 83.78 | 1.165 | 0.642 | 1.361 | 1.002 | 1.488 | 0.675 | 0.877 |
| hypothetical protein [Homo sapiens] | gi51476184 | nGlYnlTVLASDQGGR | N-Term(iTRAQ8plex), N1(Deamidated), N5(Deamidated) | 2 | 992.51953 | 1984.03179 | 1.44 | 96.81 | 1.543 | 2.182 | 1.271 | 0.834 | 3.191 | 2.185 | 2.101 |
| hypothetical protein [Homo sapiens] | gi52545569 | anDTSYIR | N-Term(iTRAQ8plex), N2(Deamidated) | 2 | 622.82288 | 1244.63848 | -3.18 | 52.21 | 1.196 | 2.917 | 1.601 | 0.629 | 1.176 | 0.531 | 1.234 |
| hypoxia up-regulated 1 precursor [Homo sapiens] | gi5453832 | aEPPLnASASDQGEk | N-Term(iTRAQ8plex), N6(Deamidated); K15(iTRAQ8plex) | 3 | 708.37085 | 2123.09800 | -4.57 | 63.22 | 1.237 | 1.541 | 2.315 | 0.793 | 1.963 | 1.257 | 2.284 |
| SM-11044 binding protein (SMBP)(LP70-P-iso) [Homo sapiens] | gi5957667 | iVDVnLISEGk | N-Term(iTRAQ8plex), N5(Deamidated); K11(iTRAQ8plex) | 2 | 892.51147 | 1784.01567 | -5.89 | 89.54 | 0.949 | 1.232 | 1.951 | 1.265 | 2.083 | 2.083 | 1.995 |

FIG. 7 cont'd.

| Protein Name | Protein Accessions | Peptides | Modifications | Charge | m/z [Da] | MH+ [Da] | ΔM [ppm] | RT [min] | 114/113 | 115/113 | 116/113 | 117/113 | 118/113 | 119/113 | 121/113 |
|---|---|---|---|---|---|---|---|---|---|---|---|---|---|---|---|
| heparan sulfate proteoglycan 2 [Homo sapiens] | gi55960426 | aLVnFTR | N-Term(iTRAQ8plex), N4(Deamidated) | 2 | 563.32977 | 1125.65227 | -4.18 | 86.34 | 1.318 | 1.454 | 1.051 | 0.728 | 1.157 | 3.401 | 1.216 |
| OMM protein (Ig gamma3) heavy chain | gi567112 | eEQYnSTFR | N-Term(iTRAQ8plex), N5(Deamidated) | 2 | 739.85516 | 1478.70305 | -2.33 | 59.55 | 6.379 | 0.779 | 0.363 | 0.590 | 2.364 | 1.206 | 4.700 |
| TIMP metallopeptidase inhibitor 1 [Homo sapiens] | gi57210055 | fVGTPEVnQTTLYQR | N-Term(iTRAQ8plex), N8(Deamidated) | 3 | 686.69812 | 2058.07981 | -0.56 | 91.43 | 0.856 | 0.475 | 0.780 | 0.812 | 0.760 | 0.481 | 0.559 |
| ceroid-lipofuscinosis, neuronal 5 [Homo sapiens] | gi5729772 | nIETnYTR | N-Term(iTRAQ8plex), N5(Deamidated) | 2 | 658.34198 | 1315.67668 | -2.18 | 53.89 | 1.571 | 0.725 | 2.216 | 1.781 | 2.470 | 0.797 | 0.792 |
| fibrinogen-like 2 precursor [Homo sapiens] | gi5730075 | IDGSTnFTR | N-Term(iTRAQ8plex), N6(Deamidated) | 2 | 658.34167 | 1315.67607 | -2.66 | 77.23 | 1.402 | 1.097 | 0.503 | 0.320 | 0.721 | 0.362 | 0.713 |

FIG. 7 cont'd.

| Protein Name | Protein Accessions | Peptides | Modifications | Charge | m/z [Da] | MH+ [Da] | ΔM [ppm] | RT [min] | 114/113 | 115/113 | 116/113 | 117/113 | 118/113 | 119/113 | 121/113 |
|---|---|---|---|---|---|---|---|---|---|---|---|---|---|---|---|
| serine (or cysteine) proteinase inhibitor, clade A, member 3 precursor variant [Homo sapiens] | gi\|62087700 | iLnQSSDELQLSmGNAmFVk | N-Term(iTRAQ8plex), N3(Deamidated), M13(Oxidation), M17(Oxidation), K20(iTRAQ8plex) | 4 | 714.36304 | 2854.43032 | -4.22 | 91.25 | 0.798 | 0.268 | 0.278 | 0.706 | 0.571 | 0.949 | 0.645 |
| periostin [Homo sapiens] | gi\|62824474 | eVnDTLLVNELk | N-Term(iTRAQ8plex), N3(Deamidated), K12(iTRAQ8plex) | 2 | 998.56995 | 1996.13262 | -4.85 | 95.34 | 0.570 | 1.241 | 0.263 | 0.172 | 0.341 | 0.519 | 0.539 |
| unnamed protein product [Homo sapiens] | gi\|7020027 | iTDIEnGSLANIPR | N-Term(iTRAQ8plex), N6(Deamidated) | 2 | 909.49719 | 1817.98711 | -2.19 | 96.18 | 0.619 | 0.542 | 0.423 | 0.253 | 0.409 | 0.836 | 0.334 |
| Chain A, Crystal Structure Of Human Neutrophil Gelatinase Associated Lipocalin Monomer | gi\|7245433 | sYnVlSVLFR | N-Term(iTRAQ8plex), N3(Deamidated) | 2 | 745.90845 | 1490.80962 | -4.05 | 96.53 | 1.128 | 0.655 | 0.397 | 0.399 | 1.623 | 6.372 | 0.627 |

FIG. 7 cont'd.

| Protein Name | Protein Accessions | Peptides | Modifications | Charge | m/z [Da] | MH+ [Da] | ΔM [ppm] | RT [min] | 114/113 | 115/113 | 116/113 | 117/113 | 118/113 | 119/113 | 121/113 |
|---|---|---|---|---|---|---|---|---|---|---|---|---|---|---|---|
| Chain A, Human Complement Component C3 | gi78101267 | tVLTPAT NHmGnVT FTIPANR | N-Term(iTRAQ8plex), M10(Oxidation), N12(Deamidated) | 3 | 859.45270 | 2576.34354 | -0.37 | 89.00 | 2.595 | 0.418 | | 0.662 | 1.743 | 3.932 | 3.628 |
| Chain A, The Crystal Structure Of Cellular Repressor Of E1a-Stimulated Genes (Creg) | gi83753668 | vnITTxDI Ak | N-Term(iTRAQ8plex), N2(Deamidated), X6(M), X6(Oxidation), K10(iTRAQ8plex) | 3 | 592.31494 | 1774.93027 | -2.85 | 76.22 | 1.131 | 0.533 | 0.642 | 0.863 | 0.739 | 0.797 | 0.721 |
| alpha-albumin | gi857675 | dIENFnST Qk | N-Term(iTRAQ8plex), N6(Deamidated), K10(iTRAQ8plex) | 3 | 602.31836 | 1804.94052 | -7.32 | 81.21 | 0.888 | 0.757 | 0.526 | 0.707 | 0.740 | 0.490 | 0.571 |
| Ig alpha-2 chain C region (allotype A2m(2)) - human (fragment) | gi87783 | tPLTAnITk | N-Term(iTRAQ8plex), N6(Deamidated), K9(iTRAQ8plex) | 2 | 784.47571 | 1567.94414 | -4.72 | 83.56 | 1.139 | 2.259 | 0.582 | 2.435 | 1.693 | 0.569 | 0.652 |

FIG. 7 cont'd.

| Protein Name | Protein Accessions | Peptides | Modifications | Charge | m/z [Da] | MH+ [Da] | ΔM [ppm] | RT [min] | 114/113 | 115/113 | 116/113 | 117/113 | 118/113 | 119/113 | 121/113 |
|---|---|---|---|---|---|---|---|---|---|---|---|---|---|---|---|
| CD47 glycoprotein= ovarian tumour marker OA3 homolog [human, erythrocytes, Peptide Partial, 15 aa, segment 1 of 2] | gi894281 | dIYTFDGALxk | N-Term(iTRAQ8plex), X10(Deamidated), X10(N), K11(iTRAQ8plex) | 2 | 933.50287 | 1865.99846 | -6.47 | 93.48 | 1.467 | 1.214 | 1.553 | 0.987 | 2.002 | 2.630 | 1.994 |
| collagen, type XII, alpha 1 short isoform precursor [Homo sapiens] | gi93141049 | eAGmITTDGYEILGk | N-Term(iTRAQ8plex), N4(Deamidated), K15(iTRAQ8plex) | 3 | 730.72620 | 2190.16404 | -5.03 | 94.69 | 1.443 | 1.235 | 0.900 | 0.746 | 1.406 | 2.492 | 2.974 |
| collagen, type XII, alpha 1 short isoform precursor [Homo sapiens] | gi93141049 | mLEAYnLTEk | N-Term(iTRAQ8plex), M1(Oxidation), N6(Deamidated), K10(iTRAQ8plex) | 3 | 612.99811 | 1836.97977 | -4.13 | 87.67 | 1.174 | 0.988 | 1.280 | 0.476 | 1.650 | 0.849 | 1.170 |
| collagen, type XII, alpha 1 short isoform precursor [Homo sapiens] | gi93141049 | nLQVYnATSNSLTVk | N-Term(iTRAQ8plex), N6(Deamidated), K15(iTRAQ8plex) | 3 | 754.42090 | 2261.24814 | -5.14 | 88.80 | 4.820 | 2.600 | 0.260 | 0.298 | 0.291 | 0.462 | 0.770 |

FIG. 7 cont'd.

| Protein Name | Protein Accessions | Peptides | Modifications | Charge | m/z [Da] | MH+ [Da] | ΔM [ppm] | RT [min] | 114/113 | 115/113 | 116/113 | 117/113 | 118/113 | 119/113 | 121/113 |
|---|---|---|---|---|---|---|---|---|---|---|---|---|---|---|---|
| attractin isoform 2 [Homo sapiens] | gi21450863 | iDSTGnVTNELR | N-Term(iTRAQ8plex), N6(Deamidated) | 2 | 812.42651 | 1623.84575 | -2.10 | 84.49 | 1.183 | 1.039 | 1.055 | 0.864 | 1.400 | 1.832 | 1.171 |
| unnamed protein product [Homo sapiens] | gi21751668 | mIEnGSLSFLPTLR | N-Term(iTRAQ8plex), M1(Oxidation), N4(Deamidated) | 2 | 950.01038 | 1899.01348 | -3.42 | 97.49 | 1.222 | 0.775 | 0.243 | 0.279 | 0.595 | 2.318 | 1.740 |
| unnamed protein product [Homo sapiens] | gi21753029 | anTSALAVPSPVSNSASAR | N-Term(iTRAQ8plex), N2(Deamidated) | 3 | 702.37561 | 2105.11228 | -0.85 | 84.93 | 1.059 | 0.582 | 0.677 | 0.654 | 0.878 | 0.597 | 0.942 |
| unnamed protein product [Homo sapiens] | gi21753029 | rAnTSALAVPSPVSNSASAR | N-Term(iTRAQ8plex), N3(Deamidated) | 3 | 754.40979 | 2261.21482 | -0.17 | 80.01 | 1.024 | 0.807 | 0.350 | 0.493 | 0.907 | 0.888 | 0.778 |
| unnamed protein product [Homo sapiens] | gi21754713 | vnETEmDIAk | N-Term(iTRAQ8plex), N2(Deamidated), M6(Oxidation), K10(iTRAQ8plex) | 3 | 592.31494 | 1774.93027 | -2.85 | 76.22 | 1.131 | 0.533 | 0.642 | 0.863 | 0.739 | 0.797 | 0.721 |

FIG. 8

| Description | AG/NAG | t-TEST |
|---|---|---|
| Cathepsin L | 1.85 | 0.01 |
| Human Prostatic Acid Phosphatase | 0.28 | 0.02 |
| Microfibrillar-associated protein 4 | 5.16 | 0.03 |
| Fibrinogen-like protein 2 | 1.64 | 0.03 |
| Periodontal ligament-specific periostin | 2.43 | 0.04 |
| Heparan sulfate proteoglycan 2 | 2.52 | 0.04 |
| Galectin 3 binding protein | 3.15 | 0.04 |
| Biglycan | 2.74 | 0.04 |
| HYOU1 protein | 0.5 | 0.05 |
| Acid phosphatase 2, lysosomal | 1.76 | 0.07 |
| Ceroid-lipofuscinosis, neuronal 5 | 0.75 | 0.08 |
| Collagen VI-alpha-1 chain | 1.67 | 0.1 |
| Chain A, Human Beta-Glucuronidase At 2.6 A Resolution | 1.85 | 0.11 |
| C1-inhibitor | 1.52 | 0.11 |
| Human Neutral Endopeptidase Complexed With Phosphoramidon | 1.39 | 0.12 |
| SM-11044 binding protein (SMBP)(EP70-P-iso) | 1.4 | 0.12 |
| Desmocollin | 1.31 | 0.13 |
| Cathepsin D | 1.33 | 0.13 |
| Fibronectin receptor alpha-subunit | 0.63 | 0.13 |
| Fibrillin 1 | 1.52 | 0.13 |
| Mimecan | 1.8 | 0.13 |
| fibromodulin [Homo sapiens] | 1.44 | 0.13 |
| collagen, type XII, alpha 1 short isoform | 3.79 | 0.13 |
| Integrin beta 1 isoform 1B | 0.43 | 0.13 |
| Type VI collagen alpha 2 chain | 2.3 | 0.13 |
| ASAH1 protein | 1.81 | 0.14 |
| Laminin alpha-5 | 1.36 | 0.14 |
| Golgi phosphoprotein 2 | 0.82 | 0.15 |
| Lysosomal alpha-glucosidase | 1.33 | 0.16 |
| Tetraspanin 8 | 1.44 | 0.16 |
| clusterin isoform 2 preproprotein | 1.52 | 0.16 |
| Amine oxidase, copper containing 3 | 0.5 | 0.18 |
| Versican | 1.22 | 0.18 |
| Aminopeptidase N | 0.7 | 0.19 |
| Human Neutrophil Gelatinase Associated Lipocalin Monomer | 0.39 | 0.19 |
| Human Zinc-Alpha-2-Glycoprotein | 1.7 | 0.2 |
| Lysosome-associated membrane protein 2 | 1.71 | 0.2 |
| Attractin | 0.85 | 0.21 |
| Asporin | 1.3 | 0.24 |
| HP protein | 1.54 | 0.27 |
| Desmoglein 2 | 0.88 | 0.29 |
| CD63 | 1.13 | 0.38 |

FIG. 9

| | CV | |
|---|---|---|
| ID | NAG | AG |
| No Adjustment | 0.4 | 0.31 |
| Adjust for Tumor Nuclei | 0.34 | 0.42 |
| Adjust for Tumor Area | 0.32 | 0.5 | under 35 U.S.C. §371 U.S. national entry
BIOMARKERS FOR AGGRESSIVE PROSTATE CANCER

CROSS-REFERENCE TO RELATED APPLICATIONS

This application is a 35 U.S.C. §371 U.S. national entry of International Application PCT/US2012/030129 having an international filing date of Mar. 22, 2012 which claims the benefit of U.S. Provisional Application No. 61/598,582, filed Feb. 14, 2012, U.S. Provisional Application No. 61/523,548, filed Aug. 15, 2011, and U.S. Provisional Application No. 61/466,173, filed Mar. 22, 2011, the content of each of the aforementioned applications is herein incorporated by reference in their entirety.

STATEMENT OF GOVERNMENTAL INTEREST

This invention was made with government support under grant no. U01CA152813 awarded by the National Institutes of Health. The government has certain rights in the invention.

FIELD OF THE INVENTION

The present invention relates to the field of biomarkers. More specifically, the present invention relates to biomarkers useful in diagnosing aggressive prostate cancer.

BACKGROUND OF THE INVENTION

Prostate cancer is the most common malignancy in men and the second leading cause of death from cancer in the United States. Metastases are the major cause of death from cancer. Therefore, aggressive (AG) prostate cancer leads to a higher metastasis rate and requires early detection and treatment. Since the discovery of prostate-specific antigen (PSA), assays that detect this serum biomarker (together with digital rectal exams) have been used for the screening of prostate cancer. PSA testing has resulted in early detection and intervention. However, the major limitation of PSA is the low specificity and high prevalence of detecting benign prostatic hyperplasia, especially in older men. Early detection based on PSA testing also fails to distinguish aggressive prostate cancer from nonaggressive prostate cancer. Indeed, with the illustration of the limitations of the current PSA-based screening method, a recently published study randomly assigned 76 693 men at 10 U.S. study centers to receive either annual PSA screening (38 343 subjects) or usual care as the control (38 350 subjects); this study reported no statistical differences in prostate cancer specific mortality between the groups after 7-10 years of follow-up.

Besides preoperative PSA, clinical risk assessment tools for prostate cancer metastasis before surgery largely rely on the prostate biopsy Gleason score. However, the risk assessment based on this clinical criterion is too imprecise to be useful due to biopsy sampling error and interobserver grading differences. It is also unable to be used as a screening test for early detection of aggressive prostate cancer. Currently, aggressive prostate cancer is under-detected and under treated while nonaggressive prostate cancer is overdetected and overtreated. Consequences of the difficulty of distinguishing the aggressive and nonaggressive prostate cancer are that prostate cancer patients suffer from unnecessary surgeries, and health care faces massive unnecessary expenditures. Therefore, reliable biomarkers to distinguish aggressive and nonaggressive prostate cancer are badly needed to prevent patients with nonaggressive prostate cancer from overtreatment and to allow patients with aggressive cancer to receive appropriate treatment earlier in the course of their disease.

SUMMARY OF THE INVENTION

The present invention is based, at least in part, on the identification of proteins whose expression is significantly altered in aggressive prostate tumors. The present invention is the first proteomic study to elucidate the differentially expressed proteins associated with aggressive prostate cancer and thus, are potentially useful for the diagnosis of aggressive prostate cancer. Furthermore, the present invention demonstrates that OCT-embedded frozen tissues could be used in proteomic analysis, and may facilitate the use of OCT-embedded frozen tissues in biomarker discovery.

Accordingly, in one aspect, the present invention provides methods and compositions useful in diagnosing aggressive prostate cancer. In specific embodiments, a method for aggressive prostate cancer in a patient comprises the steps of (a) measuring the levels of one or more biomarkers in a sample collected from the patient; and (b) comparing the levels of the one or more biomarkers with predefined levels of the same biomarkers that correlate to a patient having aggressive prostate cancer and predefined levels of the same biomarkers that correlate to a patient not having aggressive prostate cancer, wherein a correlation to one of the predefined levels provides the diagnosis. In a specific embodiment, the one or more biomarkers is selected from the group consisting of cathepsin-L (CTSL), clusterin, neutrophil gelatinase associated lipocalin (NGAL), epithelial cell activating molecule (EpCAM), prostate specific antigen (PSA) and membrane metallo-endopeptidase (MME). In another embodiment, the one or more biomarkers comprises CTSL, clusterin, NGAL, EpCAM, PSA and MME. In such embodiments, the one or more biomarkers further comprise one or more biomarkers selected from the group consisting of periostin, microfibrillar-associated protein 4 (MFAP4), collagen XII, neprilysin, and asporin (ASPN).

In certain embodiments, the one or more biomarkers comprises CTSL, periostin, MFAP4, collagen XII, neprilysin, clusterin, NGAL, EpCAM, PSA MME, ASPN, or combinations thereof. In other embodiments, the one or more biomarkers is selected from the group consisting of CTSL, periostin, MFAP4, collagen XII, neprilysin, clusterin, NGAL, EpCAM, PSA, MME and ASPN. In further embodiments, the one or more biomarkers comprises CTSL, periostin, MFAP4, collagen XII, neprilysin, clusterin, NGAL, EpCAM, PSA, MME and ASPN.

In one embodiment, the one or more biomarkers is CTSL. In another embodiment, the one or more biomarkers is periostin. Alternatively, the one or more biomarkers can be MFAP4. In yet another embodiment, the one or more biomarkers is collagen XII. In one embodiment, the one or more biomarkers is neprilysin. In another embodiment, the one or more biomarkers is clusterin. In a specific embodiment, the one or more biomarkers is NGAL. In another specific embodiment, the one or more biomarkers is EpCAM. The one or more biomarkers can be PSA. Alternatively, the one or more biomarkers can be MME. In yet a further embodiment, the one or more biomarkers is ASPN.

In the methods of the present invention, the one or more biomarkers further comprises one or more biomarkers from FIG. 9. In other embodiments, the one or more biomarkers further comprises one or more biomarkers from FIG. 6. In alternative embodiments, the one or more biomarkers further comprises one or more biomarkers from FIG. 7. In other embodiments, the one or more biomarkers further comprises one or more biomarkers from FIGS. 6, 7 and 9. Indeed, the present invention provides methods that utilize any combination of the foregoing biomarkers.

A patient sample can be any type of traditional sample taken from a patient. In certain embodiments, the sample is a blood, plasma, or serum sample. In a specific embodiment, the sample is a blood sample. In another specific embodiment, the sample is a plasma sample. In yet another embodiment, the sample is a serum sample. Alternatively, the sample can be a tissue sample. For example, the sample could be an embedded tissue sample.

In the methods described herein, the measuring step can be performed using an immunoassay. In other embodiments, the measuring step is performed using mass spectrometry. In a specific embodiment, the mass spectrometry technique is multiple reaction monitoring mass spectrometry (MRM-MS).

In certain embodiments, the correlation to a patient not having aggressive prostate cancer refers to a patient having non-aggressive prostate cancer. In other embodiments, the correlation to a patient not having aggressive prostate cancer refers to a patient not having cancer.

The present invention further provides a method for diagnosing aggressive prostate cancer in a patient comprising the steps of (a) collecting a sample from the patient; (b) measuring the levels of a panel of biomarkers in the sample collected from the patient, wherein the panel of biomarkers comprises one or more of CTSL, clusterin, NGAL, EpCAM, PSA and MME; and (c) comparing the levels of the panel of biomarkers with predefined levels of the same panel of biomarkers that correlate to a patient having aggressive prostate cancer and predefined levels of the same panel of biomarkers that correlate to a patient not having aggressive prostate cancer, wherein a correlation to one of the predefined levels provides the diagnosis. In a specific embodiment, the panel of biomarkers further comprises one or more of MFAP4, collagen XII, neprilysin, and ASPN.

The present invention also provides methods for determining the aggressive prostate cancer status in a patient. In a specific embodiment, the method comprises the steps of (a) collecting a sample from the patient; (b) measuring the levels of a panel of biomarkers in the sample collected from the patient, wherein the panel of biomarkers comprises one or more of CTSL, clusterin, NGAL, EpCAM, PSA and MME; and (c) comparing the levels of the panel of biomarkers with predefined levels of the same panel of biomarkers that correlate to one or more aggressive prostate cancer statuses selected from the group consisting of having aggressive prostate cancer, not having aggressive prostate cancer, progressing aggressive prostate cancer, and regressing aggressive prostate cancer, wherein a correlation to one of the predefined levels determines the aggressive prostate cancer status of the patient. In certain embodiments, the panel of biomarkers further comprises one or more of MFAP4, collagen XII, neprilysin, and ASPN.

In yet another aspect, the present invention provides kits useful in diagnosing cancer. In certain embodiments, a diagnostic kit for diagnosing aggressive prostate cancer in a patient comprises (a) a substrate for collecting a biological sample from the patient; and (b) means for measuring the levels of one or more of CTSL, periostin, MFAP4, collagen XII, neprilysin, clusterin, NGAL, EpCAM, PSA MME and ASPN. In other embodiments, the kit further comprises means for measuring the levels of one or more of the biomarkers in FIGS. 6, 7 and 9.

BRIEF DESCRIPTION OF THE FIGURES

(FIG. 2A) microfibrillarassociated protein 4 (peptide, vDLEDFEnNTAYAk); (FIG. 2B) microfibrillar-associated protein 4 (peptide, fnGSVSFFR); (FIG. 2C) periostin; and (FIG. 2D) cathepsin L.

FIG. 4A: immunohistochemical analysis of prostate primary tumor and its adjacent normal tissue with antibody specific to cathepsin L. Cathepsin L was expressed in epithelial cells. Arrows indicate the epithelial cell staining of antibody against cathepsin L. FIG. 4B: immunohistochemical analysis of prostate primary tumor and its adjacent normal tissue with antibody specific to periostin. Staining exhibited a low background in the normal prostate samples but revealed an overexpression in peritumoral stroma of Gleason 3 tumors and strong overexpression in the peritumoral stroma of Gleason 4 tumors. Arrows point to the peritumoral stroma staining of antibody against periostin.

FIG. 5 is a table showing examples of glycoproteins overexpressed in aggressive (AG) prostate tumors.

FIG. 6 is a table listing glycopeptides identified from the mass spectrometry analysis as potential biomarkers.

FIG. 7 is a table listing 102 unique N-linked glycopeptides identified (with 95% confidence) from mass spectrometry analysis, representing 79 unique glycoproteins.

In FIG. 8, iTRAQ report tags show the increased glycoprotein expression in aggressive (AG) prostate tumor compared to non-aggressive (NAG) prostate tumor. AG-prostate cancer tissues were labeled with iTRAQ Tag 113, 114, 115 and 121 and NAG-prostate cancer tissues were labeled with iTRAQ Tag 116, 117, 118 and 119.

FIG. 9 is a list of 42 proteins identified in the discovery study, with an average ratio between aggressive and non-aggressive tissue and the p value of student's t-test.

DETAILED DESCRIPTION OF THE INVENTION

Figure 1:
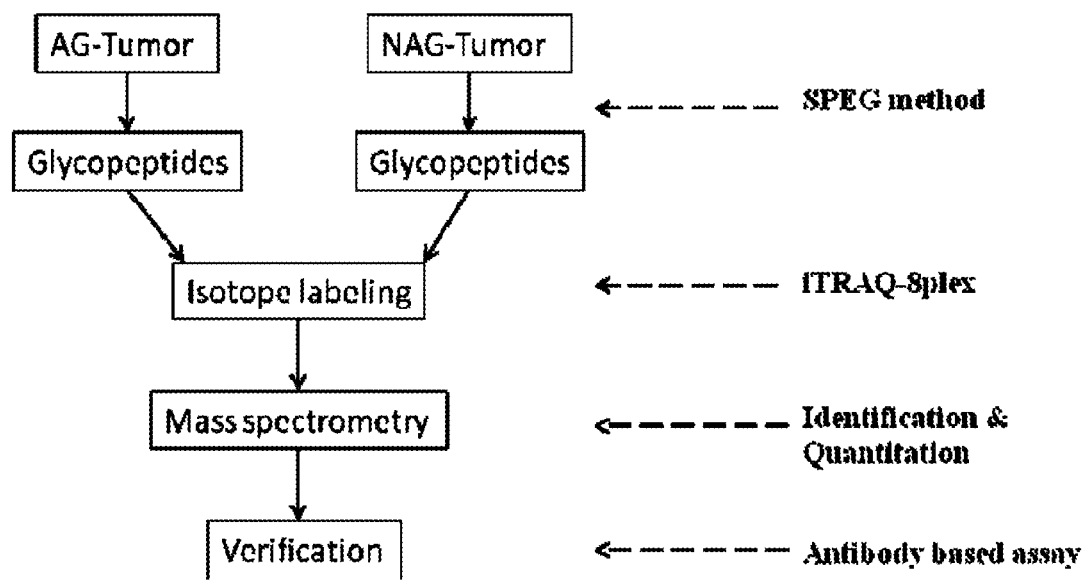
FIG. 1 present the workflow of identifying altered glycoprotein changes related to aggressive prostate carcinoma.
Figure 2:
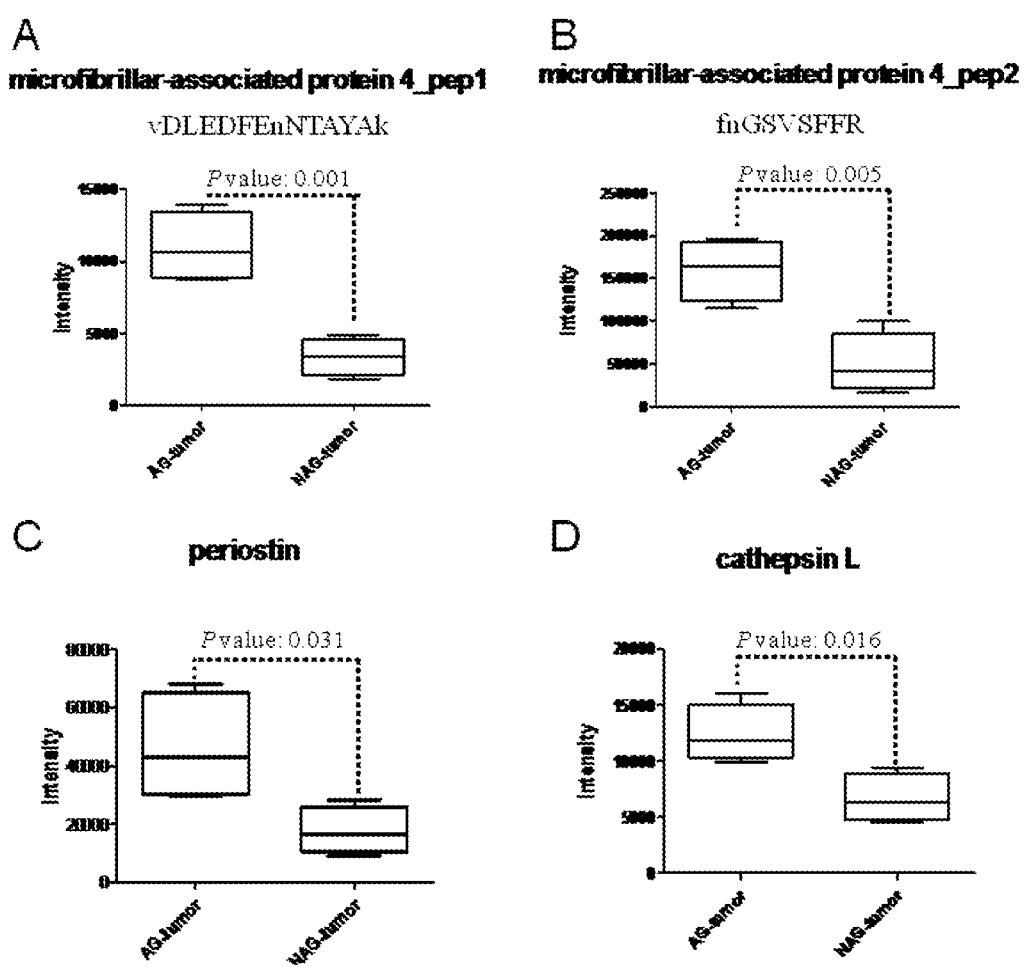
FIG. 2 shows the statistical analysis of protein expression in aggressive (AG) prostate tumor and nonaggressive (NAG) prostate tumor.

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

I. DEFINITIONS

As used herein, the term "antibody" is used in reference to any immunoglobulin molecule that reacts with a specific antigen. It is intended that the term encompass any immunoglobulin (e.g., IgG, IgM, IgA, IgE, IgD, etc.) obtained from any source (e.g., humans, rodents, non-human primates, caprines, bovines, equines, ovines, etc.). Specific types/examples of antibodies include polyclonal, monoclonal, humanized, chimeric, human, or otherwise-human-suitable antibodies. "Antibodies" also includes any fragment or derivative of any of the herein described antibodies.

As used herein, the term "comparing" refers to making an assessment of how the proportion, level or cellular localization of one or more biomarkers in a sample from a patient relates to the proportion, level or cellular localization of the corresponding one or more biomarkers in a standard or control sample. For example, "comparing" may refer to assessing whether the proportion, level, or cellular localization of one or more biomarkers in a sample from a patient is the same as, more or less than, or different from the proportion, level, or cellular localization of the corresponding one or more biomarkers in standard or control sample. More specifically, the term may refer to assessing whether the proportion, level, or cellular localization of one or more biomarkers in a sample from a patient is the same as, more or less than, different from or otherwise corresponds (or not) to the proportion, level, or cellular localization of predefined biomarker levels/ratios that correspond to, for example, a patient having aggressive prostate cancer, not having aggressive prostate cancer (e.g., non-aggressive prostate cancer or no cancer), is responding to treatment for aggressive prostate cancer, is not responding to treatment for aggressive prostate cancer, is/is not likely to respond to a particular aggressive prostate cancer treatment, or having/not having another disease or condition. In a specific embodiment, the term "comparing" refers to assessing whether the level of one or more biomarkers of the present invention in a sample from a patient is the same as, more or less than, different from other otherwise correspond (or not) to levels/ratios of the same biomarkers in a control sample (e.g., predefined levels/ratios that correlate to uninfected individuals, non-aggressive prostate cancer, standard aggressive prostate cancer levels/ratios, etc.).

In another embodiment, the term "comparing" refers to making an assessment of how the proportion, level or cellular localization of one or more biomarkers in a sample from a patient relates to the proportion, level or cellular localization of another biomarker in the same sample. For example, a ratio of one biomarker to another from the same patient sample can be compared. In another embodiment, a level of one biomarker in a sample (e.g., a post-translationally modified biomarker protein) can be compared to the level of the same biomarker (e.g., unmodified biomarker protein) in the sample. In a specific embodiment, the proportion of a glycosylated biomarker protein can be compared to the unmodified protein, both of which are measured in the same patient sample. Ratios of modified:unmodified biomarker proteins can be compared to other protein ratios in the same sample or to predefined reference or control ratios.

As used herein, the terms "indicates" or "correlates" (or "indicating" or "correlating," or "indication" or "correlation," depending on the context) in reference to a parameter, e.g., a modulated proportion, level, or cellular localization in a sample from a patient, may mean that the patient has aggressive prostate cancer. In specific embodiments, the parameter may comprise the level of one or more biomarkers of the present invention. A particular set or pattern of the amounts of one or more biomarkers may indicate that a patient has aggressive prostate cancer (i.e., correlates to a patient having aggressive prostate cancer). In other embodiments, a correlation could be that the ratio of a post-translationally modified protein (e.g., glycosylation) to the unmodified protein indicates (or a change in the ratio over time or as compared to a reference/control ratio) that the patient has aggressive prostate cancer. In specific embodiments, a correlation could be the ratio of a glycosylated peptide to the non-glycosylated form, or any other combination in which a change in one peptide causes or is accompanied by a change in another.

In other embodiments, a particular set or pattern of the amounts of one or more biomarkers may be correlated to a patient being unaffected (i.e., indicates a patient does not have aggressive prostate cancer, a patient has non-aggressive prostate cancer, or a patient does not have cancer). In certain embodiments, "indicating," or "correlating," as used according to the present invention, may be by any linear or non-linear method of quantifying the relationship between levels/ratios of biomarkers to a standard, control or comparative value for the assessment of the diagnosis, prediction of aggressive prostate cancer or aggressive prostate cancer progression, assessment of efficacy of clinical treatment, identification of a patient that may respond to a particular treatment regime or pharmaceutical agent, monitoring of the progress of treatment, and in the context of a screening assay, for the identification of an anti-aggressive prostate cancer therapeutic.

The terms "patient," "individual," or "subject" are used interchangeably herein, and refer to a mammal, particularly, a human. The patient may have mild, intermediate or severe disease. The patient may be treatment naïve, responding to any form of treatment, or refractory. The patient may be an individual in need of treatment or in need of diagnosis based on particular symptoms or family history. In some cases, the terms may refer to treatment in experimental animals, in veterinary application, and in the development of animal models for disease, including, but not limited to, rodents including mice, rats, and hamsters; and primates.

The terms "measuring" and "determining" are used interchangeably throughout, and refer to methods which include obtaining a patient sample and/or detecting the level of a biomarker(s) in a sample. In one embodiment, the terms refer to obtaining a patient sample and detecting the level of one or more biomarkers in the sample. In another embodiment, the terms "measuring" and "determining" mean detecting the level of one or more biomarkers in a patient sample. Measuring can be accomplished by methods known in the art and those further described herein. The term "measuring" is also used interchangeably throughout with the term "detecting."

The terms "sample," "patient sample," "biological sample," and the like, encompass a variety of sample types obtained from a patient, individual, or subject and can be used in a diagnostic or monitoring assay. The patient sample may be obtained from a healthy subject, a diseased patient or a patient having associated symptoms of aggressive prostate cancer. Moreover, a sample obtained from a patient can be divided and only a portion may be used for diagnosis. Further, the sample, or a portion thereof, can be stored under conditions to maintain sample for later analysis. The definition specifically encompasses blood and other liquid samples of biological origin (including, but not limited to, peripheral blood, serum, plasma, cerebrospinal fluid, urine, saliva, stool and synovial fluid), solid tissue samples such as a biopsy specimen or tissue cultures or cells derived therefrom and the progeny thereof. In a specific embodiment, a sample comprises a blood sample. In another embodiment, a sample comprises a plasma sample. In yet another embodiment, a serum sample is used.

The definition of "sample" also includes samples that have been manipulated in any way after their procurement, such as by centrifugation, filtration, precipitation, dialysis, chromatography, treatment with reagents, washed, or enriched for certain cell populations. The terms further encompass a clinical sample, and also include cells in culture, cell supernatants, tissue samples, organs, and the like. Samples may also comprise fresh-frozen and/or formalin-fixed, paraffin-embedded tissue blocks, such as blocks prepared from clinical or pathological biopsies, prepared for pathological analysis or study by immunohistochemistry. In certain embodiments, a sample comprises an optimal cutting temperature (OCT)-embedded frozen tissue sample.

The terms "specifically binds to," "specific for," and related grammatical variants refer to that binding which occurs between such paired species as enzyme/substrate, receptor/agonist, antibody/antigen, and lectin/carbohydrate which may be mediated by covalent or non-covalent interactions or a combination of covalent and non-covalent interactions. When the interaction of the two species produces a non-covalently bound complex, the binding which occurs is typically electrostatic, hydrogen-bonding, or the result of lipophilic interactions. Accordingly, "specific binding" occurs between a paired species where there is interaction between the two which produces a bound complex having the characteristics of an antibody/antigen or enzyme/substrate interaction. In particular, the specific binding is characterized by the binding of one member of a pair to a particular species and to no other species within the family of compounds to which the corresponding member of the binding member belongs. Thus, for example, an antibody typically binds to a single epitope and to no other epitope within the family of proteins. In some embodiments, specific binding between an antigen and an antibody will have a binding affinity of at least $10^{-6}$ M. In other embodiments, the antigen and antibody will bind with affinities of at least $10^{-2}$ M, $10^{-8}$ M to $10^{-9}$ M, $10^{-10}$ M, $10^{-11}$ M, or $10^{-12}$ M.

Various methodologies of the instant invention include a step that involves comparing a value, level, feature, characteristic, property, etc. to a "suitable control," referred to interchangeably herein as an "appropriate control" or a "control sample." A "suitable control," "appropriate control" or a "control sample" is any control or standard familiar to one of ordinary skill in the art useful for comparison purposes. In one embodiment, a "suitable control" or "appropriate control" is a value, level, feature, characteristic, property, etc., determined in a cell, organ, or patient, e.g., a control or normal cell, organ, or patient, exhibiting, for example, normal traits. For example, the biomarkers of the present invention may be assayed for levels/ratios in a sample from an unaffected individual (UI) or a normal control individual (NC) (both terms are used interchangeably herein). In another embodiment, a "suitable control" or "appropriate control" is a value, level, feature, characteristic, property, ratio, etc. determined prior to performing a therapy (e.g., aggressive prostate cancer treatment) on a patient. In yet another embodiment, a transcription rate, mRNA level, translation rate, protein level/ratio, biological activity, cellular characteristic or property, genotype, phenotype, etc., can be determined prior to, during, or after administering a therapy into a cell, organ, or patient. In a further embodiment, a "suitable control" or "appropriate control" is a predefined value, level, feature, characteristic, property, ratio, etc. A "suitable control" can be a profile or pattern of levels/ratios of one or more biomarkers of the present invention that correlates to aggressive prostate cancer, to which a patient sample can be compared. The patient sample can also be compared to a negative control, i.e., a profile that correlates to not having aggressive prostate cancer.

II. DETECTION OF AGGRESSIVE PROSTATE CANCER BIOMARKERS

A. Detection by Mass Spectrometry

In one aspect, the biomarkers of the present invention may be detected by mass spectrometry, a method that employs a mass spectrometer to detect gas phase ions. Examples of mass spectrometers are time-of-flight, magnetic sector, quadrupole filter, ion trap, ion cyclotron resonance, Orbitrap, hybrids or combinations of the foregoing, and the like.

In particular embodiments, the biomarkers of the present invention are detected using selected reaction monitoring (SRM) mass spectrometry techniques. Selected reaction monitoring (SRM) is a non-scanning mass spectrometry technique, performed on triple quadrupole-like instruments and in which collision-induced dissociation is used as a means to increase selectivity. In SRM experiments two mass analyzers are used as static mass filters, to monitor a particular fragment ion of a selected precursor ion. The specific pair of mass-over-charge (m/z) values associated to the precursor and fragment ions selected is referred to as a "transition" and can be written as parent m/z→fragment m/z (e.g. 673.5→534.3). Unlike common MS based proteomics, no mass spectra are recorded in a SRM analysis. Instead, the detector acts as counting device for the ions matching the selected transition thereby returning an intensity distribution over time. Multiple SRM transitions can be measured within the same experiment on the chromatographic time scale by rapidly toggling between the different precursor/fragment pairs (sometimes called multiple reaction monitoring, MRM). Typically, the triple quadrupole instrument cycles through a series of transitions and records the signal of each transition as a function of the elution time. The method allows for additional selectivity by monitoring the chromatographic coelution of multiple transitions for a given analyte. The terms SRM/MRM are occasionally used also to describe experiments conducted in mass spectrometers other than triple quadrupoles (e.g. in trapping instruments) where upon fragmentation of a specific precursor ion a narrow mass range is scanned in MS2 mode, centered on a fragment ion specific to the precursor of interest or in general in experiments where fragmentation in the collision cell is used as a means to increase selectivity. In this application, the terms SRM and MRM or also SRM/MRM can be used interchangeably, since they both refer to the same mass spectrometer operating principle. As a matter of clarity, the term MRM is used throughout the text, but the term includes both SRM and MRM, as well as any analogous technique, such as e.g. highly-selective reaction monitoring, hSRM, LC-SRM or any other SRM/MRM-like or SRM/MRM-mimicking approaches performed on any type of mass spectrometer and/or, in which the peptides are fragmented using any other fragmentation method such as e.g. CAD (collision-activated dissociation (also known as CID or collision-induced dissociation), HCD (higher energy CID), ECD (electron capture dissociation), PD (photodissociation) or ETD (electron transfer dissociation).

In another specific embodiment, the mass spectrometric method comprises matrix assisted laser desorption/ionization time-of-flight (MALDI-TOF MS or MALDI-TOF). In another embodiment, method comprises MALDI-TOF tandem mass spectrometry (MALDI-TOF MS/MS). In yet another embodiment, mass spectrometry can be combined with another appropriate method(s) as may be contemplated by one of ordinary skill in the art. For example, MALDI-TOF can be utilized with trypsin digestion and tandem mass spectrometry as described herein.

In an alternative embodiment, the mass spectrometric technique comprises surface enhanced laser desorption and ionization or "SELDI," as described, for example, in U.S. Pat. No. 6,225,047 and No. 5,719,060. Briefly, SELDI refers to a method of desorption/ionization gas phase ion spectrometry (e.g. mass spectrometry) in which an analyte (here, one or more of the biomarkers) is captured on the surface of a SELDI mass spectrometry probe. There are several versions of SELDI that may be utilized including, but not limited to, Affinity Capture Mass Spectrometry (also called Surface-Enhanced Affinity Capture (SEAC)), and Surface-Enhanced Neat Desorption (SEND) which involves the use of probes comprising energy absorbing molecules that are chemically bound to the probe surface (SEND probe). Another SELDI method is called Surface-Enhanced Photolabile Attachment and Release (SEPAR), which involves the use of probes having moieties attached to the surface that can covalently bind an analyte, and then release the analyte through breaking a photolabile bond in the moiety after exposure to light, e.g., to laser light (see, U.S. Pat. No. 5,719,060). SEPAR and other forms of SELDI are readily adapted to detecting a biomarker or biomarker panel, pursuant to the present invention.

In another mass spectrometry method, the biomarkers can be first captured on a chromatographic resin having chromatographic properties that bind the biomarkers. For example, one could capture the biomarkers on a cation exchange resin, such as CM Ceramic HyperD F resin, wash the resin, elute the biomarkers and detect by MALDI. Alternatively, this method could be preceded by fractionating the sample on an anion exchange resin before application to the cation exchange resin. In another alternative, one could fractionate on an anion exchange resin and detect by MALDI directly. In yet another method, one could capture the biomarkers on an immuno-chromatographic resin that comprises antibodies that bind the biomarkers, wash the resin to remove unbound material, elute the biomarkers from the resin and detect the eluted biomarkers by MALDI or by SELDI.

B. Detection by Immunoassay

In other embodiments, the biomarkers of the present invention can be detected and/or measured by immunoassay Immunoassay requires biospecific capture reagents, such as antibodies, to capture the biomarkers. Many antibodies are available commercially. Antibodies also can be produced by methods well known in the art, e.g., by immunizing animals with the biomarkers. Biomarkers can be isolated from samples based on their binding characteristics. Alternatively, if the amino acid sequence of a polypeptide biomarker is known, the polypeptide can be synthesized and used to generate antibodies by methods well-known in the art.

The present invention contemplates traditional immunoassays including, for example, sandwich immunoassays including ELISA or fluorescence-based immunoassays, immunoblots, Western Blots (WB), as well as other enzyme immunoassays. Nephelometry is an assay performed in liquid phase, in which antibodies are in solution. Binding of the antigen to the antibody results in changes in absorbance, which is measured. In a SELDI-based immunoassay, a biospecific capture reagent for the biomarker is attached to the surface of an MS probe, such as a pre-activated protein chip array. The biomarker is then specifically captured on the biochip through this reagent, and the captured biomarker is detected by mass spectrometry.

Although antibodies are useful because of their extensive characterization, any other suitable agent (e.g., a peptide, an aptamer, lectin, or a small organic molecule) that specifically binds a biomarker of the present invention is optionally used in place of the antibody in the above described immunoassays. For example, an aptamer that specifically binds all neurogranin and/or one or more of its breakdown products might be used. Aptamers are nucleic acid-based molecules that bind specific ligands. Methods for making aptamers with a particular binding specificity are known as detailed in U.S. Pat. No. 5,475,096; No. 5,670,637; No. 5,696,249; No.

5,270,163; No. 5,707,796; No. 5,595,877; No. 5,660,985; No. 5,567,588; No. 5,683,867; No. 5,637,459; and No. 6,011,020.

C. Detection by Electrochemicaluminescent Assay

In several embodiments, the biomarker biomarkers of the present invention may be detected by means of an electrochemicaluminescent assay developed by Meso Scale Discovery (Gaithersrburg, Md.). Electrochemiluminescence detection uses labels that emit light when electrochemically stimulated. Background signals are minimal because the stimulation mechanism (electricity) is decoupled from the signal (light). Labels are stable, non-radioactive and offer a choice of convenient coupling chemistries. They emit light at ~620 nm, eliminating problems with color quenching. See U.S. Pat. No. 7,497,997; No. 7,491,540; No. 7,288,410; No. 7,036,946; No. 7,052,861; No. 6,977,722; No. 6,919,173; No. 6,673,533; No. 6,413,783; No. 6,362,011; No. 6,319,670; No. 6,207,369; No. 6,140,045; No. 6,090,545; and No. 5,866,434. See also U.S. Patent Applications Publication No. 2009/0170121; No. 2009/006339; No. 2009/0065357; No. 2006/0172340; No. 2006/0019319; No. 2005/0142033; No. 2005/0052646; No. 2004/0022677; No. 2003/0124572; No. 2003/0113713; No. 2003/0003460; No. 2002/0137234; No. 2002/0086335; and No. 2001/0021534.

D. Other Methods for Detecting Biomarkers

The biomarkers of the present invention can be detected by other suitable methods. Detection paradigms that can be employed to this end include optical methods, electrochemical methods (voltametry and amperometry techniques), atomic force microscopy, and radio frequency methods, e.g., multipolar resonance spectroscopy. Illustrative of optical methods, in addition to microscopy, both confocal and non-confocal, are detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

Furthermore, a sample may also be analyzed by means of a biochip. Biochips generally comprise solid substrates and have a generally planar surface, to which a capture reagent (also called an adsorbent or affinity reagent) is attached. Frequently, the surface of a biochip comprises a plurality of addressable locations, each of which has the capture reagent bound there. Protein biochips are biochips adapted for the capture of polypeptides. Many protein biochips are described in the art. These include, for example, protein biochips produced by Ciphergen Biosystems, Inc. (Fremont, Calif.), Invitrogen Corp. (Carlsbad, Calif.), Affymetrix, Inc. (Fremong, Calif.), Zyomyx (Hayward, Calif.), R&D Systems, Inc. (Minneapolis, Minn.), Biacore (Uppsala, Sweden) and Procognia (Berkshire, UK). Examples of such protein biochips are described in the following patents or published patent applications: U.S. Pat. No. 6,537,749; U.S. Pat. No. 6,329,209; U.S. Pat. No. 6,225,047; U.S. Pat. No. 5,242,828; PCT International Publication No. WO 00/56934; and PCT International Publication No. WO 03/048768.

III. DETERMINATION OF A PATIENT'S AGGRESSIVE PROSTATE CANCER STATUS

A. The present invention relates to the use of biomarkers to diagnose aggressive prostate cancer. More specifically, the biomarkers of the present invention can be used in diagnostic tests to determine, qualify, and/or assess aggressive prostate cancer or status, for example, to diagnose aggressive prostate cancer, in an individual, subject or patient. In particular embodiments, aggressive prostate cancer status can include determining a patient's aggressive prostate cancer status, for example, to diagnose aggressive prostate cancer, in an individual, subject or patient. More specifically, the biomarkers to be detected in diagnosing aggressive prostate cancer include cathepsin-L (CTSL), periostin, microfibrillar-associated protein 4 (MFAP4), collagen XII, neprilysin, clusterin, neutrophil gelatinase associated lipocalin (NGAL), epithelial cell activating molecule (EpCAM), prostate specific antigen (PSA), membrane metallo-endopeptidase (MME) and asporin (ASPN). FIGS. 6, 7 and 9 also list biomarkers useful in the methods of the present invention. Other biomarkers known in the relevant art may be used in combination with the biomarkers described herein.

B. Biomarker Panels

The biomarkers of the present invention can be used in diagnostic tests to assess, determine, and/or qualify (used interchangeably herein) aggressive prostate cancer status in a patient. The phrase "aggressive prostate cancer status" includes any distinguishable manifestation of the condition, including not having aggressive prostate cancer. For example, aggressive prostate cancer status includes, without limitation, the presence or absence of aggressive prostate cancer in a patient, the risk of developing aggressive prostate cancer, the stage or severity of aggressive prostate cancer, the progress of aggressive prostate cancer (e.g., progress of aggressive prostate cancer over time) and the effectiveness or response to treatment of aggressive prostate cancer (e.g., clinical follow up and surveillance of aggressive prostate cancer after treatment). Based on this status, further procedures may be indicated, including additional diagnostic tests or therapeutic procedures or regimens.

The power of a diagnostic test to correctly predict status is commonly measured as the sensitivity of the assay, the specificity of the assay or the area under a receiver operated characteristic ("ROC") curve. Sensitivity is the percentage of true positives that are predicted by a test to be positive, while specificity is the percentage of true negatives that are predicted by a test to be negative. An ROC curve provides the sensitivity of a test as a function of 1-specificity. The greater the area under the ROC curve, the more powerful the predictive value of the test. Other useful measures of the utility of a test are positive predictive value and negative predictive value. Positive predictive value is the percentage of people who test positive that are actually positive. Negative predictive value is the percentage of people who test negative that are actually negative.

In particular embodiments, the biomarker panels of the present invention may show a statistical difference in different aggressive prostate cancer statuses of at least $p<0.05$, $p<10^{-2}$, $p<10^{-3}$, $p<10^{-4}$ or $p<10^{-5}$. Diagnostic tests that use these biomarkers may show an ROC of at least 0.6, at least about 0.7, at least about 0.8, or at least about 0.9.

The biomarkers can be differentially present in UI (NC or non-aggressive prostate cancer) and aggressive prostate cancer, and, therefore, are useful in aiding in the determination of aggressive prostate cancer status. In certain embodiments, the biomarkers are measured in a patient sample using the methods described herein and compared, for example, to predefined biomarker levels/ratios and correlated to aggressive prostate cancer status. In particular embodiments, the measurement(s) may then be compared with a relevant diagnostic amount(s), cut-off(s), or multivariate model scores that distinguish a positive aggressive prostate cancer status from a negative aggressive prostate cancer status. The diagnostic amount(s) represents a measured amount of a biomarker(s) above which or below which a patient is classified as having a particular aggressive prostate cancer status. For example, if the biomarker(s) is/are up-regulated compared to normal (e.g., no cancer or non-aggressive prostate cancer) during aggressive prostate cancer, then a measured amount(s) above the diagnostic cutoff(s) provides a diagnosis of aggressive prostate cancer. Alternatively, if the biomarker(s) is/are down-regulated during aggressive prostate cancer, then a measured amount(s) at or below the diagnostic cutoff(s) provides a diagnosis of non-aggressive prostate cancer. The opposite may hold true as well (i.e., expression of the biomarker is lower/downregulated in progressive prostate cancer vs. no cancer or non-aggressive prostate cancer) As is well understood in the art, by adjusting the particular diagnostic cut-off(s) used in an assay, one can increase sensitivity or specificity of the diagnostic assay depending on the preference of the diagnostician. In particular embodiments, the particular diagnostic cut-off can be determined, for example, by measuring the amount of biomarkers in a statistically significant number of samples from patients with the different aggressive prostate cancer statuses, and drawing the cut-off to suit the desired levels of specificity and sensitivity.

In other embodiments, ratios of post-translationally modified biomarkers (e.g., glycosylated, citrullination, oxidation, methylation, phosphorylation, cysteinylation s-nitrosation, s-glutathyolation, or a combination thereof) to the corresponding unmodified biomarkers are useful in aiding in the determination of aggressive prostate cancer status. In certain embodiments, the biomarker ratios are indicative of diagnosis. In other embodiments, a biomarker ratio can be compared to another biomarker ration in the same sample or to a set of biomarker ratios from a control or reference sample.

Indeed, as the skilled artisan will appreciate there are many ways to use the measurements of two or more biomarkers in order to improve the diagnostic question under investigation. In a quite simple, but nonetheless often effective approach, a positive result is assumed if a sample is positive for at least one of the markers investigated.

Furthermore, in certain embodiments, the values measured for markers of a biomarker panel are mathematically combined and the combined value is correlated to the underlying diagnostic question. Biomarker values may be combined by any appropriate state of the art mathematical method. Well-known mathematical methods for correlating a marker combination to a disease status employ methods like discriminant analysis (DA) (e.g., linear-, quadratic-, regularized-DA), Discriminant Functional Analysis (DFA), Kernel Methods (e.g., SVM), Multidimensional Scaling (MDS), Nonparametric Methods (e.g., k-Nearest-Neighbor Classifiers), PLS (Partial Least Squares), Tree-Based Methods (e.g., Logic Regression, CART, Random Forest Methods, Boosting/Bagging Methods), Generalized Linear Models (e.g., Logistic Regression), Principal Components based Methods (e.g., SIMCA), Generalized Additive Models, Fuzzy Logic based Methods, Neural Networks and Genetic Algorithms based Methods. The skilled artisan will have no problem in selecting an appropriate method to evaluate a biomarker combination of the present invention. In one embodiment, the method used in a correlating a biomarker combination of the present invention, e.g. to diagnose aggressive prostate cancer, is selected from DA (e.g., Linear-, Quadratic-, Regularized Discriminant Analysis), DFA, Kernel Methods (e.g., SVM), MDS, Nonparametric Methods (e.g., k-Nearest-Neighbor Classifiers), PLS (Partial Least Squares), Tree-Based Methods (e.g., Logic Regression, CART, Random Forest Methods, Boosting Methods), or Generalized Linear Models (e.g., Logistic Regression), and Principal Components Analysis. Details relating to these statistical methods are found in the following references: Ruczinski et al., 12 J. OF COMPUTATIONAL AND GRAPHICAL STATISTICS 475-511 (2003); Friedman, J. H., 84 J. OF THE AMERICAN STATISTICAL ASSOCIATION 165-75 (1989); Hastie, Trevor, Tibshirani, Robert, Friedman, Jerome, The Elements of Statistical Learning, Springer Series in Statistics (2001); Breiman, L., Friedman, J. H., Olshen, R. A., Stone, C. J. Classification and regression trees, California: Wadsworth (1984); Breiman, L., 45 MACHINE LEARNING 5-32 (2001); Pepe, M. S., The Statistical Evaluation of Medical Tests for Classification and Prediction, Oxford Statistical Science Series, 28 (2003); and Duda, R. O., Hart, P. E., Stork, D. G., Pattern Classification, Wiley Interscience, 2nd Edition (2001).

C. Determining Risk of Developing Aggressive Prostate Cancer

In a specific embodiment, the present invention provides methods for determining the risk of developing aggressive prostate cancer in a patient. Biomarker percentages, ratios, amounts or patterns are characteristic of various risk states, e.g., high, medium or low. The risk of developing aggressive prostate cancer is determined by measuring the relevant biomarkers and then either submitting them to a classification algorithm or comparing them with a reference amount, i.e., a predefined level or pattern of biomarkers that is associated with the particular risk level.

D. Determining Aggressive Prostate Cancer Severity

In another embodiment, the present invention provides methods for determining the severity of aggressive prostate cancer in a patient. Each grade or stage of aggressive prostate cancer likely has a characteristic level of a biomarker or relative levels/ratios of a set of biomarkers (a pattern or ratio). The severity of aggressive prostate cancer is determined by measuring the relevant biomarkers and then either submitting them to a classification algorithm or comparing them with a reference amount, i.e., a predefined level or pattern of biomarkers that is associated with the particular stage.

E. Determining Aggressive Prostate Cancer Prognosis

In one embodiment, the present invention provides methods for determining the course of aggressive prostate cancer in a patient. Aggressive prostate cancer course refers to changes in aggressive prostate cancer status over time, including aggressive prostate cancer progression (worsening) and aggressive prostate cancer regression (improvement). Over time, the amount or relative amount (e.g., the pattern or ratio) of the biomarkers changes. For example, biomarker "X" may be increased with aggressive prostate cancer, while biomarker "Y" may be decreased with aggressive prostate cancer. Therefore, the trend of these biomarkers, either increased or decreased over time toward aggressive prostate cancer or non-aggressive prostate cancer indicates the course of the condition. Accordingly, this method involves measuring the level of one or more biomarkers in a patient at least two different time points, e.g., a first time and a second time, and comparing the change, if any. The course of aggressive prostate cancer is determined based on these comparisons.

F. Patient Management

In certain embodiments of the methods of qualifying aggressive prostate cancer status, the methods further comprise managing patient treatment based on the status. Such management includes the actions of the physician or clinician subsequent to determining aggressive prostate cancer status. For example, if a physician makes a diagnosis of aggressive prostate cancer, then a certain regime of monitoring would follow. An assessment of the course of aggressive prostate cancer using the methods of the present invention may then require a certain aggressive prostate cancer therapy regimen. Alternatively, a diagnosis of non-aggressive prostate cancer might be followed with further testing to determine a specific disease that the patient might be suffering from. Also, further tests may be called for if the diagnostic test gives an inconclusive result on aggressive prostate cancer status.

G. Determining Therapeutic Efficacy of Pharmaceutical Drug

In another embodiment, the present invention provides methods for determining the therapeutic efficacy of a pharmaceutical drug. These methods are useful in performing clinical trials of the drug, as well as monitoring the progress of a patient on the drug. Therapy or clinical trials involve administering the drug in a particular regimen. The regimen may involve a single dose of the drug or multiple doses of the drug over time. The doctor or clinical researcher monitors the effect of the drug on the patient or subject over the course of administration. If the drug has a pharmacological impact on the condition, the amounts or relative amounts (e.g., the pattern, profile or ratio) of one or more of the biomarkers of the present invention may change toward a non-aggressive prostate cancer profile. Therefore, one can follow the course of one or more biomarkers in the patient during the course of treatment. Accordingly, this method involves measuring one or more biomarkers in a patient receiving drug therapy, and correlating the biomarker levels/ratios with the aggressive prostate cancer status of the patient (e.g., by comparison to predefined levels/ratios of the biomarkers that correspond to different aggressive prostate cancer statuses). One embodiment of this method involves determining the levels/ratios of one or more biomarkers for at least two different time points during a course of drug therapy, e.g., a first time and a second time, and comparing the change in levels/ratios of the biomarkers, if any. For example, the levels/ratios of one or more biomarkers can be measured before and after drug administration or at two different time points during drug administration. The effect of therapy is determined based on these comparisons. If a treatment is effective, then the level/ratio of one or more biomarkers will trend toward normal, while if treatment is ineffective, the level/ratio of one or more biomarkers will trend toward aggressive prostate cancer indications.

H. Generation of Classification Algorithms for Qualifying Aggressive Prostate Cancer Status In some embodiments, data that are generated using samples such as "known samples" can then be used to "train" a classification model. A "known sample" is a sample that has been pre-classified. The data that are used to form the classification model can be referred to as a "training data set." The training data set that is used to form the classification model may comprise raw data or pre-processed data. Once trained, the classification model can recognize patterns in data generated using unknown samples. The classification model can then be used to classify the unknown samples into classes. This can be useful, for example, in predicting whether or not a particular biological sample is associated with a certain biological condition (e.g., diseased versus non-diseased).

Classification models can be formed using any suitable statistical classification or learning method that attempts to segregate bodies of data into classes based on objective parameters present in the data. Classification methods may be either supervised or unsupervised. Examples of supervised and unsupervised classification processes are described in Jain, "Statistical Pattern Recognition: A Review", IEEE Transactions on Pattern Analysis and Machine Intelligence, Vol. 22, No. 1, January 2000, the teachings of which are incorporated by reference.

In supervised classification, training data containing examples of known categories are presented to a learning mechanism, which learns one or more sets of relationships that define each of the known classes. New data may then be applied to the learning mechanism, which then classifies the new data using the learned relationships. Examples of supervised classification processes include linear regression processes (e.g., multiple linear regression (MLR), partial least squares (PLS) regression and principal components regression (PCR)), binary decision trees (e.g., recursive partitioning processes such as CART), artificial neural networks such as back propagation networks, discriminant analyses (e.g., Bayesian classifier or Fischer analysis), logistic classifiers, and support vector classifiers (support vector machines).

Another supervised classification method is a recursive partitioning process. Recursive partitioning processes use recursive partitioning trees to classify data derived from unknown samples. Further details about recursive partitioning processes are provided in U.S. Patent Application No. 2002 0138208 A1 to Paulse et al., "Method for analyzing mass spectra."

In other embodiments, the classification models that are created can be formed using unsupervised learning methods. Unsupervised classification attempts to learn classifications based on similarities in the training data set, without pre-classifying the spectra from which the training data set was derived. Unsupervised learning methods include cluster analyses. A cluster analysis attempts to divide the data into "clusters" or groups that ideally should have members that are very similar to each other, and very dissimilar to members of other clusters. Similarity is then measured using some distance metric, which measures the distance between data items, and clusters together data items that are closer to each other. Clustering techniques include the MacQueen's K-means algorithm and the Kohonen's Self-Organizing Map algorithm.

Learning algorithms asserted for use in classifying biological information are described, for example, in PCT International Publication No. WO 01/31580 (Barnhill et al., "Methods and devices for identifying patterns in biological systems and methods of use thereof"), U.S. Patent Application Publication No. 2002/0193950 (Gavin et al. "Method or analyzing mass spectra"), U.S. Patent Application Publication No. 2003/0004402 (Hitt et al., "Process for discriminating between biological states based on hidden patterns from biological data"), and U.S. Patent Application Publication No. 2003/0055615 (Zhang and Zhang, "Systems and methods for processing biological expression data").

The classification models can be formed on and used on any suitable digital computer. Suitable digital computers include micro, mini, or large computers using any standard or specialized operating system, such as a Unix, Windows® or Linux™ based operating system. In embodiments utilizing a mass spectrometer, the digital computer that is used may be physically separate from the mass spectrometer that is used to create the spectra of interest, or it may be coupled to the mass spectrometer.

The training data set and the classification models according to embodiments of the invention can be embodied by computer code that is executed or used by a digital computer. The computer code can be stored on any suitable computer readable media including optical or magnetic disks, sticks, tapes, etc., and can be written in any suitable computer programming language including R, C, C++, visual basic, etc.

The learning algorithms described above are useful both for developing classification algorithms for the biomarkers already discovered, and for finding new biomarker biomarkers. The classification algorithms, in turn, form the base for diagnostic tests by providing diagnostic values (e.g., cut-off points) for biomarkers used singly or in combination.

IV. KITS FOR THE DETECTION OF AGGRESSIVE PROSTATE CANCER BIOMARKERS

In another aspect, the present invention provides kits for qualifying aggressive prostate cancer status, which kits are used to detect the biomarkers described herein. In a specific embodiment, the kit is provided as an ELISA kit comprising antibodies to the biomarkers of the present invention including, but not limited to, CTSL, periostin, MFAP4, collagen XII, neprilysin, clusterin, NGAL, EpCAM, PSA MME, ASPN, as well as the proteins/peptides listed in FIGS. 6, 7 and 9, and combinations of all of the foregoing.

The ELISA kit may comprise a solid support, such as a chip, microtiter plate (e.g., a 96-well plate), bead, or resin having biomarker capture reagents attached thereon. The kit may further comprise a means for detecting the biomarkers, such as antibodies, and a secondary antibody-signal complex such as horseradish peroxidase (HRP)-conjugated goat anti-rabbit IgG antibody and tetramethyl benzidine (TMB) as a substrate for HRP.

The kit for qualifying aggressive prostate cancer status may be provided as an immuno-chromatography strip comprising a membrane on which the antibodies are immobilized, and a means for detecting, e.g., gold particle bound antibodies, where the membrane, includes NC membrane and PVDF membrane. The kit may comprise a plastic plate on which a sample application pad, gold particle bound antibodies temporally immobilized on a glass fiber filter, a nitrocellulose membrane on which antibody bands and a secondary antibody band are immobilized and an absorbent pad are positioned in a serial manner, so as to keep continuous capillary flow of blood serum.

In certain embodiments, a patient can be diagnosed by adding blood or blood serum from the patient to the kit and detecting the relevant biomarkers conjugated with antibodies, specifically, by a method which comprises the steps of: (i) collecting blood or blood serum from the patient; (ii) separating blood serum from the patient's blood; (iii) adding the blood serum from patient to a diagnostic kit; and, (iv) detecting the biomarkers conjugated with antibodies. In this method, the antibodies are brought into contact with the patient's blood. If the biomarkers are present in the sample, the antibodies will bind to the sample, or a portion thereof. In other kit and diagnostic embodiments, blood or blood serum need not be collected from the patient (i.e., it is already collected). Moreover, in other embodiments, the sample may comprise a tissue sample or a clinical sample.

The kit can also comprise a washing solution or instructions for making a washing solution, in which the combination of the capture reagents and the washing solution allows capture of the biomarkers on the solid support for subsequent detection by, e.g., antibodies or mass spectrometry. In a further embodiment, a kit can comprise instructions for suitable operational parameters in the form of a label or separate insert. For example, the instructions may inform a consumer about how to collect the sample, how to wash the probe or the particular biomarkers to be detected, etc. In yet another embodiment, the kit can comprise one or more containers with biomarker samples, to be used as standard(s) for calibration.

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Materials and Methods

Materials.

Hydrazide resin and sodium periodate were from Bio-Rad (Hercules, Calif.); sequencing grade trypsin was purchased from Promega (Madison, Wis.); PNGase F was from New England Biolabs (Ipswich, Mass.); C18 columns were from Waters (Milford, Mass.); iTRAQ reagent was from Applied Biosystems (Foster City, Calif.); rabbit antihuman periostin antibody and mouse antihuman cathepsin L antibody for Western blot analysis were from Abcam (Cambridge, U.K.); goat anticathepsin L antibody for immunohistochemistry was from R&D systems (Minneapolis, Minn.); BCA assay kit, HRP-labeled secondary antibodies, and the Novex ECL Chemiluminescent Substrate Reagent Kit were from Pierce (Rockford, Ill.); LSAB+ System-AP kit from Dako (Carpinteria, Calif.); and all other chemicals were purchased from Sigma-Aldrich (St. Louis, Mo.).

Prostate Cancer Tissues.

Samples and clinical information were obtained as part of a Johns Hopkins Medicine IRB approved study. Tissues from four nonaggressive and four aggressive primary prostate tumors were analyzed. The nonaggressive and aggressive primary cancer tissues were collected from radical prostatectomy specimens at Johns Hopkins Hospital and Johns Hopkins Bayview Medical Center. Under the NCI-funded Johns Hopkins prostate cancer SPORE project, annual follow-up data is obtained from consenting subjects, allowing clinical follow up data to be used in conjunction with pathologic data. The cancer tissues were selected from cases with known Gleason score and clinical outcome following surgery. The nonaggressive cancer tissues were microdisected from primary tissues with radical prostatectomy Gleason scores of 3+3=6 and without evidence of cancer recurrence (by PSA or other clinical data) after 11-15 years of follow-up. The aggressive cancer tissues were similarly microdissected from primary tissues of tumors with Gleason scores of 5+4=9 (3 cases) or 5+3=8 (one case) and either seminal vesicle or pelvic lymph node involvement (or both). Two of the men with aggressive prostate cancer died of prostate cancer 2 and 6 years after surgery, 1 died of myocardial infarction 5 years after surgery with known prostate cancer recurrence, and 1 is thought to have been surgically cured of aggressive prostate cancer as he shows no evidence of recurrence 15 years after surgery.

Glycopeptide Isolation.

OCT-embedded prostate frozen tissues were sectioned and stained with hematoxylin and eosin. The microscopic view of a histologic specimen was used for cryostat microdissection to remove the nontumor tissue. The proteins from each prostate cancer tissue were collected from one 10 μm OCT tumor section using lysis buffer (50 mM Tris, pH8.0, 150 mM NaCl, 0.1% SDS, 0.5% Na Deoxycholate, 1% Triton X 100). BCA assay was performed to determine the protein concentration. For each tissue specimen, 100 μg of proteins were used in the following experiment. Urea (8 M) and 5 mM TCEP as the final concentration were added to the sample and incubated at 60° C. for 2 h. Iodoaceta-mide (10 mM) as the final concentration was added to the sample and incubated for 30 min. at room temperature in the dark. The solution was diluted 8-fold with 100 mM $KH_2PO_4$ (pH 8.0). An amount of 2 μg of trypsin (Promega) was added to the solution and incubated at 37° C. overnight with shaking. Silver staining was used to determine whether the trypsin digestion was complete, which was indicated by the disappearance of the upper protein bands and appearance of lower peptide bands (<10 kDa). After trypsin digestion, samples were centrifuged at 13 000 rpm for 5 min to remove any particulate matter. The peptides were cleaned by C18 column and followed by N-linked glycopeptide isolation using the method of solid phase extraction of glycopeptides (SPEG). The enriched N-linked glycopeptides were concentrated by C18 columns and dried down and resuspended in 10 μL of 0.4% acetic acid.

iTRAQ Labeling.

Glycopeptides (10 μL) from each sample were labeled with iTRAQ 8plex (AB SCIEX) according to the manufacturer's instruction. Peptides of four AG-prostate tumors were labeled by iTRAQ with 113, 114, 115, and 121, respectively, while peptides of four NAG-prostate tumors were labeled by iTRAQ with 116, 117, 118, and 119. Labeled peptides were then mixed and cleaned by a SCX column.

LC-MS/MS Analysis.

iTRAQ labeled glycopeptides were separated on a C18 column (75 μm×10 cm, 5 μm, 120 Å, Magic C18, Microm-Bioresources, Auburn, Calif.) at 750 nL/min in 15 min loading time. The peptides were then eluted at 300 nL/min by using a gradient of 100 min at the voltage of 2.0 kV. Eluting peptides were sprayed into an LTQ Orbitrap Velos mass spectrometer (Thermo Scientific) with a 1 μm emitter tip (New Objective, Woburn, Mass.) using a 5-40% solution B (90% acetonitrile in 0.1% formic acid) gradient.

Identification of Protein and Glycosylation Sites.

MS/MS spectra were searched with MASCOT using Proteome Discoverer (version 1.0) (Thermo Fisher) against the human subdatabase of NCBI Reference Sequence (RefSeq) (version 40, released on Apr. 16, 2010) containing 29 704 sequences. The precursor mass tolerance was set as 15 ppm while the fragment mass tolerance was set as 0.05 Da. The enzyme was set to trypsin, allowing one missed cleavage, and the flexible modifications were set as deamidation (NQ) and oxidation (M). Carbamidomethylation (C) was set as a fixed modification. The criterion of peptide probability score is >0.95 (decoy target FDR, 0.05) so that low probability protein identifications can be filtered out. The N-linked glycosylation site is the Asp contained within the consensus N-linked glycosylation motif.

Statistical Analysis.

To determine whether there was a significant difference in the glycoproteins of the AG and NAG-prostate cancer groups, P-values of the iTRAQ tag intensities representing the different groups were calculated using two-tailed t-tests.

Western Blot Analysis.

A total of 25 μg of proteins was resolved on SDS-PAGE and transferred electrophoretically onto a 0.2 μm nitrocellulose membrane. The membrane was blocked by 5% nonfat milk/0.1% TBS-Tween 20 at room temperature for 2 h. The membrane was then probed with primary antibody (rabbit antihuman periostin at 1:2000, mouse antihuman cathepsin L at 1:200) at 4° C. overnight, followed by a three-time wash of 0.1% TBS-Tween 20. HRP conjugated secondary antibody was added at 1:2000 and incubated at room temperature for 1 h. Three washes of 0.1% TBS-Tween 20 were performed. The signal was visualized by a superSignal West Femto Maximum Sensitivity Substrate (Pierce).

Immunohistochemstry Staining.

Rabbit antihuman periostin and goat anti-antibody were used in a dilution of 1:500 and 1:50 to stain sections from formalin-fixed and paraffin-embedded tissue specimens and were detected using the Dako LSAB+ System-AP kit according to the manufacturer's instructions.

Results

Example 1

Quantitative Glycoproteomic Profiling of Aggressive (AG) Prostate Tumors and Nonaggressive (NAG) Prostate Tumors The scheme of the present study is shown in FIG. 1. Briefly, to identify glycoproteins associated with AG-prostate cancer, glycoproteins from OCT-embedded AG-prostate tumor and NAG-prostate tumor tissues were quantitatively analyzed. The candidate proteins were further verified using Western blot and immunohistochemistry.

Glycopeptides were isolated from four AG-prostate tumors and four NAG-prostate tumors using solid-phase extraction of glycopeptides (SPEG). To determine the relative abundance of glycoproteins in AG and NAG-prostate cancer tissues, the glycopeptides isolated from each specimen were labeled with iTRAQ prior to LC-MS/MS analysis. From mass spectrometry analysis of glycopeptides, 102 unique N-linked glycopeptides were identified with 95% confidence, representing 79 unique glycoproteins (FIG. 7).

Example 2

Glycoprotein Changes Associated with Aggressive Prostate Tumors

To identify the glycoproteins associated with aggressive prostate tumors, the relative abundance of each glycopeptide in tissues of four cases of AG prostate cancer and four cases of NAG-prostate cancer were determined by iTRAQ labeling and tandem mass spectrometry (FIG. 7). With the use of the peak intensity of the iTRAQ reporter tags which represented the relative abundance of the peptides, t tests were performed to identify the glycopeptides and the glycoproteins associated with AG-prostate tumors. According to iTRAQ results, glycopeptides from three glycoproteins, microfibrillar-associated protein 4, periostin, and cathepsin L, showed a significant difference between the AG-prostate cancer group (iTRAQ Tag 113, 114, 115, and 121) and the NAG-prostate cancer group (iTRAQ Tag 116, 117, 118, and 119) (with p-values of less than 0.05) (FIGS. 2, 5, 7 and 8). Two peptides, vDLEDFEnNTAYAk and fnGSVSFFR (lower case v, f, and k represent the iTRAQ labeled N-termini and Lys, lower case n in the nXT/S motif represents the formerly glycosylated Asp and deaminated after SPEG isolation), were identified from microfibrillar-associated protein 4. The quantitation of the two peptides was consistent: the average ratio of the AG-prostate tumor group vs the reference channel (iTRAQ tag 113, labeled as one of the AG-prostate tumors) was 1.29±0.22, while the average ratio of the NAG-prostate tumor group was 0.40±0.21.

Example 3

Verification of Glycoproteomic Results Using Western Blot

Figure 3:
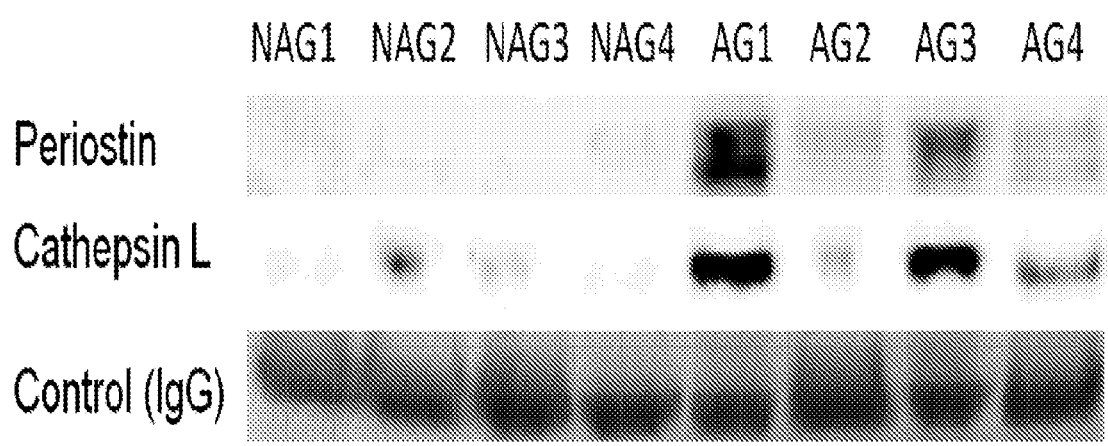
FIG. 3 presents the analysis of candidate proteins using Western blots. Periostin showed upregulated expression in all four AG-prostate tumors, while cathepsin L was upregulated in three out of four AG-prostate tumors, compared to NAG-prostate tumors. IgG was detected evenly in each sample and used as a quantitation control.

To verify the proteomic results, the four cases of AG-prostate tumors and four cases of NAG-prostate tumors were analyzed by Western blot assay. Periostin showed overexpression in all four AG-prostate tumors, while cathepsin L was elevated in three out of four AG-prostate tumors, compared to the NAG-prostate tumors (FIG. 3). A specific band for microfibrillar-associated protein 4 could not be identified by Western blot to verify its expression. IgG was detected evenly in each sample and was used as a quantitation control. These observations supported the glycoproteomic results for periostin and cathepsin L.

Example 4

Analysis of Overexpressed Proteins Using Immunohistochemistry

Figure 4:
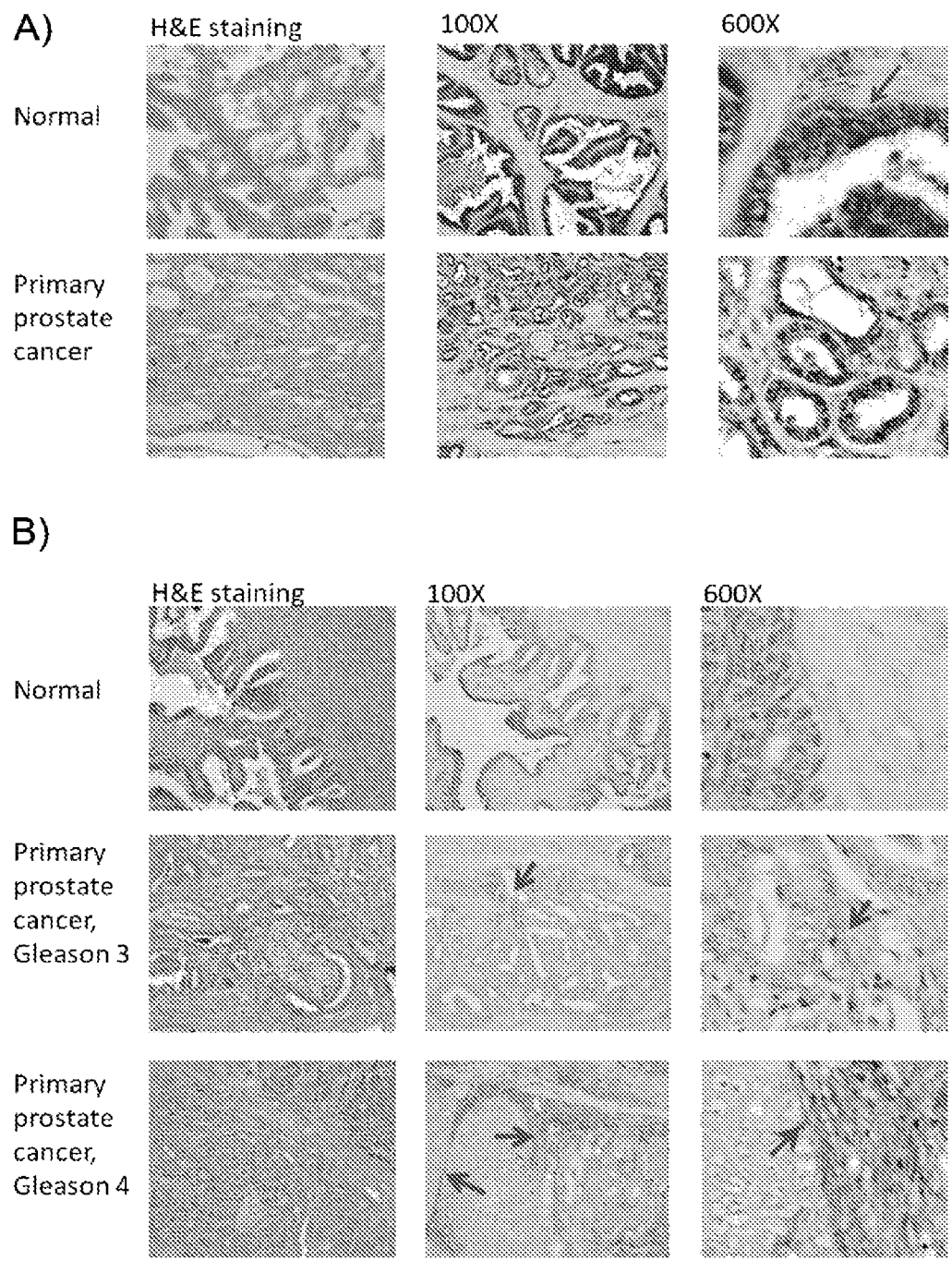
FIG. 4 shows the analysis of identified proteins using immunohistochemistry.
Figure 8A:
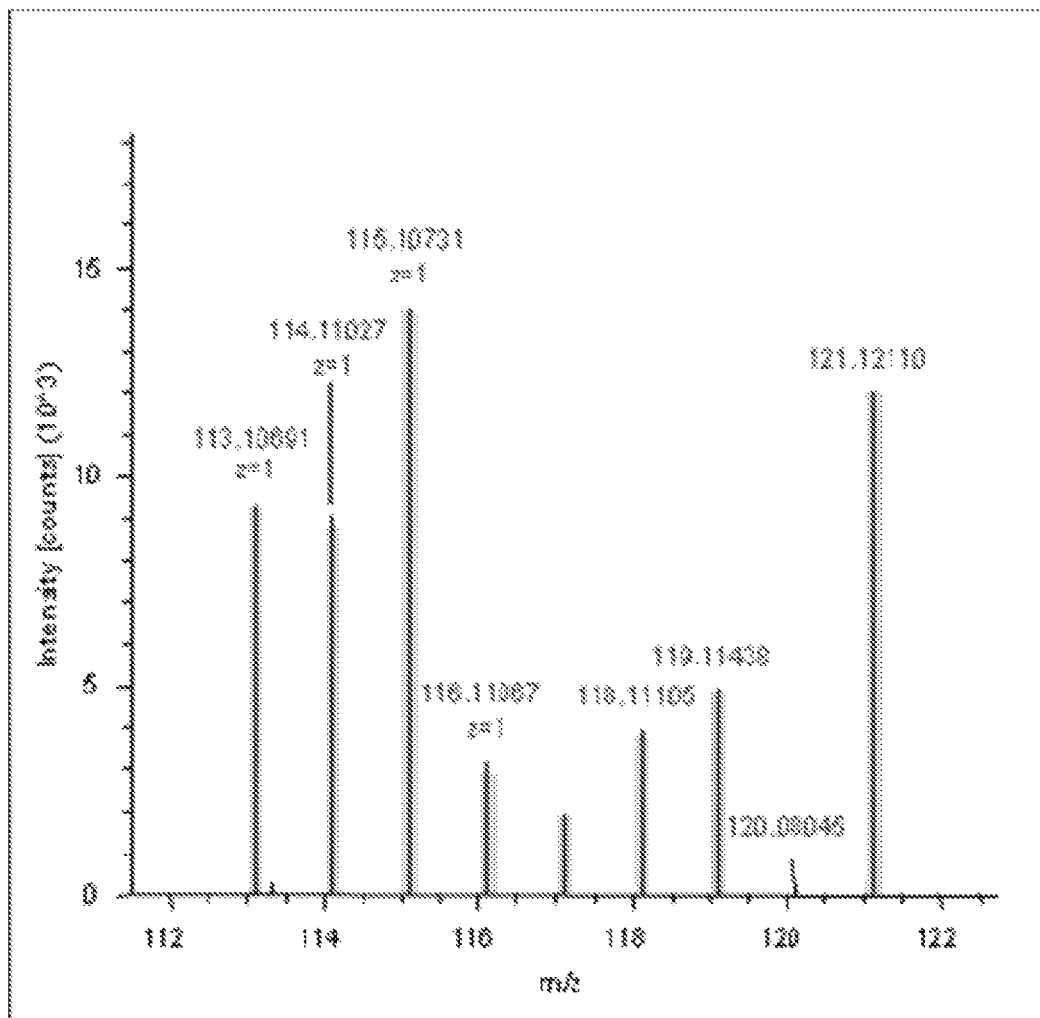
FIG. 8A: microfibrillar-associated protein 4 (peptide: vDLEDFEnNTAYAk)
Figure 8B:
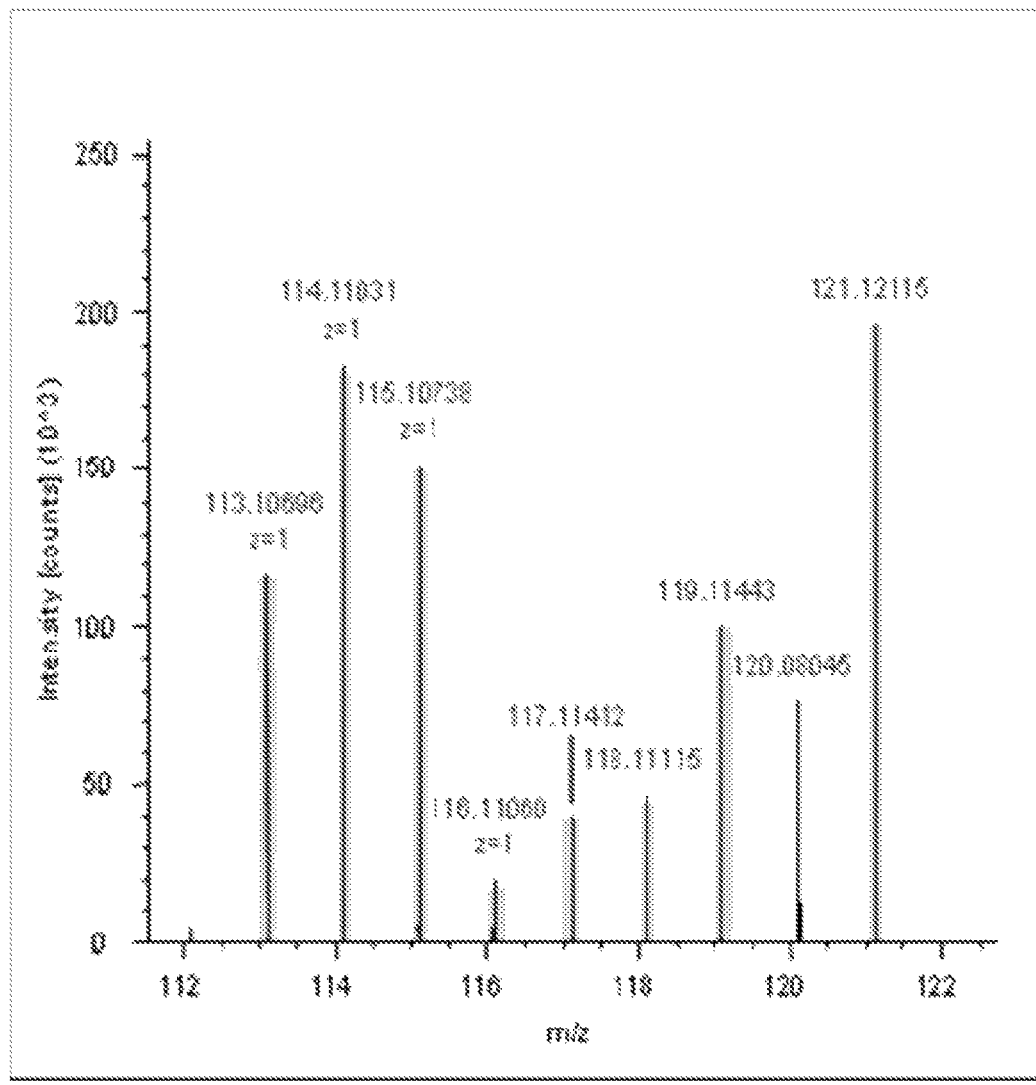
FIG. 8B: microfibrillar-associated protein 4 (peptide: fnGSVSFFR)
Figure 8C:
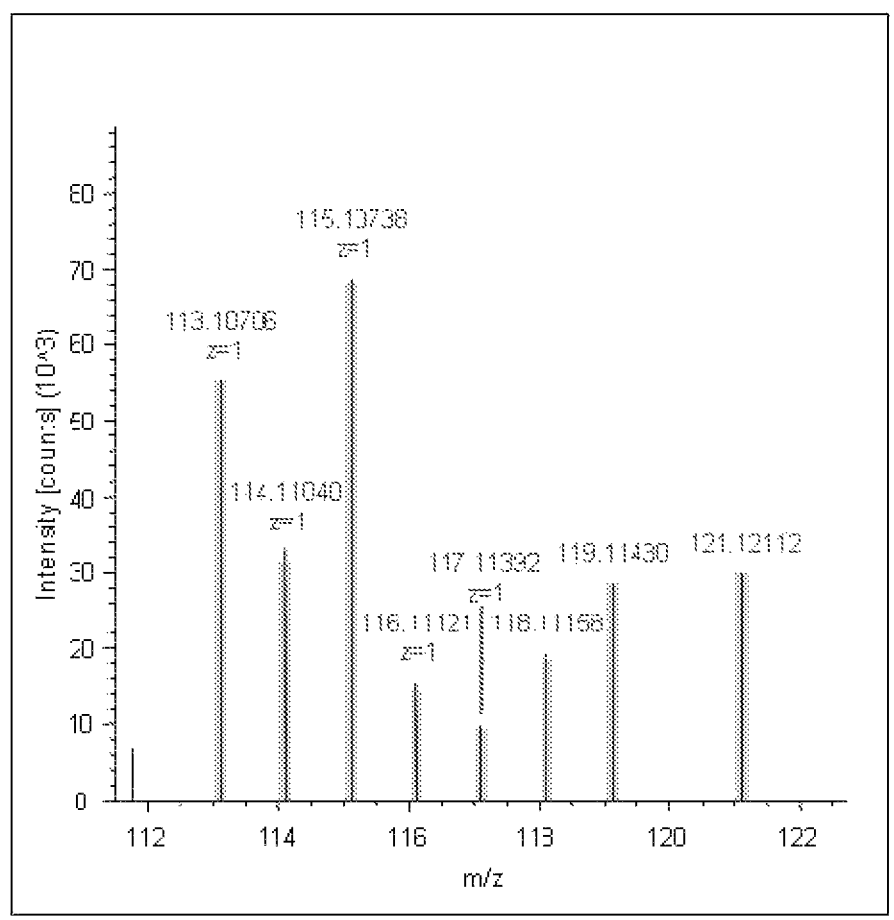
FIG. 8C: periostin.
Figure 8D:
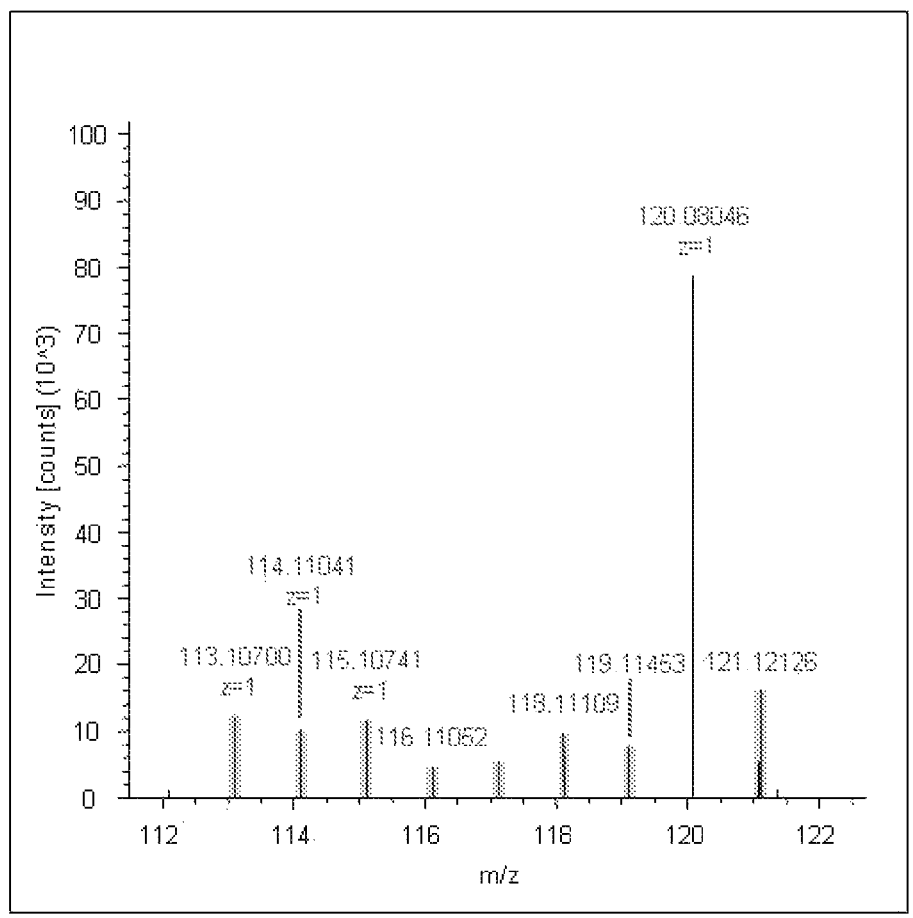
FIG. 8D: cathepsin L.
Figure 10:
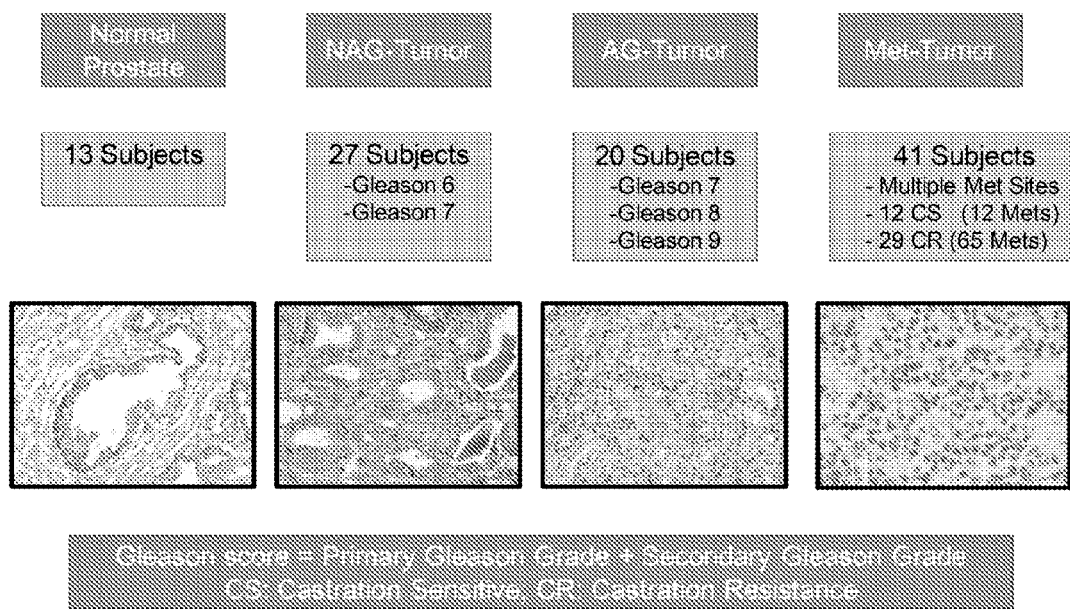
FIG. 10 shows the types of tissue specimens used in the validation study.
Figure 11A:
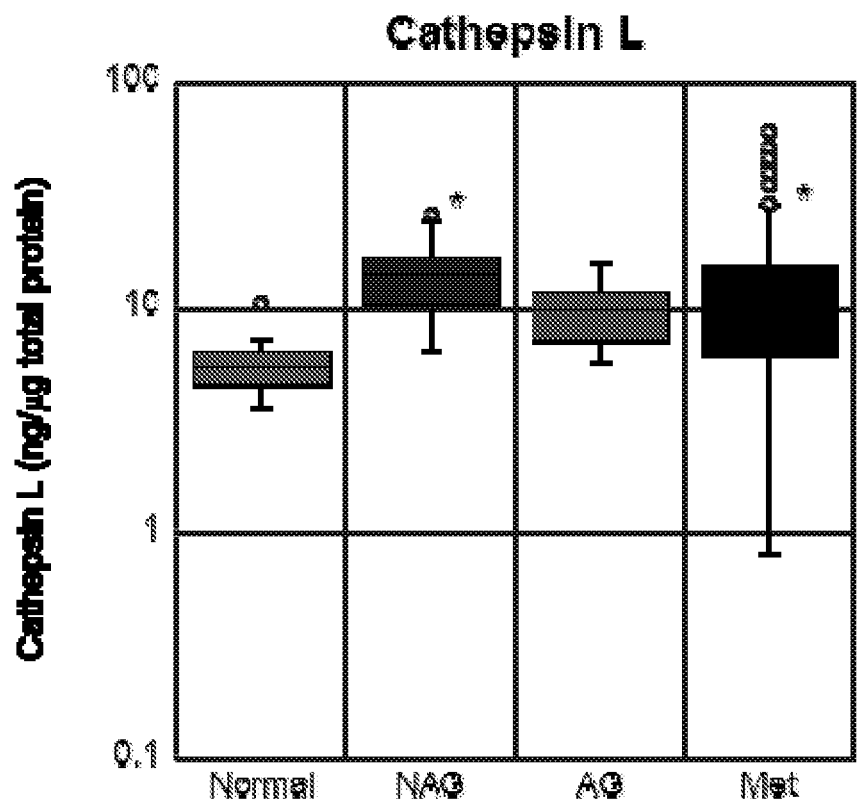
FIG. 11 shows Cathepsin-L (CTSL) levels in non-aggressive tumor (NAG) vs. aggressive tumor (AG).
Figure 11B:
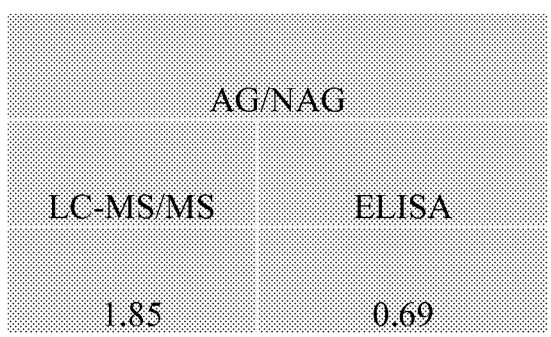
Figure 12:
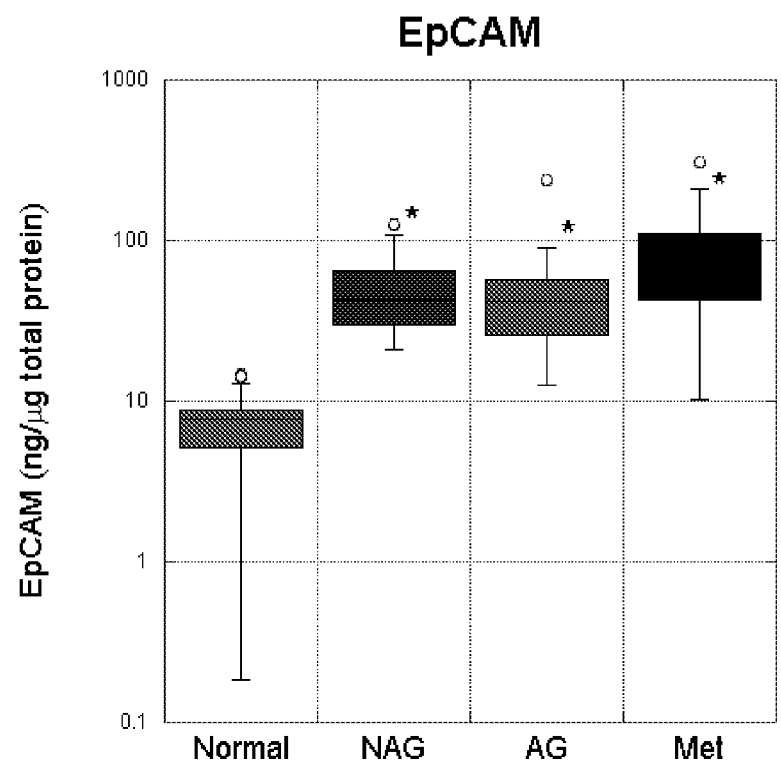
FIG. 12 shows Epithelial Cell Activating Molecule (EpCAM) levels in normal prostate, NAG, AG, and Met.
Figure 13:
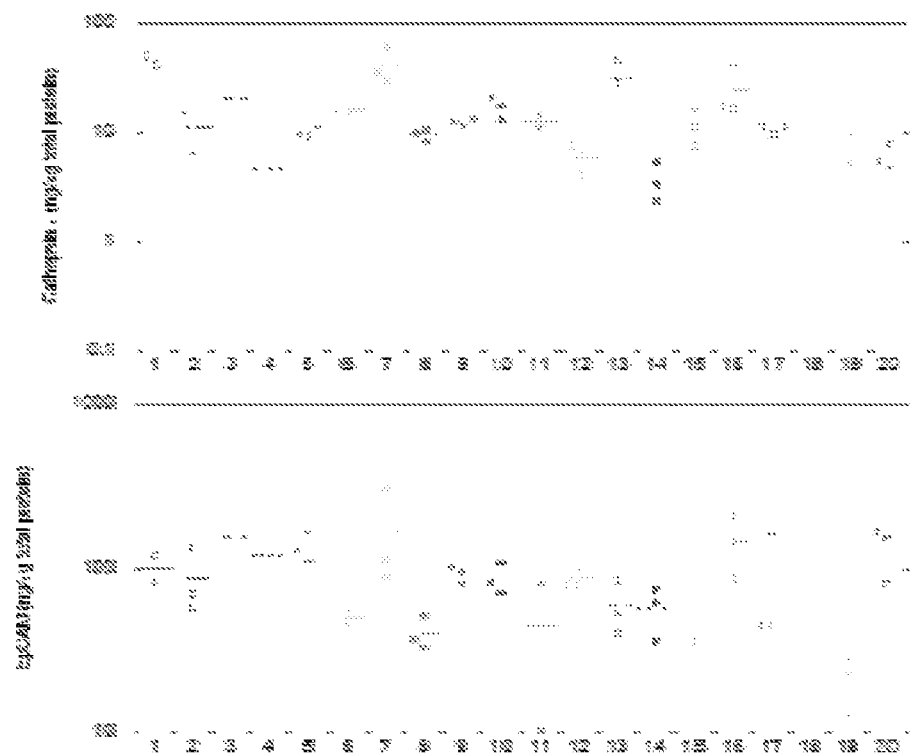
FIG. 13 shows expression of CTSL and EpCAM in multiple mets by subject.
Figure 14A:
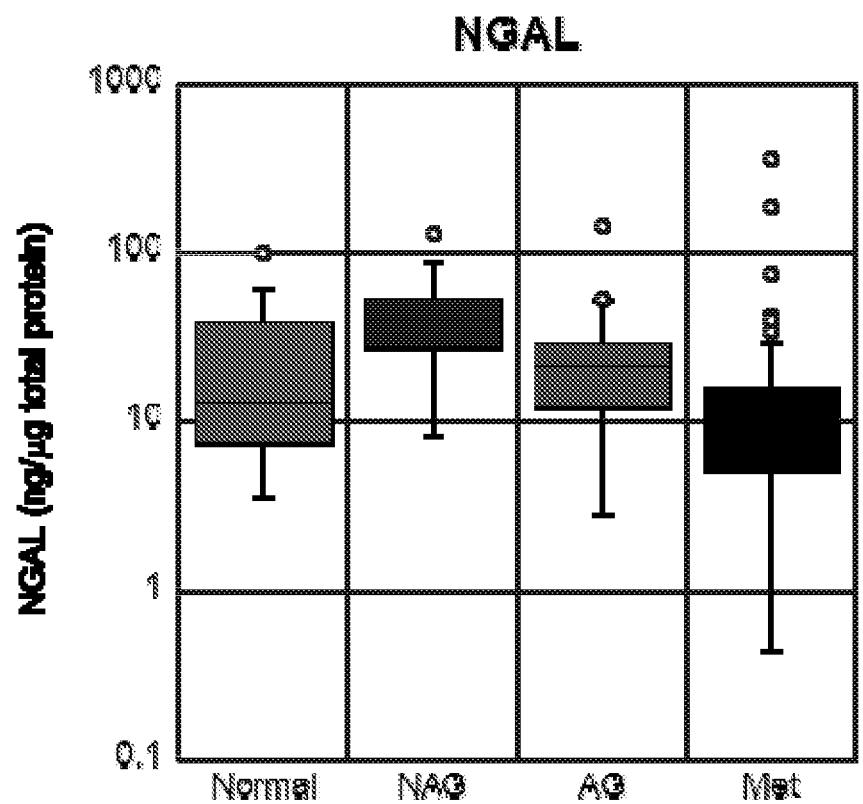
FIG. 14 shows human Neutrophil Gelatinase Associated Lipocalin (NGAL) levels in normal prostate, NAG, AG, and Met.
Figure 14B:
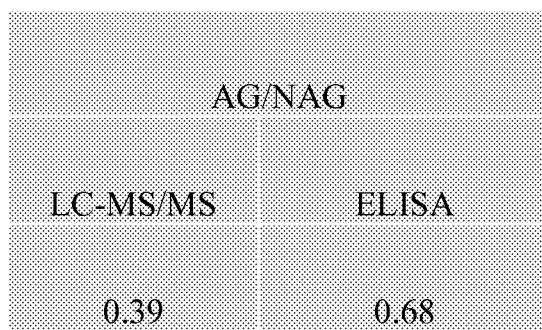
Figure 15A:
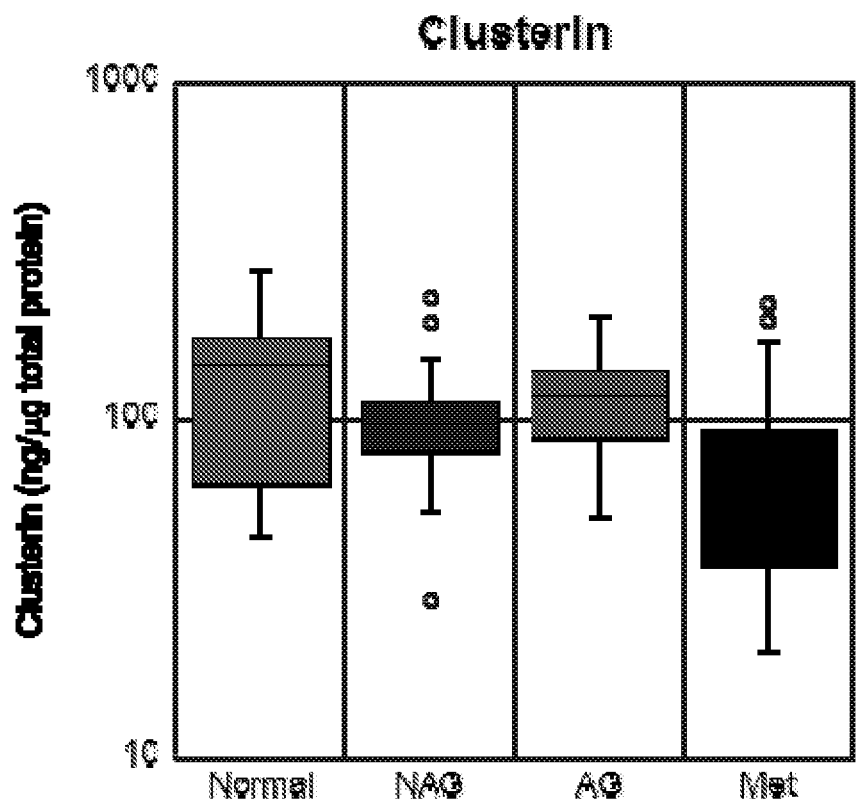
FIG. 15 shows Clusterin levels in normal prostate, NAG, AG, and Met.
Figure 15B:
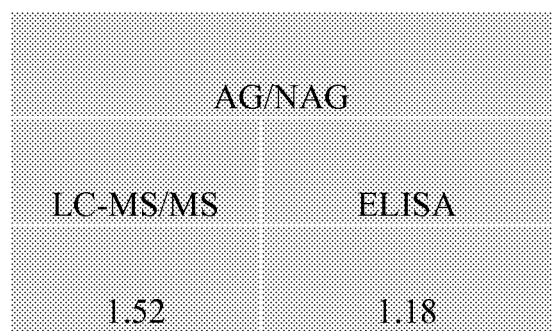
Figure 16A:
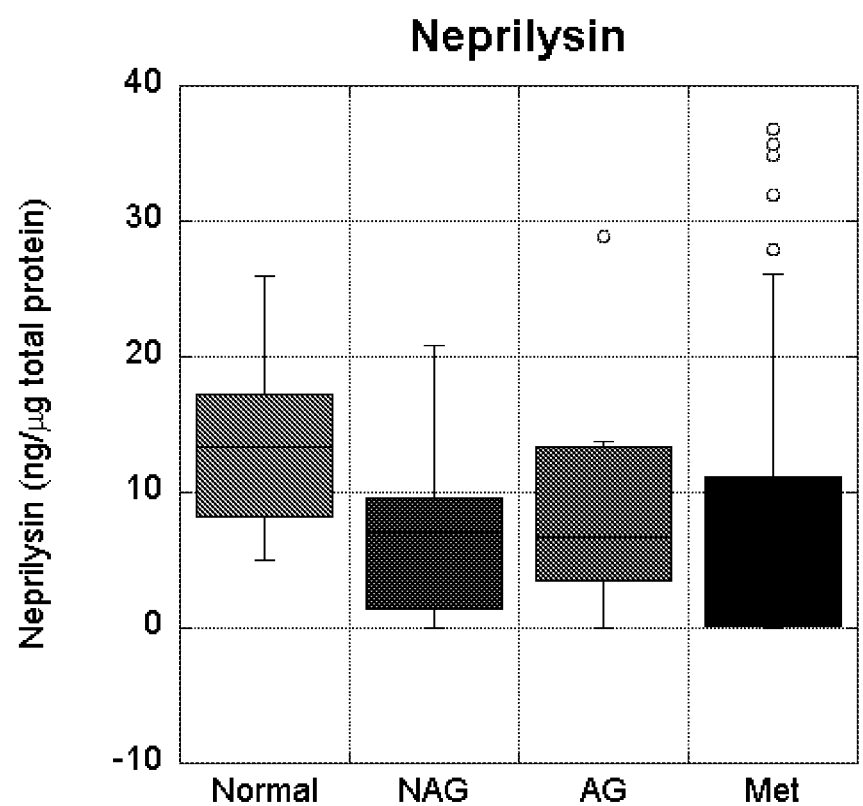
FIG. 16 shows Neprilysin levels in normal prostate, NAG, AG, and Met.
Figure 16B:
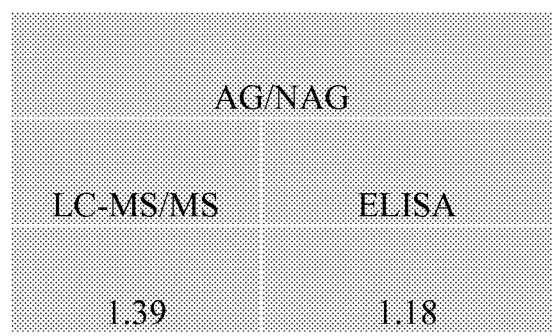
Figure 17:
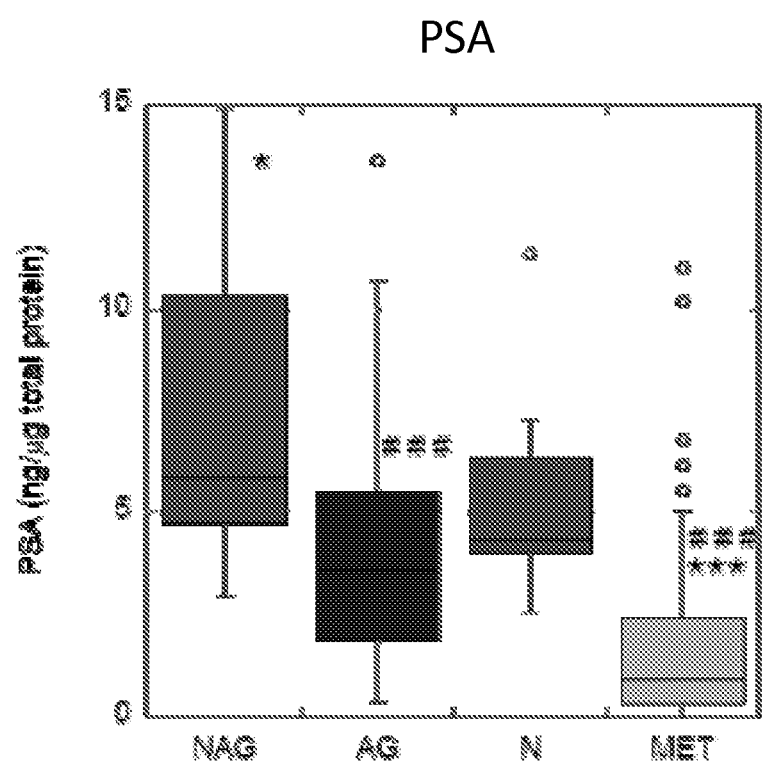
FIG. 17 shows total prostate specific antigen (PSA) levels in NAG, AG, normal prostate and Met.
Figures 18A, 18B:
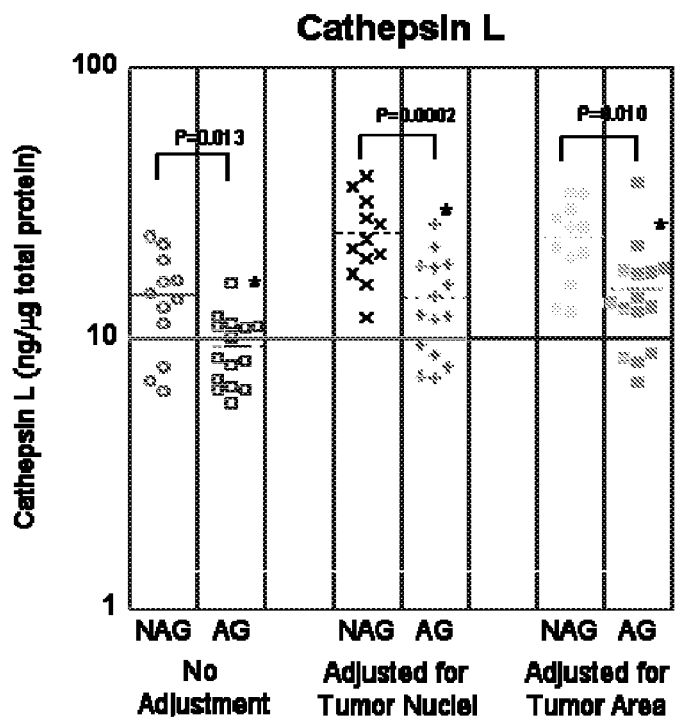
FIG. 18 shows CTSL levels in NAG vs. AG (no adjustment, adjusted for tumor nuclei, and adjusted for tumor area).
Figures 19A, 19B:
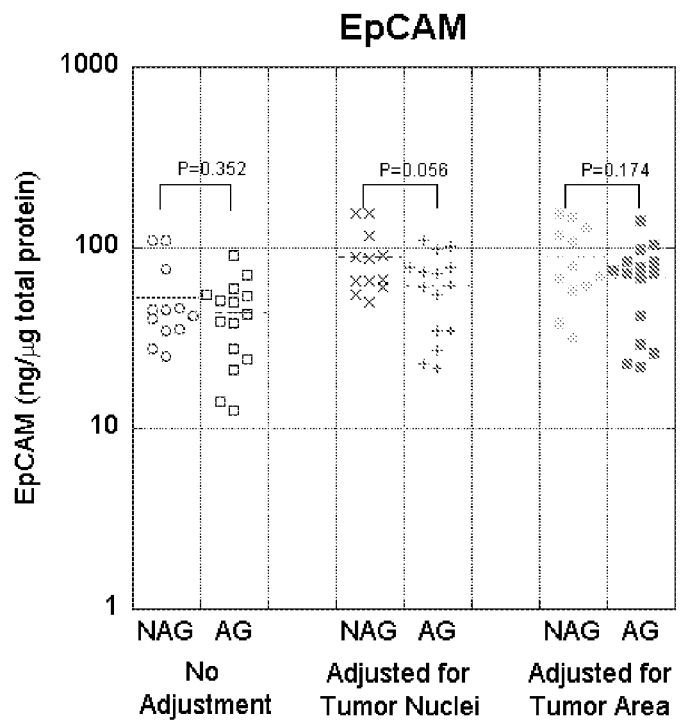
FIG. 19 shows EpCAM levels in NAG vs. AG (no adjustment, adjusted for tumor nuclei, and adjusted for tumor area).
Figure 20A:
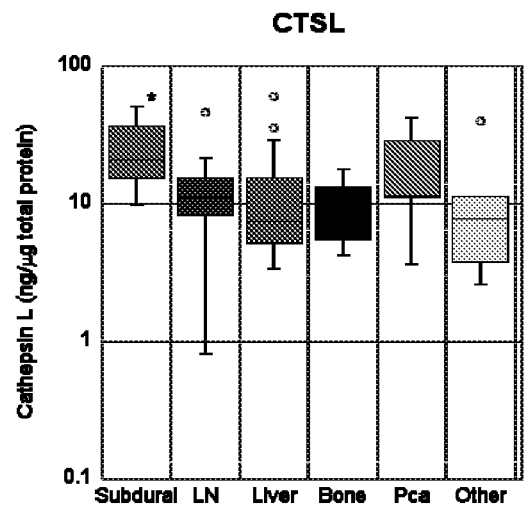
FIG. 20 shows biomarker levels in metastatic tumors by site for CTSL (FIG. 20A), Clusterin (FIG. 20B), EpCAM (FIG. 20C), NGAL (FIG. 20D), MME (FIG. 20E), and PSA (FIG. 20F). Sites include subdural, lymph node (LN), liver, bone, prostate, and other.
Figure 20B:
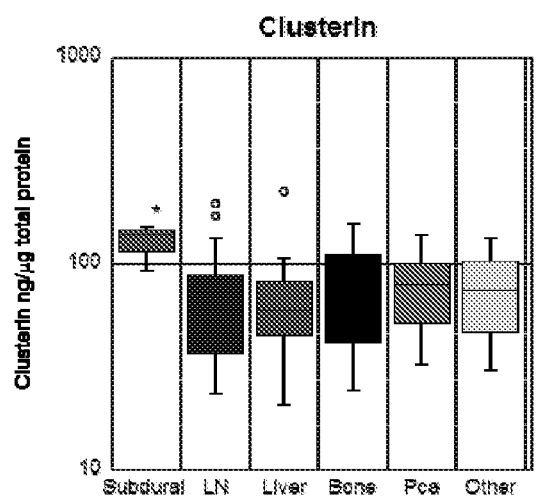
Figure 20C:
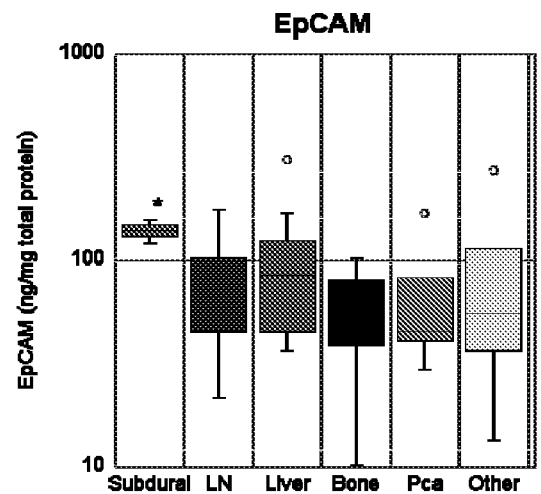
Figure 20D:
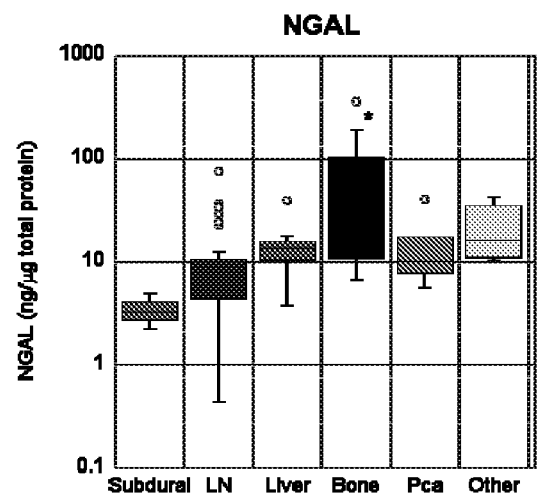
Figure 20E:
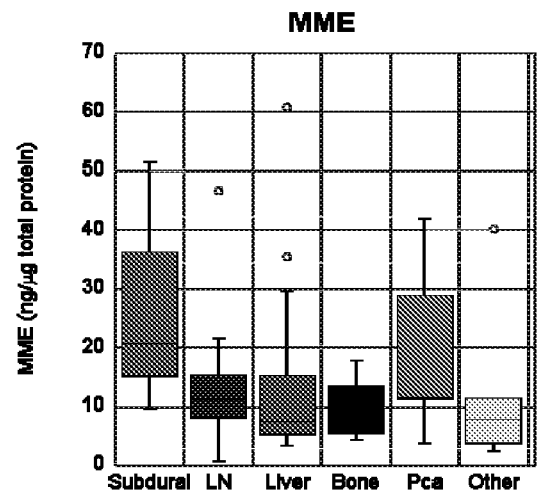
Figure 20F:
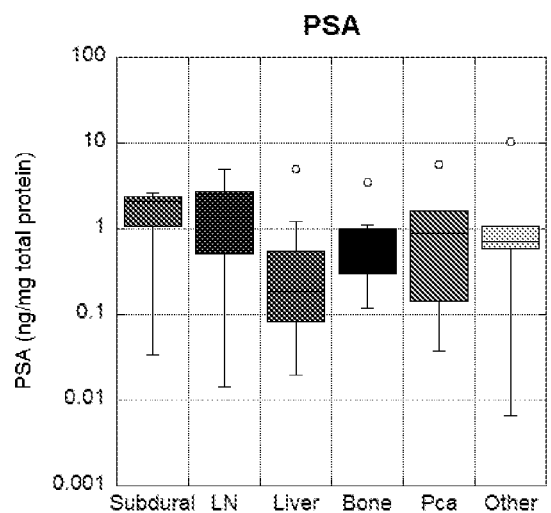
Figure 21:
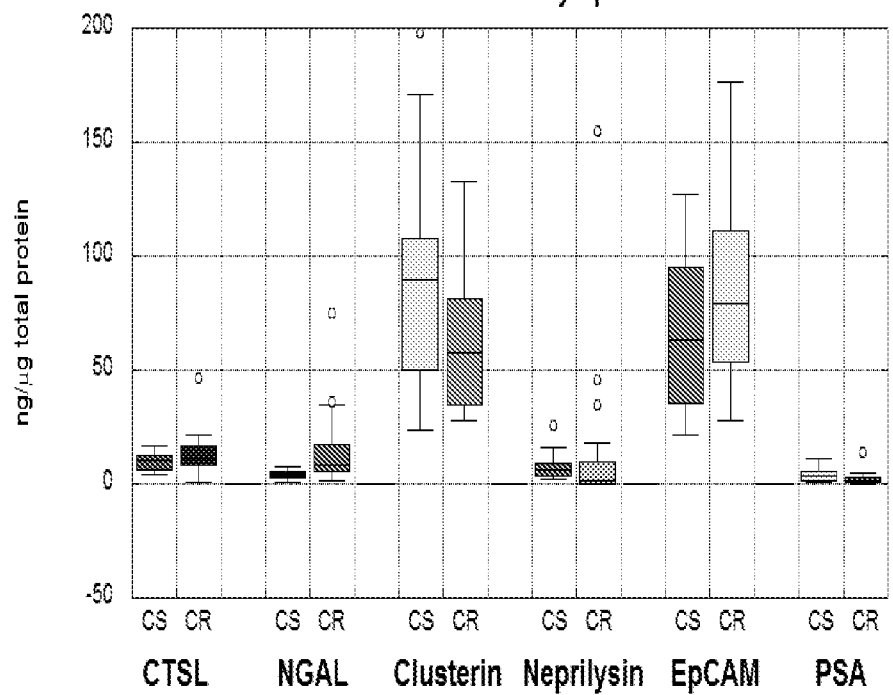
FIG. 21 shows biomarker levels in castrations sensitive vs. castration resistant lymph node metastatic prostate tumors.
Figure 22:
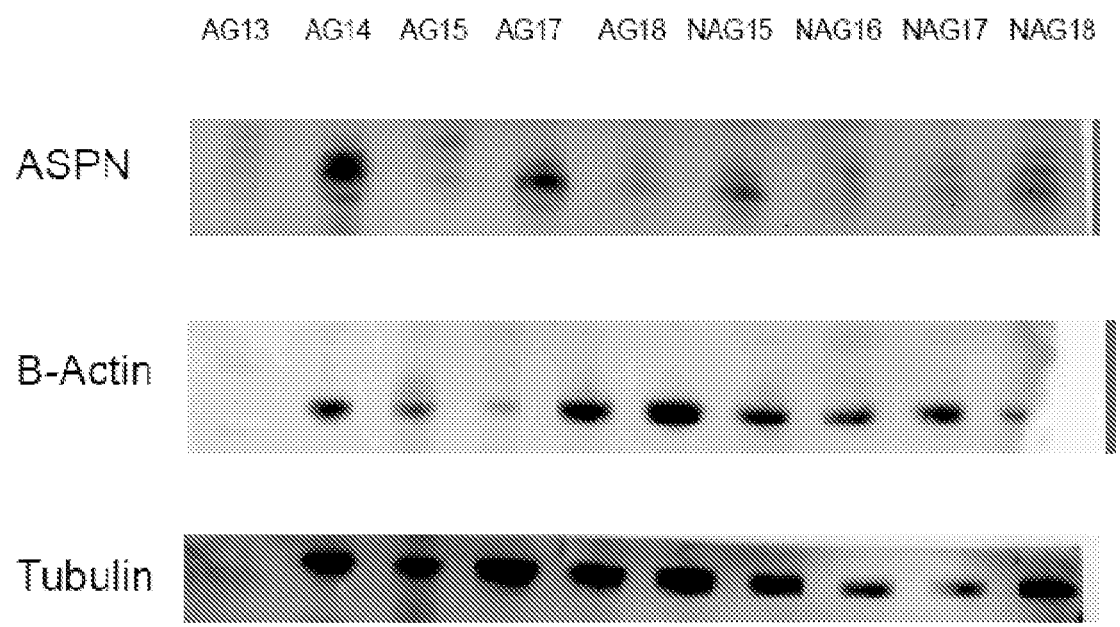
FIG. 22 is a Western blot 5 AG and 4 NAG and showing significant Asporin (ASPN) expression in some AG subjects.
Figure 23:
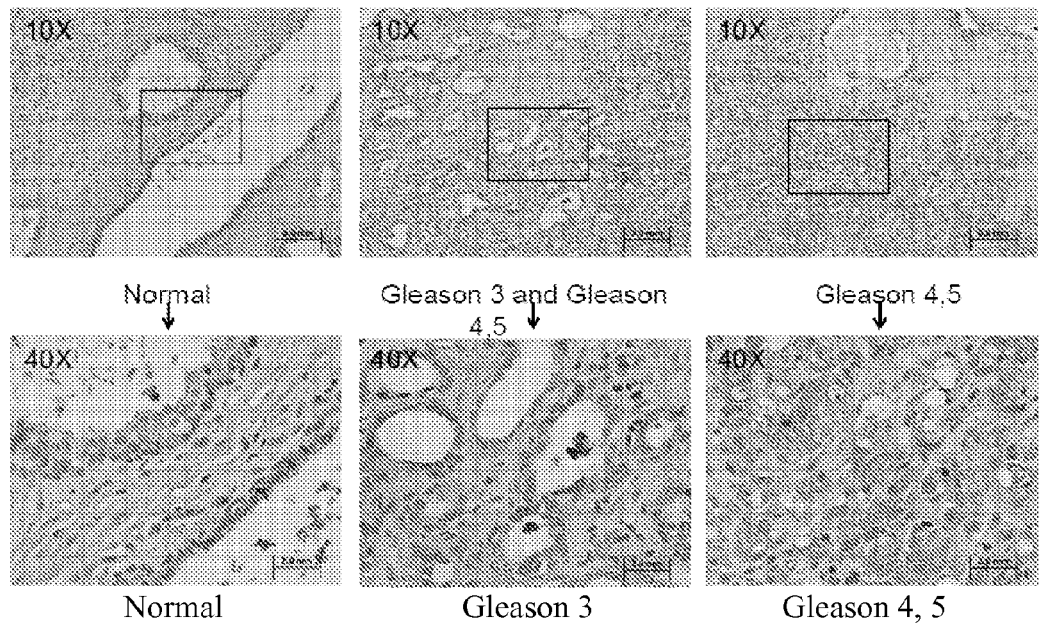
FIG. 23. shows immunostaining results for ASPN Immunostaining subject PB663 (AG17, intermediate ASPN expression in Western blot (FIG. 23)) showed strong ASPN staining for high grade Pca with no/weak staining for Gleason 3 Pca and normal prostate gland.

Cathepsin L and periostin were further analyzed in primary prostate tumors and normal prostate tissues using immunohistochemistry. FIG. 4A shows the cathepsin L staining in primary prostate tumor and its adjacent normal tissue. Staining was detected in both normal and tumor epithelial cells. However, the percentage of cells stained with cathepsin L was increased in the prostate tumor (FIG. 4A) with apparent increased staining in aggressive cancer, consistent with iTRAQ results (data not shown).

FIG. 4B shows the immunohistochemistry staining of periostin in primary prostate cancer tissues. The staining exhibited a low background in the normal prostate samples but revealed an overexpression in the peritumoral stroma of Gleason 3 tumors and strong overexpression in the peritumoral stroma of Gleason 4 tumors. This indicates that periostin expression may correlate with aggressive prostate cancer.

Discussion

Several glycoproteins were identified in this study and showed significant altered expression in aggressive prostate tumors compared to nonaggressive prostate tumors. To the present inventors' knowledge, this is the first glycoproteomic study to elucidate the differentially expressed proteins associated with aggressive prostate cancer to identify proteins that are potentially useful for diagnosis of aggressive prostate cancer. Furthermore, though OCT-embedded tissues have been used in proteomic analyses, this study was the first to demonstrate the use of OCT-embedded frozen tissues in MS-based glycoproteomic analysis. These findings may facilitate the usage of OCT-embedded frozen tissues in biomarker discovery.

Tumor invasion and metastasis is a complicated and multifaceted process which may include intravasation, survival in the circulatory system, arrest and extravasation into a new tissue, initiation and maintenance of tumor cell growth, and reactivation of angiogenesis. In this multistep process, interactions between cancer cells and stromal cells as well as between cancer cells and the extracellular matrix (ECM) are required. Therefore, component changes in the ECM within the tumor microevironment could play a fundamental impact on the metastatic process.

Cathepsin L acts as endopeptidase, which can degrade many intracellular and extracellular proteins and thereby modify their function. Cathepsin L has been reported to be upregulated in a variety of malignancies including breast, lung, colon, gastric, head, and neck carcinomas, melanomas, and gliomas. Furthermore, overexpression of cathepsin L correlates positively with malignancy. Several studies have revealed that cathepsin L plays an important role in the processes of invasion and migration. The data show that cell-cell adhesion is diminished and degradation of ECM is increased when extracellular activity of cathepsin L increases, which suggests that cathepsin L can increase metastatic tumor development. Studies have also found that inhibition of cathepsin L mRNA decreased tumor growth of murine myeloma and that anticathepsin L ScFv (single chain variable fragment) inhibited the tumorigenic and metastatic phenotype of human melanoma.

Periostin is a unique and important ECM protein involved in cell development and adhesion. Periostin has been shown to interact with many other ECM proteins, including fibronectin, collagen V, tenascin-C and periostin itself. The epithelial-mesenchymal transition (EMT), which gives epithelial cancer cells invasive and metastatic potential, is one of the critical steps of tumor metastasis, and it has been shown that periostin can facilitate cell migration and differentiation during EMT. Periostin has also been found to be overexpressed in various types of human cancer, such as breast cancer, colon cancer, lung cancer, pancreatic cancer, prostate cancer, and ovarian cancer. Most recently, periostin was found to be overexpressed in prostate cancer tissue compared to benign prostate hyperplasia. However, our study is the first to discover the overexpression of periostin in aggressive prostate cancer using quantitative glycoproteomics and mass spectrometry. Consistent with the present glycoproteomics findings, periostin was found to promote tumor metastasis in colon cancer, melanoma, head and neck squamous cell carcinoma, gastric cancer, and lymph node metastases. For example, the average expression level of periostin is not increased in primary tumors of melanoma, whereas periostin overexpression is found in around 60% of metastatic melanoma tumors in the liver or lymph nodes.

Microfibrillar-associated protein-4 (MFAP4) is an ECM protein that is upregulated in aggressive prostate cancer. MFAP4 binds to collagen and contains a C-terminal fibrinogen-like domain and an N-terminal integrin-binding motif. The fibrinogen-like domain is responsible for the carbohydrate binding activity. The N-terminal part of MFAP4 includes one cysteine-residue and a ligand motif Arg-Gly-Asp (RGD) for cell surface integrins. The function of MFAP4 is not yet clear. Human recombinant MFAP4 was reported to bind the collagen domain of surfactant protein A (SP-A), which suggests that MFAP4 may be involved in inflammatory processes. In a study of MFAP4 in catfish, Niu et al. reported that MFAP4 may play a novel role in teleost immune responses.

In this study, the coupregulation of cathepsin L and several ECM proteins, such as periostin, and microfibrillar-associated protein-4, in aggressive prostate tumor may indicate that there are some interactions among ECM proteins to facilitate the process of prostate tumor metastasis. Further studies will facilitate the understanding of the mechanisms involved in the function, regulation, and biological activities of cathepsin L and ECM proteins in tumor metastasis.

There has been a concern about using OCT-embedded frozen tissue in mass spectrometry analysis. OCT contains several chemicals to lower freezing temperature, such as PEG, which may suppress ionization and cause contamination of mass spectrometry analysis. Somiari and co-workers presented the first high-throughput proteomic analysis of human breast infiltrating ductal carcinoma using OCT-embedded biopsies, using two-dimensional gel electrophoresis (2-D DIGE) technology. Asomugha et al. used the same technologies for identification of crystalline modifications in the human lens cortex and nucleus. 2-D DIGE could separate the proteins from the OCT chemicals so as to avoid contaminating the mass spectrometers. However, to the best of our knowledge, directly analyzing OCT samples with mass spectrometry has not been reported. Our strategy of using solid phase extraction of N-glycopeptide overcomes this difficulty by chemical immobolization of glycopeptides and subsequent removing OCT in the washing step so that the glycopeptides isolated from OCT-embedded tissues could be isotopically labeled and directly injected to mass spectrometry instruments for protein identification and quantification. In our study, glycopeptides were readily identified from the OCT-embedded frozen tissues and no contamination was detected in the spectrum of mass spectrometry analysis. These results demonstrate (1) the protein glycosylation is preserved in the OCT-embedded frozen tissues; (2) the OCT in the sample can be removed during the procedure of glycopeptide capture to eliminate the interference of OCT to the mass spectrometry analysis. Therefore, OCT-embedded frozen tissues can be used for glycoproteomic analysis and can provide invaluable specimen sources for identification of glycoprotein biomarkers.

We claim:

1. A method comprising measuring the levels of periostin, cartilage oligomatrix protein, glutamate carboxypeptidase 2, dipeptidyl peptidase 4, carboxypeptidase E, aminopeptidase N, chymase, asporin and versican core protein by performing multiple reaction monitoring mass spectrometry (MRM-MS) with a sample collected from a patient.

2. The method of claim 1, wherein the sample is a blood, plasma, or serum sample.

3. The method of claim 2, wherein the sample is a blood sample.

4. The method of claim 2, wherein the sample is a plasma sample.

5. The method of claim 2, wherein the sample is a serum sample.

6. The method of claim 1, wherein the sample is a tissue sample.

7. The method of claim 6, wherein the sample is an embedded tissue sample.

* * * * *